United States Patent
Qian

(10) Patent No.: US 9,546,179 B2
(45) Date of Patent: Jan. 17, 2017

(54) HETEROCYCLE AMIDO ALKYLOXY SUBSTITUTED QUINAZOLINE DERIVATIVE AND USE THEREOF

(71) Applicant: Wei Qian, Shanghai (CN)

(72) Inventor: Wei Qian, Shanghai (CN)

(73) Assignee: Wei Qian (CN)

(*) Notice: Subject to any disclaimer, the term of this patent is extended or adjusted under 35 U.S.C. 154(b) by 213 days.

(21) Appl. No.: 14/002,415

(22) PCT Filed: Dec. 13, 2012

(86) PCT No.: PCT/CN2012/086533
§ 371 (c)(1),
(2) Date: Dec. 27, 2013

(87) PCT Pub. No.: WO2013/091507
PCT Pub. Date: Jun. 27, 2013

(65) Prior Publication Data
US 2014/0206664 A1 Jul. 24, 2014

(30) Foreign Application Priority Data

Dec. 20, 2011 (CN) .......................... 2011 1 0431070

(51) Int. Cl.
| | | |
|---|---|---|
| *C07D 491/107* | (2006.01) | |
| *C07D 487/10* | (2006.01) | |
| *C07D 487/04* | (2006.01) | |
| *C07D 491/06* | (2006.01) | |
| *C07D 495/10* | (2006.01) | |
| *C07D 471/04* | (2006.01) | |
| *C07D 498/08* | (2006.01) | |
| *C07D 471/10* | (2006.01) | |
| *C07D 401/12* | (2006.01) | |
| *C07D 403/14* | (2006.01) | |
| *C07D 239/94* | (2006.01) | |

(52) U.S. Cl.
CPC ......... *C07D 491/107* (2013.01); *C07D 239/94* (2013.01); *C07D 401/12* (2013.01); *C07D 403/14* (2013.01); *C07D 471/04* (2013.01); *C07D 471/10* (2013.01); *C07D 487/04* (2013.01); *C07D 487/10* (2013.01); *C07D 491/06* (2013.01); *C07D 495/10* (2013.01); *C07D 498/08* (2013.01)

(58) Field of Classification Search
CPC . C07D 491/107; C07D 471/10; C07D 487/04; C07D 487/10; C07D 491/06; C07D 471/04; C07D 498/08; C07D 495/10; C07D 403/14; C07D 239/94; C07D 401/12
See application file for complete search history.

(56) References Cited

U.S. PATENT DOCUMENTS

| | | | |
|---|---|---|---|
| 5,616,582 A | 4/1997 | Barker | |
| 6,391,874 B1 | 5/2002 | Cockerill et al. | |
| 6,617,329 B2 * | 9/2003 | Himmelsbach | A61K 31/505 |
| | | | 514/211.15 |
| RE41,065 E | 12/2009 | Schnur et al. | |
| 2014/0228361 A1* | 8/2014 | Zhang | C07D 403/12 |
| | | | 514/230.5 |

FOREIGN PATENT DOCUMENTS

| | | | |
|---|---|---|---|
| CN | 101003515 A | * | 7/2007 |
| CN | 101289445 A | * | 10/2008 |
| CN | 102796109 A | * | 11/2012 |

OTHER PUBLICATIONS

Bradbury et al. "4-Anilino quinazoline derivatives as antiproliferative agents." CN 101003515 A (Jul. 25, 2007) English machine translation obtained on Sep. 30, 2015 from <https://www.google.com/patents/CN101003515A?cl=en>.*
Duan et al. "Aniline quinazoline derivatives, preparation method and uses thereof" CN 101289445A (Oct. 22, 2008), English machine translation (Espacenet).*
Zhao et al. "4-aminoquinazoline compound and preparation method and application thereof" CN102796109A (Nov. 28, 2012) English machine translation from www.epo.org.*
Sridhar K. Rabindran et al., "Antitumor Activity of HKI-272, an Orally Active, Irreversible Inhibitor of the HER-2 Tyrosine Kinase," Cancer Research 64, 3958-3965, Jun. 1, 2004.
Georgios Giamas et al., "Kinases as targets in the treatment of solid tumors," Cellular Signalling 22 (2010) 984-1002, www.elsevier.com/locate/cellsig.

(Continued)

*Primary Examiner* — Nyeemah A Grazier
*Assistant Examiner* — Amanda L Aguirre
(74) *Attorney, Agent, or Firm* — Banner & Witcoff, Ltd.

(57) ABSTRACT

Heterocycle amino alkyloxy substituted quinazoline derivatives as represented by the structural Formula (I) and pharmaceutically acceptable salts thereof, capable of inhibiting the activity of receptor tyrosine kinase EGFR, and being used to treat cancers related to the expression of the receptor tyrosine kinase of the ErbB family are provided.

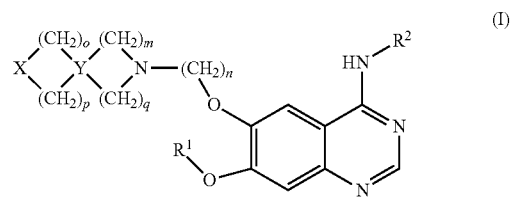

6 Claims, 1 Drawing Sheet

(56) References Cited

OTHER PUBLICATIONS

Figure 1:
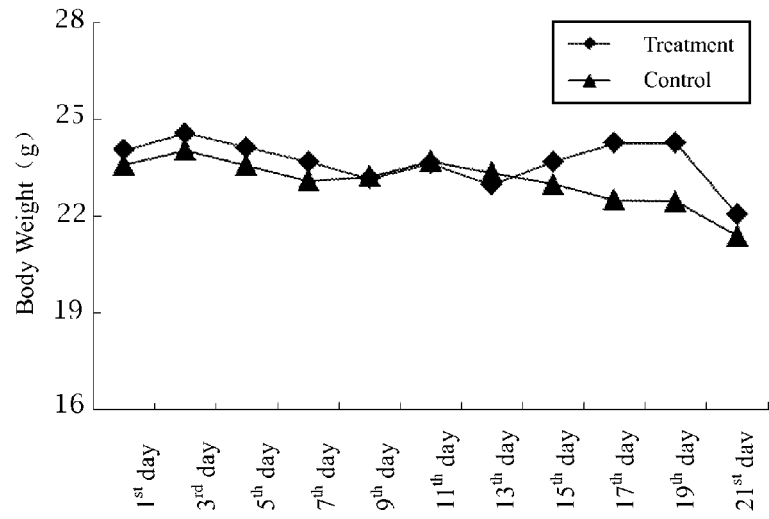

L. K. Seymour., "Epidermal Growth Factor Receptor as a Target: Recent Developments in the Search for Effective New Anti-Cancer Agents," Current Drug Targets, 2001, vol. 2, No. 2, 117-133.
Alexander J. Bridges et al., "Tyrosine Kinase Inhibitors. 8. An Usually Steep Structure—Activity Relationship for Analogues of 4-(3-Bromoanilino)-6, 7-dixmethoxyquinazoline (PD 153035), a Potent Inhibitor of the Epidermal Growth Factor Receptor," J. Med. Chem. 1996, vol. 39, No. 1, pp. 267-276.
D Li et al., "BIBW2992, an irreversible EGFR/HER2 inhibitor highly effective in preclinical lung cancer models," Oncogene (2008) 27, 4702-4711, www.nature.com.onc.
Maria Sundvall et al., "EGFR targeting drugs in the treatment of head and neck squamous cell carcinoma," Expert Opinion, Emerging Drugs (2010) 15(2):185-201.
Carlo Gannbacorti-Passerini., "Part I: Milestones in personalised medicine—imatinib," Lancet Oncol 2008; vol. 9, p. 600, http://oncology.thelancet.corn.

* cited by examiner

US 9,546,179 B2

HETEROCYCLE AMIDO ALKYLOXY SUBSTITUTED QUINAZOLINE DERIVATIVE AND USE THEREOF

RELATED APPLICATION DATA

This application is a National Stage Application under 35 U.S.C. 371 of co-pending PCT application PCT/CN2012/086533 designating the United States and filed Dec. 13, 2012; which claims the benefit of CN application number 201110431070.9 and filed Dec. 20, 2011 each of which are hereby incorporated by reference in their entireties.

TECHNICAL FIELD

This invention relates to a substituted quinazoline derivative. The invention especially relates to heterocycle amino alkyloxy substituted quinazoline derivatives and pharmaceutically acceptable salts thereof. The derivative is used as active ingredient to inhibit the activity of receptor tyrosine kinase EGFR, and to reduce phosphorylation of the kinase on tyrosine residue contained in substrate and effectively improve and treat a variety of diseases (e.g. tumor) thus caused.

BACKGROUND

Traditional chemotherapeutic drugs treat cancer by inhibiting DNA synthesis or inhibiting cell division. Practice shows that these compounds also have certain toxicity to normal cells. However, the molecular targeted therapies (MTTs) developed in the past one or two decades can greatly lower the toxicity of drugs to normal cells. Imatinib, which is used as therapy of Chronic Myeloid Leukemia (CML), has become one of the breakthrough milestones in the field (The Lancet Oncology, 2008, 600).

Epidermal growth factor receptor (EGFR/ErbB1/HER1 a transmembrane protein having a molecular weight of approximately 170 kD, is a member of receptor tyrosine kinase ErbB Family. This family includes members such as EbB2/HER2/Neu, ErbB3/HER3, ERbB4/HER4 and the like. After a ligand that is similar to EGF (e.g. EGF and TGF-α) conjugates to the receptor, dimerization occurs, thus activating a signaling pathway within a variety of downstream cells, e.g. PI3K/Akt, MAPK, signal transducers and activators of transcription (STAT), and the like. These signaling pathways are involved in the significant physiological processes, such as regulation, migration, cell death, cell growth, and the like. (Expet. Opin. Emerg. Drugs, 2010, 185).

Many studies have shown that a variety of tumor cells are directly related to over-expression of EGFR and over-expression of EGFR ligand (Curr. Drug Targets, 2001, 2, 117-133). The growth of multiple types of tumor cells can be effectively controlled by inhibiting the conjugation between EGFR and its ligand as well as activity of EGFR tyrosine kinase. There are a variety of drugs to inhibit EGFR for treating cancer currently in clinical trials. These cancers include lung cancer, colon cancer, gastric cancer, breast cancer, ovarian cancer, leukemia, prostate cancer, uterine cancer, pancreatic cancer, liver cancer, bladder cancer, renal cancer, thyroid cancer, brain cancer, head and neck cancer, and the like. (Cell. Signal., 2010, 22, 984-1002).

The research and development of antitumor drugs against EGFR is mainly concentrated on the antibody drug and small molecule compounds that inhibit the tyrosine kinase receptor. The first generation of small molecule compounds are reversible kinase inhibitors, such as Astra-Zeneca's Gefitinib (U.S. Pat. No. 5,616,582), Roche's Erlotinib (U.S. RE41,065) and GlaxoSmithKline's (GSK) Lapatinib (U.S. Pat. No. 6,391,874), etc. The second generation of small molecule compounds are irreversible inhibitors, such as Boehringer Ingelheim's BIBW2992 (Oncogene, 2008, 27, 4702-4711) and Pfizer's Neratinib (Cancer Res. 2004, 64, 3958-3965), which are in Phase III clinical trials. Conjugating receptor kinase via covalent bonds, these compounds are better able to inhibit EGFR and related kinases, and demonstrate significantly higher inhibiting effectiveness, especially for cancer cells containing mutant receptor tyrosine kinases.

The it has been difficult to develop therapeutic drugs that target EGFR due to the secondary mutations in EGFR that cause drug resistance. in clinical settings, it is difficult to choose the right drug because of the diversity of kinase mutations. However, genetic testing and diagnostic tools, developed in recent years, have facilitated selecting drugs more effectively. It has become an inevitable development in direction of molecular targeted cancer treatment in the past one or two decades that treating cancer patients having different mutations with different types of drugs is necessary. Therefore, the development of more innovative drug molecules, that meet the medical need of different patients by providing more personalized cancer treatment drugs are desired.

DESCRIPTION OF THE INVENTION

In one aspect of the invention, a heterocycle amino alkyloxy substituted quinazoline derivative and a pharmaceutically acceptable salt thereof to inhibit EGFR and other receptor tyrosine kinases are provided.

In another aspect of the invention, a spiroheterocycle amino alkyloxy substituted quinazoline derivative and a pharmaceutically acceptable salt thereof to inhibit EGFR and other receptor tyrosine kinases are provided.

In another aspect of the invention, a bridged heterocycle amino alkyloxy substituted quinazoline derivative and a pharmaceutically acceptable salt thereof to inhibit EGFR and other receptor tyrosine kinases are provided.

In another aspect of the invention, a pharmaceutical composition containing a heterocycle amino alkyloxy substituted quinazoline derivative and a pharmaceutically acceptable salt thereof are provided as active ingredients, and applied to inhibit EGFR and other receptor tyrosine kinases.

In another aspect of the invention, a pharmaceutical composition containing a heterocycle amido alkyloxy substituted quinazoline derivative and a pharmaceutically acceptable salt thereof are provided as active ingredients, and applied to prepare the drugs for cancer treatment.

The present invention provides a heterocycle amino alkyloxy substituted quinazoline derivative and a pharmaceutically acceptable salt thereof, of which the compound structure as active ingredient is shown in Formula I

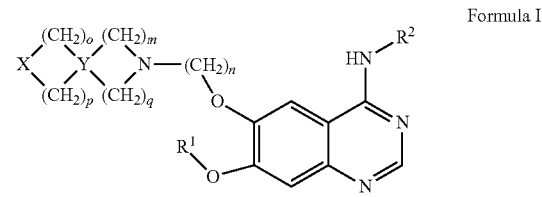

Formula I wherein, m, o, p and q are each independently selected from integer that is greater than or equals to zero, preferably selected the integer from 0 to 6, e.g. 0, 1, 2, 3, 4, 5, and 6; and more preferably selected the integer from 0 to 4; n is selected from integer that is larger than or equal to 2, preferably selected the integers from 2 to 4, e.g. 2, 3 and 4;

group Y is selected from atom C, CH—CH or CH—CH₂—CH₂—CH, atom C or two ends of group CH—CH and group CH—CH₂—CH₂—CH form covalent bonds with other groups.

group X is selected from atoms O, atom S, or one of the following groups:

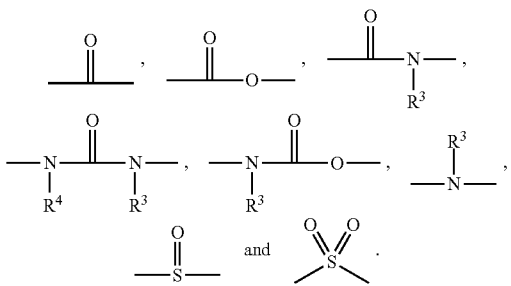

Group $R^3$ and group $R^4$ are respectively and independently selected from one of hydrogen, acyl, sulfonyl, substituted or unsubstituted C1-C6 alkyl, substituted or unsubstituted C3-C7 cycloalkyl, substituted or unsubstituted phenyl, and substituted or unsubstituted aromatic heterocyclyl.

Group $R^1$ is substituted or unsubstituted C1-C8 alkyl or substituted or unsubstituted C3-C7 cycloalkyl, preferably selected form C1-C8 alkyl, more preferred from C1-C3 alkyl, such as methyl (including —CH₃ and —CD₃ (deuterated methyl)) and ethyl (including —C₂H₆ and —C₂D₆ (deuterated ethyl)), or C3-C5 Cycloalkyl, such as cyclopropyl, or substituted C1-C3 alkyl, such as methoxyethyl and trifluoromethyl, or alkyl-substituted C3-C5 cycloalkyl, such as cyclopropyl methyl, and more preferably selected form the group of methyl, trifluoromethyl or methoxyethyl.

$R^1$ perssad is either substituted or unsubstituted C1-C8 alkyl or substituted or unsubstituted C3-C7 cycloalkyl with priority given to C1-C6 alkyl, especially C1-C3 alkyl, e.g. methyl including —CH₃ and —CD₃ (deuterated methyl) and ethyl including —C₂H₆ and —C₂D₆ (deuterated methyl); or C3-C5 cycloalkyl, e.g. cyclopropyl; or substituted C1-C3 alkyl, e.g. methoxyethyl and trifluoromethyl; or C3-C5 cycloalkyl substituted by alkyl, e.g. cyclopropyl methyl; methyl, trifluoromethyl or methoxyethyl is preferably selected.

Group $R^2$ is substituted or unsubstituted phenyl or substituted or unsubstituted aromatic heterocyclyl, preferably selected form the group of phenyl substituted by one or several from halogen, cyano, alkyl, alkenyl and alkynyl, or aromatic heterocyclyl substituted by one or several from halogen, cyano, alkyl, alkenyl and alkynyl.

In Formula I of the present invention, the group present at the position 4 of quinazoline includes, but is not limited to, 3-Chloro-4-Fluoroaniline, 3-Chloro-2-Fluoroaniline, 5-Chloro-2-Fluoroaniline and 3-Ethynylaniline.

In another embodiment of a spiroheterocyclic amido alkyloxy substituted quinazoline derivative and pharmaceutically acceptable salts thereof, the active ingredients of the compounds are as represented by Formula II-I:

Formula II-I

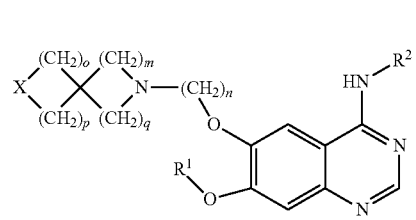

wherein m, o, p and q are each independently selected from integer that is greater than or equals to zero, preferably selected the integer from 0 to 6, e.g. 0, 1, 2, 3, 4, 5, and 6; and more preferably selected the integer from 0 to 4; n is selected from integer that is larger than or equal to 2, preferably selected the integers from 2 to 4, e.g. 2, 3 and 4;

Group X is selected from atoms O, atom S, or one of the following groups:

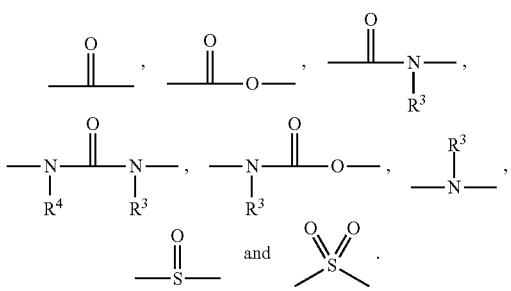

Group $R^3$ and group $R^4$ are respectively and independently selected from one of hydrogen, acyl, sulfonyl, substituted or unsubstituted C1-C6 alkyl, substituted or unsubstituted C3-C7 cycloalkyl, substituted or unsubstituted phenyl, and substituted or unsubstituted aromatic heterocyclyl.

Group $R^1$ is substituted or unsubstituted C1-C8 alkyl or substituted or unsubstituted C3-C7 cycloalkyl.

Group $R^2$ is substituted or unsubstituted phenyl or substituted or unsubstituted aromatic heterocyclyl, preferably selected form the group of phenyl substituted by one or several from halogen, cyano, alkyl, alkenyl and alkynyl, or aromatic heterocyclyl substituted by one or several from halogen, cyano, alkyl, alkenyl and alkynyl.

In another embodiment of a spiroheterocyclic amino alkyloxy substituted quinazoline derivative and pharmaceutically acceptable salts thereof, the active ingredients of the compounds are as represented by Formula II-II:

Formula II-II

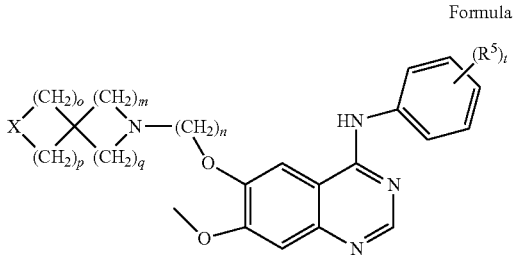

wherein m, o, p and q are each independently selected from integer that is greater than or equals to zero, preferably selected the integer from 0 to 6, e.g. 0, 1, 2, 3, 4, 5, and 6;

and more preferably selected the integer from 0 to 4; n is selected from integer that is larger than or equal to 2, preferably selected the integers from 2 to 4, e.g. 2, 3 and 4;

group X is selected from atoms O, atom S, or one of the following groups:

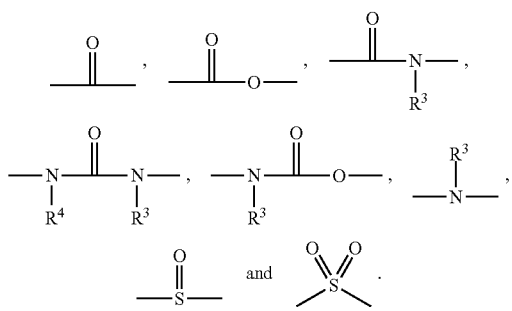

Group $R^3$ and group $R^4$ are respectively and independently selected from one of hydrogen, acyl, sulfonyl, substituted or unsubstituted C1-C6 alkyl, substituted or unsubstituted C3-C7 cycloalkyl, substituted or unsubstituted phenyl, and substituted or unsubstituted aromatic heterocyclyl.

Group $R^1$ is selected from methyl, deuterated methyl, ethyl, deuterated ethyl, trifluoromethyl, methoxyethyl, cyclopropyl or cyclopropyl methyl.

t equals 1 or 2.

Each group $R^5$, which may be same or different, is independently chosen from fluoro, chloro, bromo, cyano, and C2-C4 alkynyl. The substituted phenyl ring includes, but is not limited to:

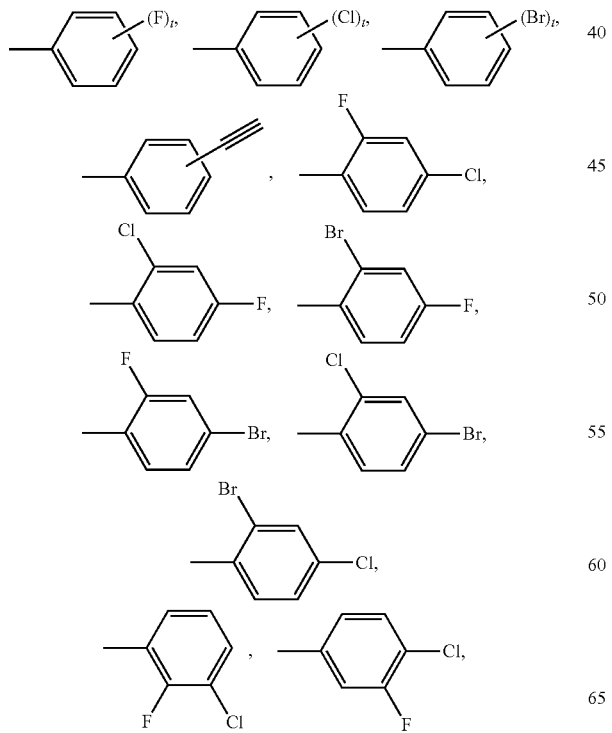

-continued

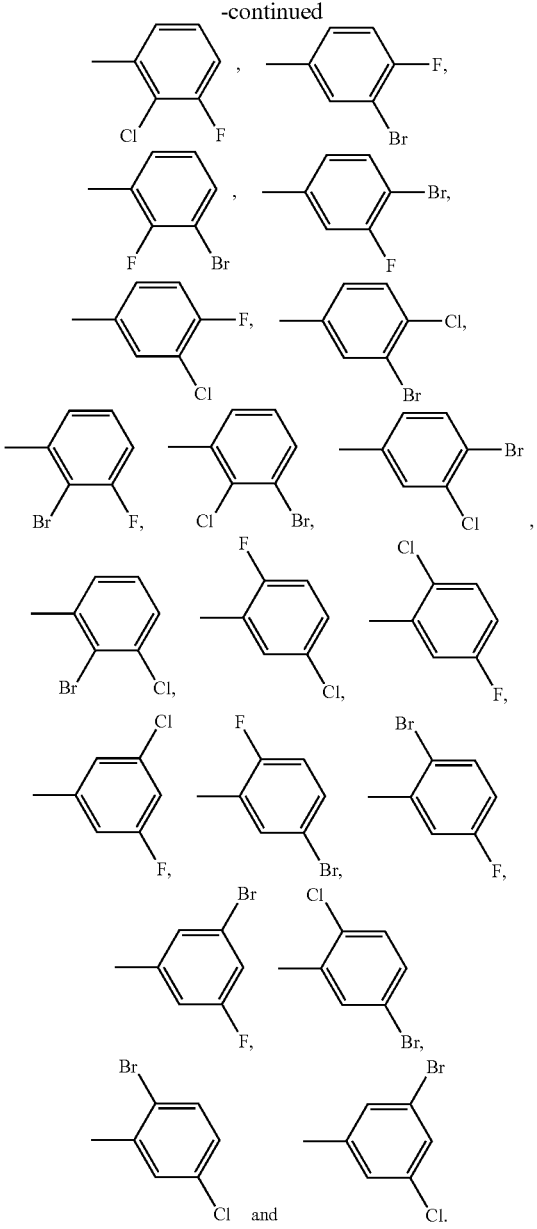

In another embodiment of a spiroheterocyclic amido alkyloxy substituted quinazoline derivative and pharmaceutically acceptable salts thereof, the active ingredients of the compounds are as represented by Formula II-III:

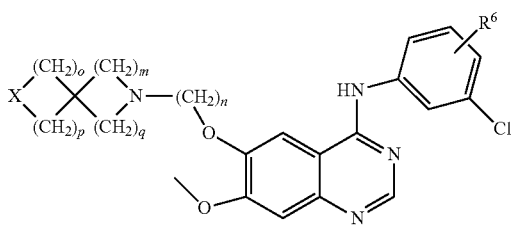

Formula II-III wherein m, o, p and q are each independently selected from integer that is greater than or equals to zero, preferably selected the integer from 0 to 6, e.g. 0, 1, 2, 3, 4, 5, and 6; and more preferably selected the integer from 0 to 4; n is selected from integer that is larger than or equal to 2, preferably selected the integers from 2 to 4, e.g. 2, 3 and 4;

group X is selected from atom O, atom S, or one of the following groups:

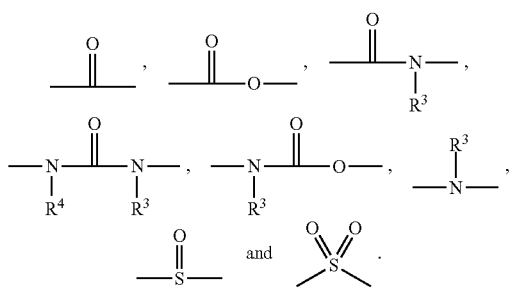

group $R^3$ and group $R^4$ are respectively and independently selected from one of hydrogen, acyl, sulfonyl, substituted or unsubstituted C1-C6 alkyl, substituted or unsubstituted C3-C7 cycloalkyl, substituted or unsubstituted phenyl, and substituted or unsubstituted aromatic heterocyclyl.

$R^6$ is one of fluorine, chlorine, bromine, cyano and ethynyl.

In another embodiment of a spiroheterocyclic amino alkyloxy substituted quinazoline derivative and pharmaceutically acceptable salts thereof, the active ingredients of the compounds are as represented by Formula II-IV:

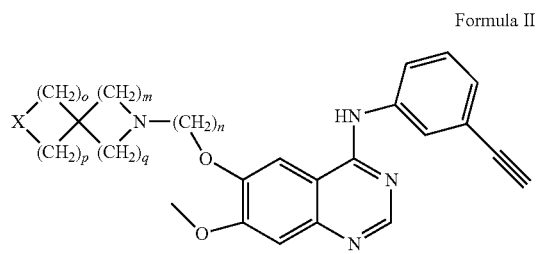

Formula II-IV wherein m, o, p and q are each independently selected from integer that is greater than or equals to zero, preferably selected the integer from 0 to 6, e.g. 0, 1, 2, 3, 4, 5, and 6; and more preferably selected the integer from 0 to 4; n is selected from integer that is larger than or equal to 2, preferably selected the integers from 2 to 4, e.g. 2, 3 and 4;

group X is selected from atom O, atom S, or one of the following groups:

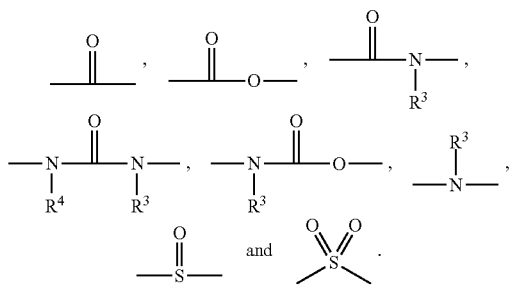

Group $R^3$ and group $R^4$ are respectively and independently selected from one of hydrogen, acyl, sulfonyl, substituted or unsubstituted C1-C6 alkyl, substituted or unsubstituted C3-C7 cycloalkyl, substituted or unsubstituted phenyl, and substituted or unsubstituted aromatic heterocyclyl.

In another embodiment of a spiroheterocyclic amino alkyloxy substituted quinazoline derivative and pharmaceutically acceptable salts thereof, the active ingredients of the compounds are as represented by Formula II-V:

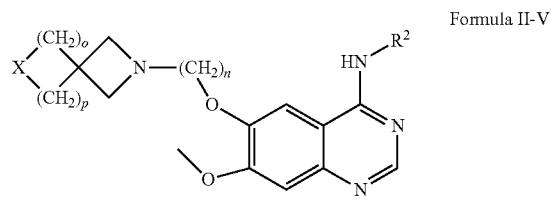

Formula II-V wherein o and p are each independently selected the integer from 0, 1, 2 or 3, n is selected from integer that is larger than or equal to 2, preferably selected the integer from 2 to 4, e.g. 2, 3 and 4; and group X is selected from atom O, atom S, or one of the following groups:

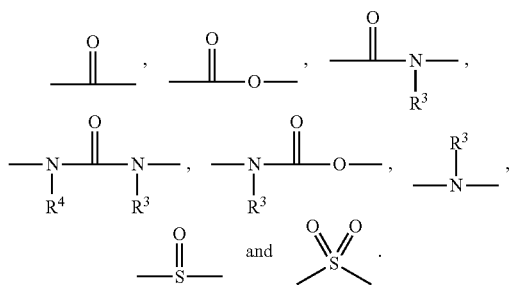

Group $R^3$ and group $R^4$ are respectively and independently selected from one of hydrogen, acyl, sulfonyl, substituted or unsubstituted C1-C6 alkyl, substituted or unsubstituted C3-C7 cycloalkyl, substituted or unsubstituted phenyl, and substituted or unsubstituted aromatic heterocyclyl.

Group $R^2$ is substituted or unsubstituted phenyl or substituted or unsubstituted aromatic heterocyclyl, preferably selected form the group of phenyl substituted by one or several from halogen, cyano, alkyl, alkenyl and alkynyl, or aromatic heterocyclyl substituted by one or several from halogen, cyano, alkyl, alkenyl and alkynyl; and the more preferred group is

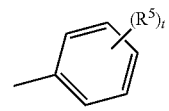

wherein t equals to 1 or 2, each group $R^5$, which may be same or different, is independently from fluorine, chlorine, bromine, cyano, and C2-C4 alkynyl, and the group

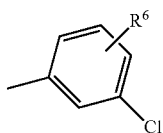

wherein R⁶ is one from fluorine, chlorine, bromine, cyano and alkynyl, and the group

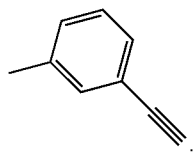

In another embodiment of a spiroheterocyclic amino alkyloxy substituted quinazoline derivative and pharmaceutically acceptable salts thereof, the active ingredients of the compounds are as represented by Formula II-VI:

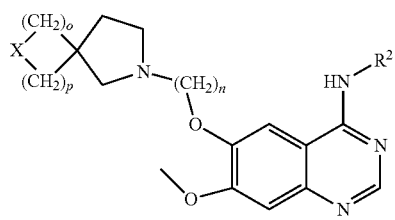

Formula II-VI wherein o and p are each independently selected the integer from 0, 1, 2 or 3, n is selected from integer that is larger than or equal to 2, preferably selected the integer from 2 to 4, e.g. 2, 3 and 4; and Group X is selected from atom O, atom S, or one of the following groups:

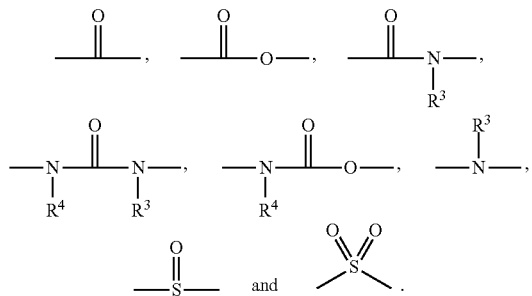

group $R^3$ and group $R^4$ are respectively and independently selected from one of hydrogen, acyl, sulfonyl, substituted or unsubstituted C1-C6 alkyl, substituted or unsubstituted C3-C7 cycloalkyl, substituted or unsubstituted phenyl, and substituted or unsubstituted aromatic heterocyclyl.

group $R^2$ is substituted or unsubstituted phenyl or substituted or unsubstituted aromatic heterocyclyl, preferably selected form the group of phenyl substituted by one or several from halogen, cyano, alkyl, alkenyl and alkynyl, or aromatic heterocyclyl substituted by one or several from halogen, cyano, alkyl, alkenyl and alkynyl; and the more preferred group is

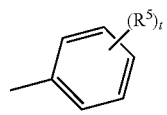

wherein t equals to 1 or 2, each group $R^5$, which may be same or different, is independently from fluorine, chlorine, bromine, cyano, and C2-C4 alkynyl, and the group

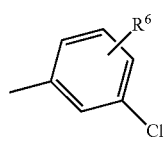

wherein $R^6$ is one from fluorine, chlorine, bromine, cyano and alkynyl, and the group

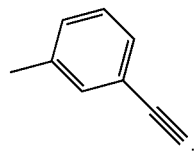

In another embodiment of a bridged heterocycle amino alkyloxy substituted quinazoline derivative, pharmaceutically acceptable salts and its hydrate thereof, the active ingredients of the compounds are as represented by Formula III-I:

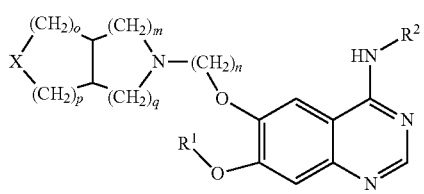

Formula III-I wherein m, o, p and q are each independently selected from integer that is greater than or equals to zero, preferably selected the integer from 0 to 6, e.g. 0, 1, 2, 3, 4, 5, and 6; and more preferably selected the integer from 0 to 4; n is selected from integer that is larger than or equal to 2, preferably selected the integer from 2 to 4, e.g. 2, 3 and 4; and Group X is selected from atom O, atom S, or one of the following group:

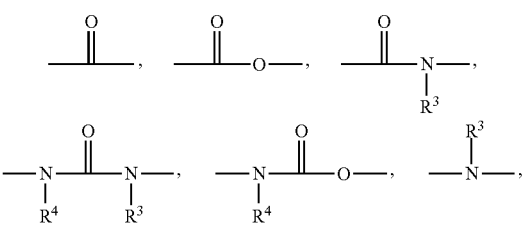

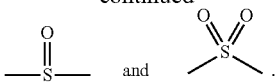

group R³ and group R⁴ are respectively and independently selected from one of hydrogen, acyl, sulfonyl, substituted or unsubstituted C1-C6 alkyl, substituted or unsubstituted C3-C7 cycloalkyl, substituted or unsubstituted phenyl, and substituted or unsubstituted aromatic heterocyclyl.

Group R¹ is substituted or unsubstituted C1-C8 alkyl or substituted or unsubstituted C3-C7 cycloalkyl, preferably selected form the group of methyl, deuterated methyl, ethyl, deuterated ethyl, trifluoromethyl, methoxyethyl, cyclopropyl or cyclopropyl methyl.

Group R² is substituted or unsubstituted phenyl or substituted or unsubstituted aromatic heterocyclyl, preferably selected form the group of phenyl substituted by one or several from halogen, cyano, alkyl, alkenyl and alkynyl, or aromatic heterocyclyl substituted by one or several from halogen, cyano, alkyl, alkenyl and alkynyl; and the more preferred group is

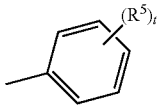

wherein t equals to 1 or 2, each group R⁵, which may be same or different, is independently from fluorine, chlorine, bromine, cyano, and C2-C4 alkynyl, and the group

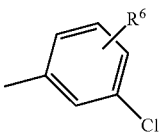

wherein R⁶ is one from fluorine, chlorine, bromine, cyano and alkynyl, and the group

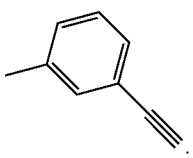

In another preferred embodiment of a bridged heterocycle amino alkyloxy substituted quinazoline derivative, pharmaceutically acceptable salts and its hydrate thereof, the active ingredients of the compounds are as represented by Formula III-II:

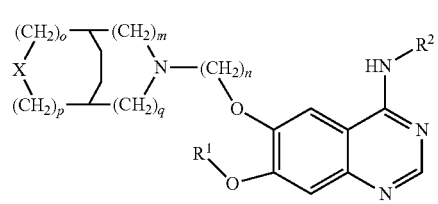

Formula III-II wherein m, o, p and q are each independently selected from integer that is greater than or equals to zero, preferably selected the integer from 0 to 6, e.g. 0, 1, 2, 3, 4, 5, and 6; and more preferably selected the integer from 0 to 4; n is selected from integer that is larger than or equal to 2, preferably selected the integers from 2 to 4, e.g. 2, 3 and 4; and group X is selected from atoms O, atom S, or one of the following groups:

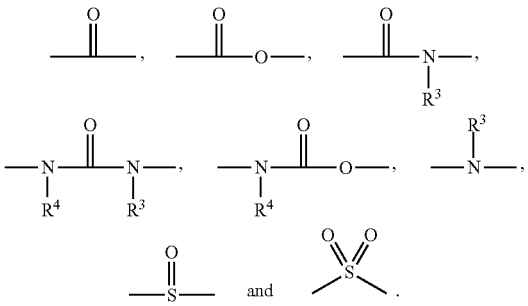

Group R³ and group R⁴ are respectively and independently selected from one of hydrogen, acyl, sulfonyl, substituted or unsubstituted C1-C6 alkyl, substituted or unsubstituted C3-C7 cycloalkyl, substituted or unsubstituted phenyl, and substituted or unsubstituted aromatic heterocyclyl.

Group R¹ is substituted or unsubstituted C1-C8 alkyl or substituted or unsubstituted C3-C7 cycloalkyl, preferably selected form the group of methyl, deuterated methyl, ethyl, deuterated ethyl, trifluoromethyl, methoxyethyl, cyclopropyl or cyclopropyl methyl.

Group R² is substituted or unsubstituted phenyl or substituted or unsubstituted aromatic heterocyclyl, preferably selected form the group of phenyl substituted by one or several from halogen, cyano, alkyl, alkenyl and alkynyl, or aromatic heterocyclyl substituted by one or several from halogen, cyano, alkyl, alkenyl and alkynyl; and the more preferred group is

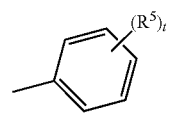

wherein t equals to 1 or 2, each group R⁵, which may be same or different, is independently from fluorine, chlorine, bromine, cyano, C1-C4 alkyl and C2-C4 alkynyl, and the group

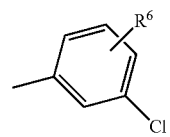

wherein R⁶ is one from fluorine, chlorine, bromine, cyano and alkynyl, and the group

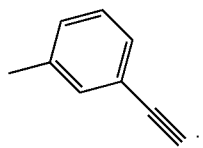

According to the understanding of a skilled person in the art, since one or more asymmetric carbon atoms can be formed, certain of the compounds set forth as Formula I, Formula II-, Formula II-, Formula II-III, Formula II-, Formula II-, Formula II-VI, Formula III- and Formula III-II of the invention, will present the optically active or racemic forms, or the geometrical isomers (e.g. E- and Z-isomer). Therefore, the Formulas described herein also include the optically active or racemic forms, or the geometrical isomers. These optically active or racemic forms can be produced by synthesis with optical rotation raw materials, by biotransformation, or by separation using a separation column.

The various heterocycle amino alkyloxy substituted quinazoline derivatives and pharmaceutically acceptable salts of the present invention, as well as pharmaceutical composition produced by all kinds of pharmaceutic adjuvants, addition agents or carriers in favor of the pharmaceutical composition administered, such as, but not limited to aqueous solution injection, powder injection, pills, pulvis, tablets, patches, suppository, emulsion, crime, gels, granular formulation, capsule, aerosol, spraying agent, powder spray, sustained release, controlled release formulations, and the like. These pharmaceutic adjuvants not only can usually be used in all kinds of formulations such as, but not limited to one or any combination of, isotonic agent, buffer solution, flavoring agent, antiseptic, bacteriostatic agent, excipient, loading agent, adhesive, disintegrant, lubricant and etc., but also selected in order to adapt with the choice of the material used, such as emulsifier, solubilizer, bacteriostatic agent, analgetic, antioxidant and etc. Such kind of adjuvants can effectively enhance stability and solubility of compounds contained in composition or alter release and absorption rate of compounds, thus improving metabolism of compounds of the invention in vivo and strengthening drug effect. Additionally, adjuvants, such as, but not limited to gelatin, albumin, chitosan, polyether and polyester polymers which are such as, but not limited to polyoxyethylene, polyurethane, polycarbonate and copolymers can be used to achieve a particular purpose or mode of administration, such as sustained release, controlled release and pulsed release. The main performance of the said "in favor of administration" includes, but not limited to, improved treatment effect and bioavailability, lower toxic and side effects, and higher patient adaptability. Pharmaceutic adjuvants, addition agents or carriers may vary from about 5% to about 99% by weight of the total pharmaceutical composition.

A pharmaceutical composition containing, by weight, 1%-95% active ingredients of a heterocycle amino alkyloxy substituted quinazoline derivative and pharmaceutically acceptable salt thereof of the present invention was administered to a subject. The effective dosage of the active ingredients was confirmed according to the body weight, or according to the actual situation of the organisms and disease thereof. The times and dosage could also be adjusted, such as twice or more per day. According to the formulation, the effective therapeutic dosage administrated would still be different.

The present invention provides a pharmaceutical composition including one or several of the following compounds and pharmaceutically acceptable salts thereof as active ingredients:

Compound 1: 4-(3'-chloro-4'-fluorophenylamino)-6-[3-(2-oxa-6-azaspiro[3.3]heptane-6-yl)-propoxy]-7-methoxyquinazoline Compound 2: 4-(3'-chloro-4'-fluorophenylamino)-6-[3-(2-oxa-6-azaspiro[3.4]octane-6-yl)-propoxy]-7-methoxyquinazoline Compound 3: 4-(3'-chloro-4'-fluorophenylamino)-6-[2-(2-oxa-6-azaspiro[3.4]octane-6-yl)-oxethyl]-7-methoxyquinazoline Compound 4: 4-(3'-chloro-4'-fluorophenylamino)-6-[3-(7-oxa-2-azaspiro[3.5]nonane-2-yl)-propoxy]-7-methoxyquinazoline Compound 5: 4-(3'-chloro-4'-fluorophenylamino)-6-[3-(2-oxa-7-azaspiro[3.5]nonane-7-yl)-propoxy]-7-methoxyquinazoline Compound 6: 4-(3'-chloro-4'-fluorophenylamino)-6-[2-(7-oxa-2-azaspiro[3.5]nonane-2-yl)-oxethyl]-7-methoxyquinazoline Compound 7: 4-(3'-chloro-4'-fluorophenylamino)-6-[3-(2-oxa-7-azaspiro[4.4]nonane-7-yl)-propoxy]-7-methoxyquinazoline Compound 8: 4-(3'-chloro-4'-fluorophenylamino)-6-[2-(2-oxa-7-azaspiro[4.4]nonane-7-yl)-oxethyl]-7-methoxyquinazoline Compound 9: 4-(3'-chloro-4'-fluorophenylamino)-6-[3-(8-oxa-2-azaspiro[4.5]decane-2-yl)-propoxy]-7-methoxyquinazoline Compound 10: 4-(3'-chloro-4'-fluorophenylamino)-6-[2-(8-oxa-2-azaspiro[4.5]decane-2-yl)-oxethyl]-7-methoxyquinazoline Compound 11: 4-(3'-chloro-4'-fluorophenylamino)-6-[2-(8-oxa-3-azabicyclo[3.2.1]octane-3-yl)-oxethyl]-7-methoxyquinazoline Compound 12: 4-(3'-chloro-4'-fluorophenylamino)-6-[3-(8-oxa-3-azabicyclo[3.2.1]octane-3-yl)-propoxy]-7-methoxyquinazoline Compound 13: 4-(3'-chloro-4'-fluorophenylamino)-6-[2-(3-oxa-8-azabicyclo[3.2.1]octane-8-yl)-oxethyl]-7-methoxyquinazoline Compound 14: 4-(5'-chloro-2'-fluorophenylamino)-6-[3-(2-oxa-6-azaspiro[3.3]heptane-6-yl)-propoxy]-7-methoxyquinazoline Compound 15: 4-(5'-chloro-2'-fluorophenylamino)-6-[3-(2-oxa-7-azaspiro[4.4]nonane-7-yl)-propoxy]-7-methoxyquinazoline Compound 16: 4-(5'-chloro-2'-fluorophenylamino)-6-[3-(3-oxa-8-azabicyclo[3.2.1]octane-8-yl)-propoxy]-7-methoxyquinazoline Compound 17: 4-(3'-chloro-4'-fluorophenylamino)-6-[3-(8-oxa-2-azaspiro[4.5]decane-2-yl)-propoxy]-7-methoxyquinazoline Compound 18: 4-(5'-chloro-2'-fluorophenylamino)-6-[3-(7-oxa-2-azaspiro[3.5]-nonane-2-yl)-propoxy]-7-methoxyquinazoline Compound 19: 4-(5'-chloro-2'-fluorophenylamino)-6-[3-(7-acetyl-2,7-diazaspiro[4.4]-nonane-2-yl)-propoxy]-7-methoxyquinazoline Compound 20: 4-(5'-chloro-2'-fluorophenylamino)-6-[3-(cis-hexahydrofuro[3,2-b]pyrrole-4-yl)-propoxy]-7-methoxyquinazoline Compound 21: 4-(5'-chloro-2'-fluorophenylamino)-6-[3-(2,8-diazaspiro[4.5]decyl-3-ketone-8-yl)-propoxy]-7-methoxyquinazoline Compound 22: 4-(5'-chloro-2'-fluorophenylamino)-6-[3-(2,7-diazaspiro[4.4]nonane-1-ketone-7-yl)-propoxy]-7-methoxyquinazoline Compound 23: 4-(5'-chloro-2'-fluorophenylamino)-6-[3-(2-methyl-2,7-diazaspiro[4.4]nonane-1-ketone-7-yl)-propoxy]-7-methoxyquinazoline Compound 24: 4-(5'-chloro-2'-fluorophenylamino)-6-[3-(2-methyl-2,8-diazaspiro[4.5]decane-3-ketone-8-yl)-propoxy]-7-methoxyquinazoline Compound 25: 4-(5'-chloro-2'-fluorophenylamino)-6-[3-(1,8-diazaspiro[4.5]decane-2-ketone-8-yl)-propoxy]-7-methoxyquinazoline Compound 26: 4-(5'-chloro-2'-fluorophenylamino)-6-[3-(2-methyl-2,8-diazaspiro[4.5]decane-1-ketone-8-yl)-propoxy]-7-methoxyquinazoline Compound 27: 4-(5'-chloro-2'-fluorophenylamino)-6-[3-(2,6-diazaspiro[3.4]octane-7-ketone-2-yl)]-propoxy]-7-methoxyquinazoline Compound 28: 4-(3'-chloro-2'-fluorophenylamino)-6-[3-(2-oxa-6-azaspiro[3.4]octane-6-yl)-propoxy]-7-methoxyquinazoline Compound 29: 4-(3'-chloro-2'-fluorophenylamino)-6-[3-(2,7-diazaspiro[4.4]nonane-1-ketone-7-yl)-propoxy]-7-methoxyquinazoline Compound 30: 4-(3'-chloro-2'-fluorophenylamino)-6-[3-(2-methyl-2,7-diazaspiro[4.4]nonane-1-ketone-7-yl)-propoxy]-7-methoxyquinazoline Compound 31: 4-(3'-chloro-2'-fluorophenylamino)-6-[3-(2-methyl-2,8-diazaspiro[4.5]decane-3-ketone-8-yl)-propoxy]-7-methoxyquinazoline Compound 32: 4-(3'-chloro-2'-fluorophenylamino)-6-[3-(1,8-diazaspiro[4.5]decane-2-ketone-8-yl)-propoxy]-7-methoxyquinazoline Compound 33: 4-(3'-chloro-2'-fluorophenylamino)-6-[3-(2,6-diazaspiro[3.4]octane-7-ketone-2-yl)]-propoxy]-7-methoxyquinazoline Compound 34: 4-(3'-chloro-2'-fluorophenylamino)-6-[3-(1-oxa-3,8-diazaspiro[4.5]decane-2-ketone-8-yl)-propoxy]-7-methoxyquinazoline Compound 35: 4-(3'-chloro-2'-fluorophenylamino)-6-[3-(3-methyl-1-oxa-3,7-diazaspiro[4.4]nonane-2-ketone-7-yl)-propoxy]-7-methoxyquinazoline Compound 36: 4-(3'-chloro-2'-fluorophenylamino)-6-[3-(5-oxa-2,7-diazaspiro[3.4]octane-6-ketone-2-yl)-propoxy]-7-methoxyquinazoline Compound 37: 4-(3'-chloro-2'-fluorophenylamino)-6-[3-(7-methyl-5-oxa-2,7-diazaspiro[3.4]octane-6-ketone-2-yl)-propoxy]-7-methoxyquinazoline Compound 38: 4-(3'-ethynylphenylamino)-6-[3-(2-oxa-6-azaspiro[3.3]heptane-6-yl)-propoxy]-7-methoxyquinazoline Compound 39: 4-(3'-ethynylphenylamino)-6-[3-(7-oxa-2-azaspiro[3.5]nonane-2-yl)-propoxy]-7-methoxyquinazoline Compound 40: 4-(3'-ethynylphenylamino)-6-[3-(2-oxa-7-azaspiro[4.4]-nonane-7-yl)-propoxy]-7-methoxyquinazoline Compound 41: 4-(3'-ethynylphenylamino)-6-[3-(8-oxa-2-azaspiro[4.5]decane-2-yl)-propoxy]-7-methoxyquinazoline Compound 42: 4-(3'-ethynylphenylamino)-6-[3-(3-oxa-8-azabicyclo[3.2.1]octane-8-yl)-propoxy]-7-methoxyquinazoline Compound 43: 4-(3'-ethynylphenylamino)-6-[3-(2,8-diazaspiro[4.5]decane-3-ketone-8-yl)-propoxy]-7-methoxyquinazoline Compound 44: 4-(3'-ethynylphenylamino)-6-[3-(2-methyl-2,8-diazaspiro[4.5]decane-3-ketone-8-yl)propoxy]-7-methoxyquinazoline Compound 45: 4-(3'-ethynylphenylamino)-6-[3-(2,6-diazaspiro[3.4]octane-7-ketone-2-yl)-propoxy]-7-methoxyquinazoline Compound 46: 4-(3'-ethynylphenylamino)-6-[3-(1-oxa-3,8-diazaspiro[4.5]decane-2-ketone-8-yl)-propoxy]-7-methoxyquinazoline Compound 47: 4-(3'-ethynylphenylamino)-6-[3-(3-methyl-1-oxa-3,7-diazaspiro[4.4]nonane-2-ketone-7-yl)-propoxy]-7-methoxyquinazoline Compound 48: 4-(3'-ethynylphenylamino)-6-[3-[(5-oxa-2,7-diazaspiro[3.4]octane-6-ketone-2-yl)-propoxy]-7-methoxyquinazoline Compound 49: 4-(3'-ethynylphenylamino)-6-[3-[(7-methyl-5-oxa-2,7-diazaspiro[3.4]octane-6-ketone-2-yl)-propoxy]-7-methoxyquinazoline Compound 50: 4-(3'-ethynylphenylamino)-6-[3-(cis-hexahydrofuro[3,2-b]pyrrole-4-yl)-propoxy]-7-methoxyquinazoline Compound 51: 4-(3'-ethynylphenylamino)-6-[3-(7-acetyl-2,7-diazaspiro[4.4]-nonane-2-yl)-propoxy]-7-methoxyquinazoline Compound 52: 4-(3'-chloro-4'-fluorophenylamino)-6-[2-(7-methyl-2,7-diazaspiro[4.4]nonane-2-yl)-oxethyl]-7-methoxyquinazoline Compound 53: 4-(3'-chloro-4'-fluorophenylamino)-6-[3-(7-oxa-2-azaspiro[3.5]nonane-2-yl)-oxethyl]-7-methoxyquinazoline Compound 54: 4-(3'-chloro-4'-fluorophenylamino)-)-6-[3-(cis-hexahydrofuro[3,2-b]pyrrole-4-yl)-propoxy]-7-methoxyquinazoline Compound 55: 4-(3'-chloro-4'-fluorophenylamino)-6-[2-(2,7-diazaspiro[4.4]-nonane-1-ketone-7-yl)-oxethyl]-7-methoxyquinazoline Compound 56: 4-(3'-chloro-4'-fluorophenylamino)-6-[2-(2-methyl-2,8-diazaspiro[4.5]decane-2-ketone-8-yl)-oxethyl]-7-methoxyquinazoline Compound 57: 4-(3'-chloro-4'-fluorophenylamino)-6-[2-(2,6-diazaspiro[3.4]octane-7-ketone-2-yl)-oxethyl]-7-methoxyquinazoline Compound 58: 4-(3'-chloro-4'-fluorophenylamino)-6-[2-(1-oxa-3,8-diazaspiro[4.5]decane-2-ketone-8-yl)-oxethyl]-7-methoxyquinazoline Compound 59: 4-(3'-chloro-4'-fluorophenylamino)-6-[2-(3-methyl-1-oxa-3,7-diazaspiro[4.4]nonane-2-ketone-7-yl)-oxethyl]-7-methoxyquinazoline Compound 60: 4-(3'-chloro-4'-fluorophenylamino)-6-[2-(5-oxa-2,7-diazaspiro[3.4]octane-6-ketone-2-yl)-oxethyl]-7-methoxyquinazoline Compound 61: 4-(3'-chloro-4'-fluorophenylamino)-6-[2-(7-methyl-5-oxa-2,7-diazaspiro[3.4]octane-6-ketone-2-yl)-oxethyl]-7-methoxyquinazoline Compound 62: 4-(3'-chloro-4'-fluorophenylamino)-6-[2-(2-oxa-6-azaspiro[3.3]heptane-6-yl)-oxethyl]-7-methoxyquinazoline Compound 63: 4-(3'-chloro-4'-fluorophenylamino)-6-[2-(2,8-diazaspiro[4.5]decane-3-ketone-8-yl)-oxethyl]-7-methoxyquinazoline Compound 64: 4-(5'-chloro-2'-fluorophenylamino)-6-[3-(7-methyl-2,7-diazaspiro[4.4]nonane-2-yl)-propoxy]-7-methoxyquinazoline Compound 65: 4-(5'-chloro-2'-fluorophenylamino)-6-[3-(2-oxa-6-azaspiro[3.4]octane-6-yl)-propoxy-7-methoxyquinazoline Compound 66: 4-(5'-chloro-2'-fluorophenylamino)-6-[3-(2,8-diazaspiro[4.5]-decane-3-ketone-8-yl)-propoxy]-7-methoxyquinazoline Compound 67: 4-(5'-chloro-2'-fluorophenylamino)-6-[3-(7-methyl-2,7-diazaspiro[4.4]-nonane-2-yl)-propoxy]-7-methoxyquinazoline Compound 68: 4-(3'-ethynylphenylamino)-6-[3-(7-methyl-2,7-diazaspiro[4.4]nonyl)-propoxy]-7-methoxyquinazoline Compound 69: 4-(3'-ethynylphenylamino)-6-[3-(2,8-diazaspiro[4.5]decane-3-ketone-8-yl)-propoxy]-7-methoxyquinazoline Compound 70: 4-(3'-ethynylphenylamino)-6-[3-(2,7-diazaspiro[4.4]-nonane-1-ketone-7-yl)-propoxy]-7-methoxyquinazoline Compound 71: 4-(3'-ethynylphenylamino)-6-[3-(2-methyl-2,7-diazaspiro[4.4]-nonane-1-ketone-7-yl)-propoxy]-7-methoxyquinazoline Compound 72: 4-(3'-ethynylphenylamino)-6-[3-(2,8-diazaspiro[4.5]decane-1-ketone-8-yl)-propoxy]-7-methoxyquinazoline Compound 73: 4-(3'-ethynylphenylamino)-6-[3-(2-methyl-2,8-diazaspiro[4.5]decane-3-ketone-8-yl)-propoxy]-7-methoxyquinazoline Compound 74: 4-(3'-ethynylphenylamino)-6-[3-(1,8-diazaspiro[4.5]decane-2-ketone-8-yl)-propoxy]-7-methoxyquinazoline Compound 75: 4-(3'-ethynylphenylamino)-6-[3-(2-oxa-6-azaspiro[3.4]octane-6-yl)-propoxy]-7-methoxyquinazoline Compound 76: 4-(3'-chloro-4'-fluorophenylamino)-6-[3-(7-methyl-2,7-diazaspiro[4.4]nonane-2-yl)-propoxy]-7-methoxyquinazoline Compound 77: 4-(3'-chloro-4'-fluorophenylamino)-6-[3-(7-tertbutyloxycarbonyl-2,7-diazaspiro[4.5]decane-2-yl)-propoxy]-7-methoxyquinazoline Compound 78: 4-(3'-chloro-4'-fluorophenylamino)-6-[3-(cis-hexahydrofuro[3,2-b]pyrrole-4-yl)-propoxy]-7-methoxyquinazoline Compound 79: 4-(3'-chloro-4'-fluorophenylamino)-6-[3-(3,8-diazaspiro[4,5]-decyl-2-ketone)-propoxy-7-methoxyquinazoline Compound 80: 4-(3'-chloro-4'-fluorophenylamino)-6-[3-(2,7-diazaspiro[4.4]-nonane-1-ketone-7-yl)-propoxy]-7-methoxyquinazoline Compound 81: 4-(3'-chloro-4'-fluorophenylamino)-6-[3-(2-methyl-2,7-diazaspiro[4.4]-nonane-1-ketone-7-yl)-propoxy]-7-methoxyquinazoline Compound 82: 4-(3'-chloro-4'-fluorophenylamino)-6-[3-(2,8-diazaspiro[4.5]decane-1-ketone-8-yl)-propoxy]-7-methoxyquinazoline Compound 83: 4-(3'-chloro-4'-fluorophenylamino)-6-[3-(2-methyl-2,8-diazaspiro[4.5]decane-3-ketone-8-yl)-propoxy]-7-methoxyquinazoline Compound 84: 4-(3'-chloro-4'-fluorophenylamino)-6-[3-(1,8-diazaspiro[4.5]decane-2-ketone-8-yl)-propoxy]-7-methoxyquinazoline Compound 85: 4-(3'-chloro-4'-fluorophenylamino)-6-[3-(2-methyl-2,8-diazaspiro[4.5]decane-1-ketone-8-yl)]-propoxy]-7-methoxyquinazoline Compound 86: 4-(3'-chloro-4'-fluorophenylamino)-6-[3-(2,6-diazaspiro[3.4]octane-7-ketone-2-yl)-propoxy]-7-methoxyquinazoline Compound 87: 4-(3'-chloro-4'-fluorophenylamino)-6-[3-(1-oxa-3,8-diazaspiro[4.5]decane-2-ketone-8-yl)-propoxy]-7-methoxyquinazoline Compound 88: 4-(3'-chloro-4'-fluorophenylamino)-6-[3-(5-tertbutyloxycarbonyl-hexahydropyrrolo[3,4-c]pyrrole-2-yl)-propoxy]-7-methoxyquinazoline Compound 89: 4-(3'-chloro-4'-fluorophenylamino)-6-[3-[3-methyl-1-oxa-3,7-diazaspiro[4.4]nonane-2-ketone-7-yl)-propoxy]-7-methoxyquinazoline Compound 90: 4-(3'-chloro-4'-fluorophenylamino)-6-[3-(5-oxa-2,7-diazaspiro[3.4]octane-6-ketone-2-yl)-propoxy]-7-methoxyquinazoline Compound 91: 4-(3'-chloro-4'-fluorophenylamino)-6-[3-(7-methyl-5-oxa-2,7-diazaspiro[3.4]octane-6-ketone-2-yl)-propoxy]-7-methoxyquinazoline Compound 92: 4-(3'-chloro-4'-fluorophenylamino)-6-[3-(7-acetyl-2,7-diazaspiro[4.4]-nonane-2-yl)-propoxy]-7-methoxyquinazoline Compound 93: 4-(3'-chloro-4'-fluorophenylamino)-6-[3-(8-oxa-3-aza-azabicyclo[3.2.1]octane-3-yl)-propoxy]-7-methoxyquinazoline Compound 94: 4-(3'-chloro-4'-fluorophenylamino)-6-[3-(2,8-diazaspiro[4.5]decane-3-ketone-8-yl)-propoxy]-7-methoxyquinazoline Compound 95: 4-(3'-chloro-4'-fluorophenylamino)-6-[3-(1-oxa-3,8-diazaspiro[4.5]decane-2-ketone-8-yl)-propoxy]-7-deuterated methoxyquinazoline Compound 96: 4-(3'-chloro-4'-fluorophenylamino)-6-[3-(3-methyl-1-oxa-3,7-diazaspiro[4.4]nonane-2-ketone-7-yl)-propoxy]-7-deuterated methoxyquinazoline Compound 97: 4-(3'-chloro-4'-fluorophenylamino)-6-[3-(5-oxa-2,7-diazaspiro[3.4]octane-6-ketone-2-yl)-propoxy]-7-deuterated methoxyquinazoline Compound 98: 4-(3'-chloro-4'-fluorophenylamino)-6-[3-(7-methyl-5-oxa-2,7-diazaspiro[3.4]octane-6-ketone-2-yl)-propoxy]-7-deuterated methoxyquinazoline Compound 99: 4-(3'-chloro-4'-fluorophenylamino)-6-[3-(2-oxa-6-azaspiro[3.4]octane-6-yl)-propoxy]-7-deuterated methoxyquinazoline Compound 100: 4-(3'-chloro-2'-fluorophenylamino)-6-[3-(1-oxa-3,8-diazaspiro[4.5]decane-2-ketone-8-yl)-propoxy]-7-methoxyquinazoline Compound 101: 4-(3'-chloro-2'-fluorophenylamino)-6-[3-(3-methyl-1-oxa-3,7-diazaspiro[4.4]nonane-2-ketone-7-yl)-propoxy]-7-methoxyquinazoline Compound 102: 4-(3'-chloro-2'-fluorophenylamino)-6-[3-(5-oxa-2,7-diazaspiro[3.4]octane-6-ketone-2-yl)-propoxy]-7-methoxyquinazoline Compound 103: 4-(5'-chloro-2'-fluorophenylamino)-6-[3-(7-methyl-5-oxa-2,7-diazaspiro[3.4]octane-6-ketone-2-yl)-propoxy]-7-methoxyquinazoline Compound 104: 4-(3'-chloro-4'-fluorophenylamino)-6-[3-(5-oxa-2-azaspiro[3.4]octane-6-ketone-2-yl)-propoxy]-7-methoxyquinazoline Compound 105: 4-(3'-chloro-4'-fluorophenylamino)-6-[3-(6-oxa-2-azaspiro[3.4]octane-7-ketone-2-yl)-propoxy]-7-methoxyquinazoline Compound 106: 4-(3'-chloro-4'-fluorophenylamino)-6-[3-(6,6-dioxo-6-thia-2-azaspiro[3.4]octane-2-yl)propoxy]-7-methoxyquinazoline Compound 107: 4-(5'-chloro-2'-fluorophenylamino)-6-[3-(6,6-dioxo-6-thia-2-azaspiro[3.4]octane-2-yl)propoxy]-7-methoxyquinazoline Compound 108: 4-(3'-chloro-2'-fluorophenylamino)-6-[3-(6,6-dioxo-6-thia-2-azaspiro[3.4]octane-2-yl)propoxy]-7-methoxyquinazoline Compound 109: 4-(3'-ethynylphenylamino)-6-[3-(6,6-dioxo-6-thia-2-azaspiro[3.4]octane-2-yl)propoxy]-7-methoxyquinazoline Compound 110: 4-(3'-ethynylphenylamino)-6-[3-(hexahydropyrrolo[3,4-b]pyrrole-1-yl)-propoxy]-7-methoxyquinazoline Compound 111: 4-(3'-chloro-2'-fluorophenylamino)-6-[3-(cis-hexahydropyrrolo[3,4-b]pyrrole-1-yl)-propoxy]-7-methoxyquinazoline Compound 112: 4-(3'-chloro-2'-fluorophenylamino)-6-[3-(cis-octahydropyrrol[3,2-c]pyrrole-1-yl)-propoxy]-7-methoxyquinazoline Compound 113: 4-(3'-chloro-2'-fluorophenylamino)-6-[3-(cis-octahydropyrrolo[3,4-c]azepine-2-yl)-propoxy]-7-methoxyquinazoline hydrochloride Compound 114: 4-(3'-chloro-2'-fluorophenylamino)-6-[3-(5-tertbutyloxycarbonyl-cis-octahydropyrrolo[3,4-c]pyrrole-2-yl)-propoxy]-7-methoxyquinazoline Compound 115: 4-(3'-chloro-2'-fluorophenylamino)-6-[3-(5-oxa-2-azaspiro[3.4]octane-6-ketone-2-yl)-propoxy]-7-methoxyquinazoline Compound 116: 4-(3'-chloro-2'-fluorophenylamino)-6-[3-(6-oxa-2-azaspiro[3.4]octane-7-ketone-2-yl)-propoxy]-7-methoxyquinazoline Compound 117: 4-(3'-ethynylphenylamino)-6-[3-(5-oxa-2-azaspiro[3.4]octane-6-ketone-2-yl)-propoxy]-7-methoxyquinazoline Compound 118: 4-(3'-ethynylphenylamino)-6-[3-(6-oxa-2-azaspiro[3.4]octane-7-ketone-2-yl)-propoxy]-7-methoxyquinazoline All kinds of heterocycle amido alkyloxy substituted quinazoline derivative and pharmaceutically acceptable salts provided in the invention as well as various drugs made from heterocycle amido alkyloxy substituted quinazoline derivatives and pharmaceutically acceptable salts can inhibit receptor tyrosine kinase EGFR of ErbB family. Besides, they can also inhibit Her2, Her3, Her4 and other receptor tyrosine kinase related to cancer, such as Vascular-endothelial Growth Factor Receptor (VEGFR), Fibroblast Growth Factor Receptor (FGFR), Platelet-derived Growth Factor Receptor (PDGFR), Insulin and insulin-like Growth Factor-1 Receptor (IGF-1R), and Hepatocyte Growth Factor Receptor (HGFR or c-MET), and reduce the phosphorylation of these tyrosine kinases on tyrosine contained in substrates, and can be applied to treat various cancer patients. These cancers include, but not limited to, cancer of lungs, intestine, stomach, mammary gland, ovary, prostate, uterus, pancreas, liver, bladder, kidney, thyroid gland, brain, head and neck, leukemia, and etc., which are directly related to over-expression of receptor tyrosine kinase.

According to the understanding of a skilled person in the art, some compounds, indicated in the Formula I, Formula II-I, Formula II-II, Formula II-III, Formula II-IV, Formula II-V, Formula II-VI, Formula III-I and Formula III-II of the invention, have a polycrystalline phenomenon. Thus, the types of inhibitory effect of these compounds on the receptor tyrosine kinase of ErbB family are also included within the scope of the invention. Furthermore, those compounds in form of tautomer are also included in the scope of the invention. Terminology used in the present invention has the same meaning with general concepts.

The term "substituted," as used herein, refers to substitution at a position with one more groups including, but not limited to, hydroxyl, C1-C8 alkyl, C2-C8 alkenyl, C2-C8 alkynyl, C3-C7 cycloalkyl, C1-C8 alkoxy, amine, C1-C8 alkylamino, di(C1-C8) alkylamino, C1-C8 alkylthio and halogen, and preferably selects from hydroxyl, methoxyl, amino, methylamino, dimethylamino, methylthio, halogen, and etc.

The term "halogen," as used herein, refers to group selected from fluorine, chlorine, bromine and iodine and any combination thereof.

The term "C," as used herein, should be understood as carbon or carbon atom. "C1-C3", "C1-C6", "C1-C8", "C2-C8", "C2-C4", "C3-C7" and "C6-C10" stand for carbon atom and its number present in groups, the letter C refers to carbon atom and the numeric behind it is a positive integer, e.g. 1, 2, 3, 4 or 5, which stands for the number of carbon atoms. Namely, C1 refers to a group bearing 1 carbon atom; C3 refers to a group bearing 3 carbon atoms; C1-C3 refers to a group of groups bearing 1-3 carbon atoms. Thus, the meaning of the expression above-mentioned and similar ones not listed herein can be understood by a skilled person in the art.

The term "acyl," as used herein, refers to a monovalent group derived from the organic or inorganic oxyacid by loss of hydroxyl, such as, but not limited to, nitroxyl, sulfonyl, carbonyl, sulphinyl, alkanoyl, and etc. Typical alkanoyl is such as, but not limited to, formyl, ethanoyl, propiono, and etc.

The term "sulfonyl," as used herein, refers to functional group derived from sulfoacid by loss of hydroxyl. It can be written as R—S(=O)$_2$—, wherein the substituted R is C1-C6 alkyl.

When the term "alkyl" as used herein is a group or part of a group, it refers to straight-chain saturated aliphatic hydrocarbon group or with branched chain. The said alkyl of the invention should be understood as the saturated aliphatic hydrocarbon group bearing unsubstituted hydrogen atom, including the saturated aliphatic hydrocarbon group that the hydrogen atom is partially or wholly substituted by "deuterium (D)". For example, the methyl should be understood as one or several of —CH$_3$, —CH$_2$D, —CHD$_2$, —CD$_3$, and etc. The alkyl of the invention preferably selects from C1-C8 alkyl, such as, but not limited to, methyl, ethyl, n-propyl, 2-propyl, n-butyl, isobutyl, tert-butyl, n-amyl, isoamyl, neoamyl, hexyl, and etc., and especially C1-C3 alkyl.

The term "cycloalkyl," as used herein, refers to saturated or partially saturated single-ring, condensed-ring, spiro aliphatic hydrocarbon cycloalkyl, and preferably selects from rings composed by 3-7 carbon atoms, such as, but not limited to, cyclopropyl, cyclopentyl, cyclohexyl, and etc.

The term "alkoxyl," as used herein, refers to (alkyl-O—) group, and preferably selects from C1-C6 alkoxyl, such as, but not limited to, methoxyl, ethyoxyl, n-propoxy, iso-propoxy, n-butoxy, isobutoxy, tert-butoxy, and etc.

When the term "alkenyl," as used herein, is a group or part of a group, it refers to aliphatic hydrocarbon group, which may be either straight chain or branched chain, bearing one carbon-carbon double bond. The present invention selects C3-C8 alkenyl, and preferably selects from C3, C4 and C5 alkenyl. The examples of alkenyl group includes, but not limited to, allyl and 2-butenyl.

When the term "alkynyl," as used herein, is a group or part of a group, it refers to aliphatic hydrocarbon group, which may be either straight chain or branched chain, bearing one carbon-carbon triple bond. The present invention selects C2-C6 alkynyl, and preferably selects from C2, C3 and C4 alkynyl, such as, but not limited to, ethynyl, propargyl, 2-alkyne butyl, and etc.

When the term "aryl group," as used herein, is used independently or in combination, it refers to carbocyclic aromatic system bearing one or two rings, wherein the said rings can be fused together. The term "aryl group" such as, but not limited to aryl group of phenyl, naphthyl and tetralyl, preferably selected from C6-C10 aryl group, and more preferably selected from phenyl. The said "aryl group" also bears one or several substituted groups, such as, but not limited to C1-C6 alkyl, hydroxyl, halogen, haloalkyl, nitryl, cyano-perssad, C1-C6 alkoxyl and C1-C6 alkylamino.

The term "heterocyclic group," as used herein, refers to aromatic or non-aromatic heterocyclic group, wherein one or several rings contain hetero atom, e.g. oxygen, nitrogen, sulfur, and etc. Aromatic heterocyclic group, i.e. commonly referred to heteroaryl, preferably from 5-6 membered monocyclic aromatic or 9-10 membered bicyclic aromatic which bears 1, 2 or 3 atoms selected from nitrogen, oxygen and sulfur, such as, but not limited to furyl, pyridyl, 2-oxo-1,2-dihydropyridine, pyridazinyl, pyrimidyl, pyrazinyl, thienyl, isoxazolyl, oxazolyl, oxadiazol, imidazolyl, pyrryl, pyrazolyl, triazolyl, tetrazolyl, thiazolyl, isothiazolyl, 1,2,3-thiadiazole, benzodioxol, benzimidazolyl, indolyl, isoindolyl, 1,3-dioxo-isoindolyl, quinolyl, indazolyl, benzisothiazolyl, benzoxazolyl, and benzisoxazolyl, pyridylof is preferred. The said "heteroaryl" bears one or several substituting groups such as, but not limited to C1-C6 alkyl, hydroxyl, halogen, haloalkyl, nitryl, cyano, C1-C6 alkoxyl, C1-C6 alkylamino and etc.

The term "non-aromatic heterocyclic group," as used herein, refers to non-aromatic heterocyclic group which preferably bears 5-6 membered monocyclic or 8-10 membered bicyclic or tricyclic, and may bears 1, 2 or 3 atoms selected from nitrogen, oxygen and sulfur, such as, but not limited to morpholinyl, thiomorpholinyl, tetrahydropyranyl, 1,1-dioxo-thiomorpholinyl, piperidyl, 2-oxo-piperidyl, pyrrolidinyl, 2-oxo-pyrrolidinyl, piperazine-2-ketone, 8-oxa-3-aza-bicyclic[3.2.1]octyl and piperazinyl. The said "non-aromatic heterocyclic group" also bears one or several substituted group such as, but not limited to C1-C6 alkyl, hydroxyl, halogen, haloalkyl, nitryl, cyano, C1-C6 alkoxyl and C1-C6 alkylamino.

The term "pharmaceutically acceptable salts," as used herein, refers to certain salts of the compounds of the invention can preserve original biological activity and are appropriate for medical use. These salts are such as metal salts, salts formed with proper organic base, and amine salts formed with proper acid. Metal salts are such as alkali metals and alkaline-earth metal salts, specifically calcium salt, magnesium salt or ammonium salt. The salts are formed with proper organic base such as methylamine, dimethylamine, piperidine, morpholine or 3-(2-hydroxyethyl)amine. The proper acids include inorganic and organic acids, such as, but not limited to acetic acid, benzene sulfonic acid, benzoic acid, camphorsulfonic acid, citric acid, ethyl sulfonic acid, fumaric acid, gluconic acid, glutamic acid, hydrobromic acid, chlorhydric acid, isethionic acid, lactic acid, malic acid, maleic acid, mandelic acid, methanesulfonic acid, nitric acid, phosphoric acid, succinic acid, sulphuric acid, tartaric acid or p-toluenesulfonic acid, and etc, preferably from chlorhydric acid, hydrobromic acid, phosphoric acid or sulphuric acid, more preferably from chlorhydric acid.

The term "treatment," as used herein, refers to preventing from and reducing occurrence or development of diseases and enabling development or aggravation course of diseases to be inhibited, controlled, alleviated, meliorated, retarded, ceased, delayed or reversed. All kinds of indicators and concerning disease, disorder or pathological condition at the time of the described preservation and medication include alleviation or reduction of symptoms or complications, or cure or elimination of diseases, disorders or condition.

The term "drugs," as used herein, refers to compound, composition consisting of multiple compounds, traditional Chinese medicinal materials and the extracts thereof, the composition or the formulation consists of the single compound as and compounds and used in remedy of diseases, or composition or formulation with single compound as main active ingredient. It also refers to composition or formulation with a variety of compounds as active ingredients. "Drugs" should be understood not only as products approved and permitted by administrative organization established according to the law of a country, but also all kinds of material forms, containing the single compound as active ingredient, formed in the process to obtain the approval and permission for manufacture. The "formed" should be understood to obtain by means of chemical synthesis, biotransformation or purchasing.

The term "effective therapeutic dose," as used herein, refers to the dose, using the compounds as active ingredient, which can alleviate various symptoms pathologically. Generally, the dose delivered is determined according to body weight of organisms, e.g. a total dose of 0.05 mg/kg-50 mg/kg daily. According to actual situation of organism and its diseases, the dose and the delivery frequency may also be adjusted e.g. dividing more than twice a day, and giving a total dose of 0.05-0.5 mg/kg, 0.6-1 mg/kg, 1-10 mg/kg, 11-25 mg/kg, 26-40 mg/kg or 41-50 mg/kg. According to different types of formulation, the given dose should also be changed, e.g. 10 mg/kg for ordinary tablet, or lower for controlled and sustained release formulation. The specific dose of heterocycle amido alkyloxy substituted quinazoline derivative and pharmaceutically acceptable salts of the present invention should be determined depending on the circumstances, such as mode of administration, route of administration, the state of patients when administrated, and pathological condition when treated.

The terms "Patient," "organism" or "animal" as used herein, refer to human, wild animal and livestock. Wild animals are natural without artificial domestication. Livestock is an animal fed artificially to provide source of food, such as, but not limited to dog, mouse, hamster, pig, horse, rabbit, dairy cow, buffalo, bull, sheep, goat, geese and chicken. The subjected in certain aspects, a "patient," "organism" or "animal" is preferably mammals, especially humans.

DRAWINGS

Figure 2:
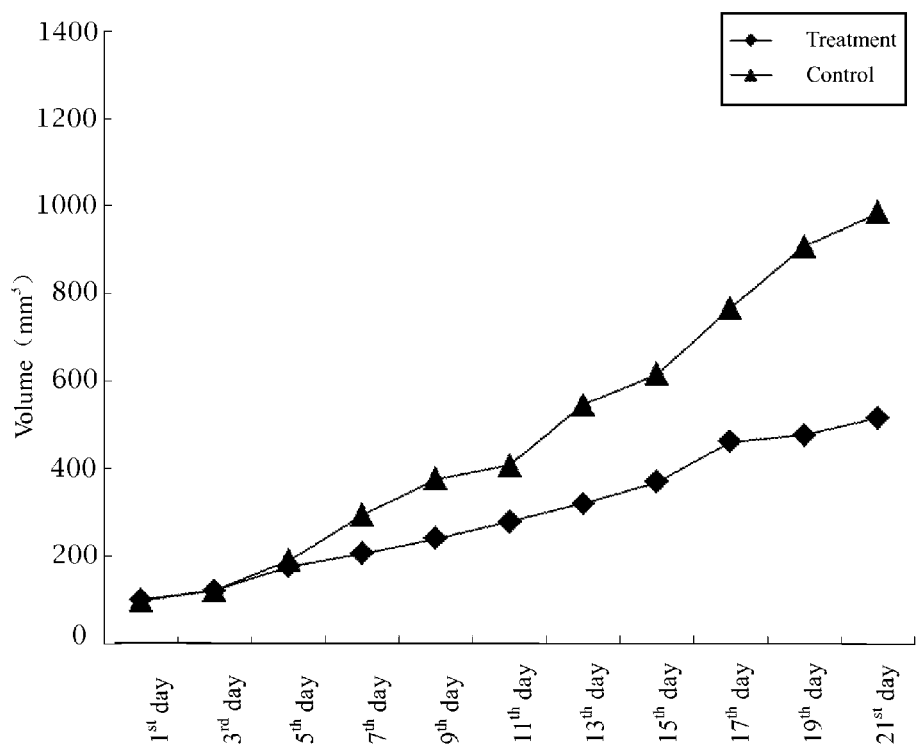

FIG. 1 refers to body weight trends of nude mice.
FIG. 2 refers to tumor volume growth trends of nude mice.

EXAMPLES

The present invention will be detailed described as follows. Examples of the invention are intended only to illustrate the invention, not to limit. Although the invention is illustrated in detail with reference of the preferred examples, a skilled person in the art can understand and find an identical or improved technical solution without departing from the spirit and scope of the present invention, which should cover the scope of the claims.

In the following examples, unless otherwise specified, all temperature are expressed in centigrade degree (° C.). Unless otherwise specified, all kinds of initiative raw materials and agents can be acquired commercially, e.g. Sigma-Aldrich. These acquired raw materials and agents are directly used without any further purification.

Glassware was dried by oven and/or heating. The reaction was tracked by silicone-60 F254 plate (0.25 mm, TLC). The analytic of thin-layer chromatography is spread out in proper solvent ratio (v/v).

$^1$H NMR spectra is determined by Bruker apparatus (400 MHz). The chemical shift is expressed in ppm. Tetramethylsilane is applied to internal standard (0.00 ppm). The expression of $^1$H NMR are as follows: s=singlet, d=doublet, t=triplet, m=multiplet, br=broadened, dd=doublet of doublet. When giving a coupling constant, its unit is Hz.

The molecular weight of product is determined by LC/MS mass spectrometer, and the ionization method is ESI or APCI.

Various heterocycle amido alkyloxy substituted quinazoline derivative, pharmaceutically acceptable salts or its hydrates provided of the invention can be prepared by various public organic synthesis technologies. A simple and effective method to prepare various compounds of the invention is shown in the formula IV or the formula V i.e. synthesizing the two intermediates A and B or the two intermediates C and D firstly, and the final product of Formula I can be prepared by the intermediates.

Formula IV

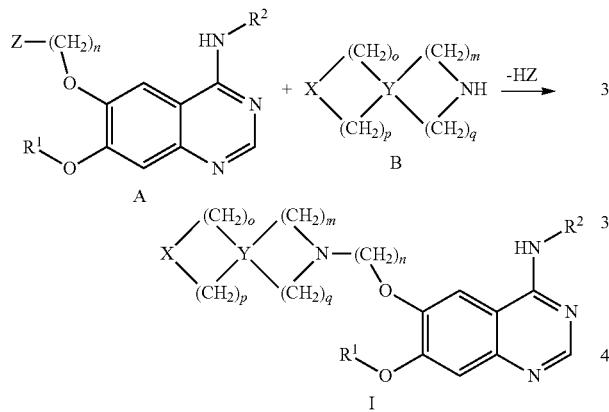

Formula V

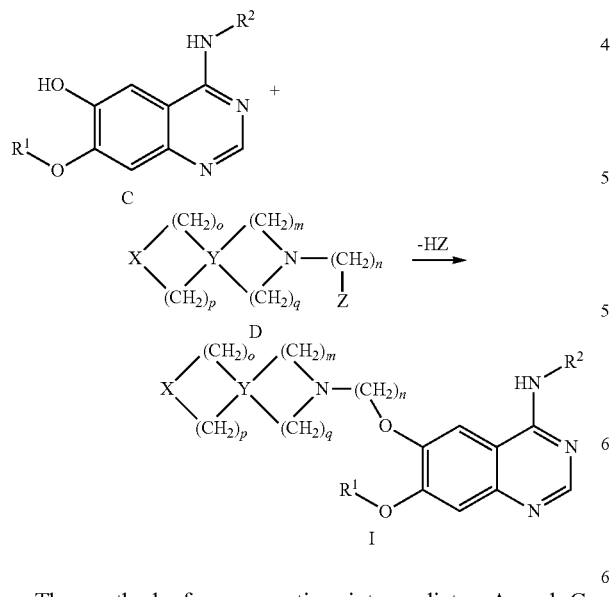

The methods for preparation intermediates A and C involved in the formula IV or formula V can be referred to J. Med. Chem., 1996, 39, 267-276 or U.S. Pat. No. 5,616,582. The specific preparation process can be referred to the reaction from compound 1 to compound 7 of the formula VI. The intermediates B and D can be commercially purchased, or prepared by commercially entrusting a third party (North Carolina Chemlabs (Shanghai)).

In formula, A, B, C and D represent the structure of intermediates, except for the letter "Z", all the letters applied in the formulas and their meanings represented are identical to the meaning of Formula I respectively. The letter "Z" stands for leaving group, includes, but not limited to, Cl, Br, OH or OMs, and etc.

The preparation method provided in the present invention should be understood as necessary example for fully disclosure but not restriction to protective scope of the invention claims. Various compounds provided in the invention can be prepared by a skilled person in the art in the light of the examples listed in textbook, laboratory manual or the invention. The preparation of these compounds is also a part of generally indispensable skills which shall be mastered by a skilled person in the art, and can be completed under the guidance of the prior arts. Specifically, the preparation methods for some of the compounds provided in the invention is given as follows:

Synthetic scheme 1

Formula VI

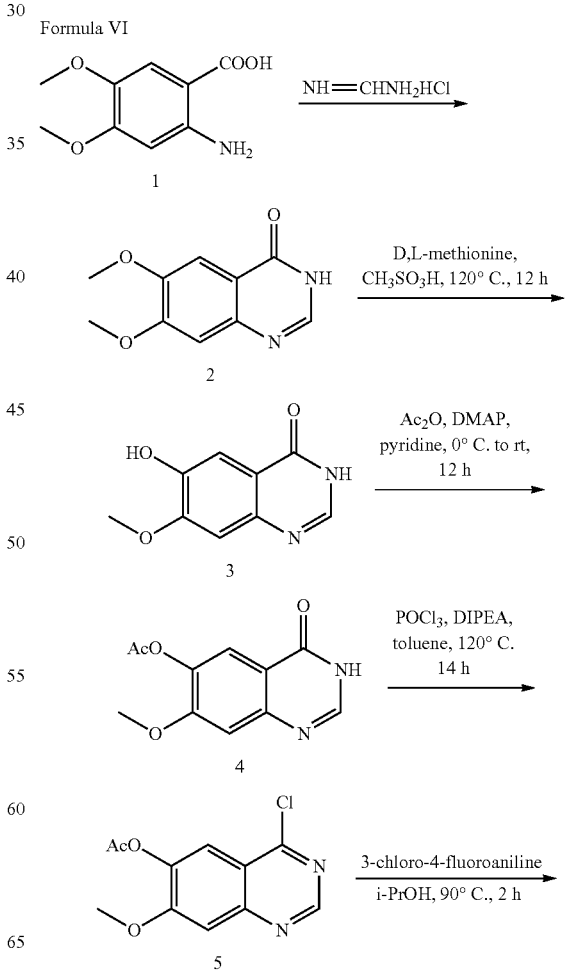

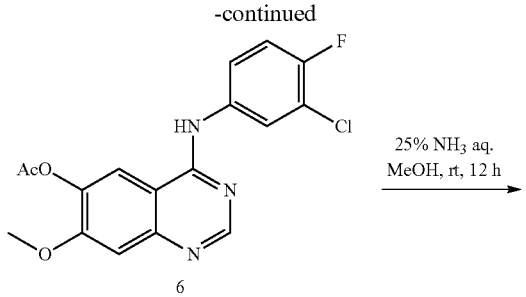

6

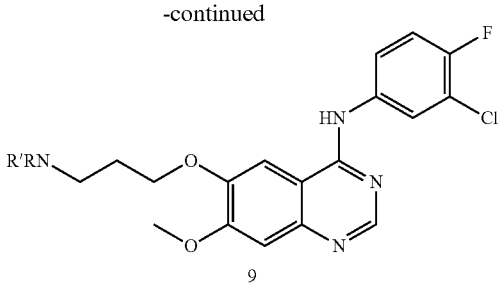

9

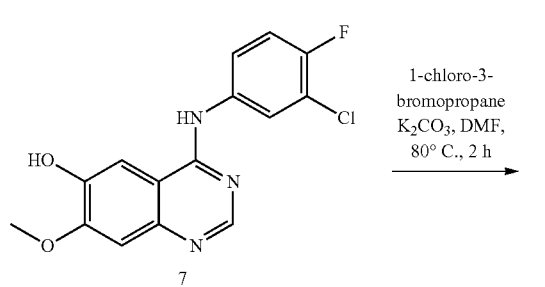

7

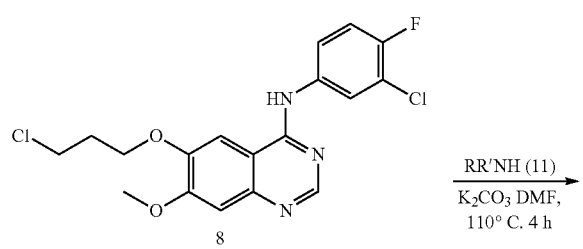

8

9

Synthetic scheme 2

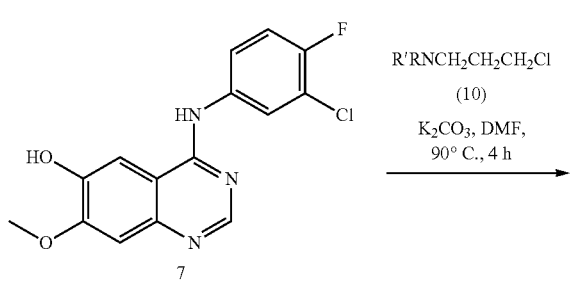

7

The following Examples are intended to illustrate the synthesis of compounds of the present invention only, but in these synthesis methods and without any restrictions. Compounds not listed in the following can also be prepared by the following synthetic routes and methods of the same, selecting the appropriate starting materials, and adjusting reaction conditions in the proper sense in somewhere necessary.

Synthetic Scheme 1 (Formula VI)

The steps for the synthesis of intermediate compound 8:

Referring to the formula IV, and according to the formula VI, compound 7 (478 mg, 1.5 mmol), 1-bromo-3-chloropropane (1.18 g, 7.5 mmol) and $K_2CO_3$ (1.05 g, 7.5 mmol) were added in into the flask prefilled with 3 ml of DMF, heating it up to 90° C. and keeping for 4 hours, and then cooling down to the room temperature. 15 ml of water was added in, and the organic phases, extracted by ethyl acetate (20 ml×3), were combined. The combined organic phase was washed by water and saturated aqueous solution of $Na_2CO_3$ respectively. $MgSO_4$, used as desiccant, was added. The solvent was removed by rotary evaporator after the desiccant was removed by filtration. Using silica gel column (gradient elution using petroleum ether containing 20 v/v %-80 v/v % ethyl acetate as eluent) to separate the residue, and about 330 mg of product 8 was obtained.

The steps for product 9 synthesis are as follows:

Compound 8 (96 mg, 0.3 mmol), amine 11 (RR'NH, 0.5 mmol) and $K_2CO_3$ (0.21 g, 1.5 mmol) were added in into the flask prefilled with 3 ml of DMF, the flask was heated up to 110° C. and kept for 4 hours, and then cooling down to the room temperature. 10% aqueous solution of $Na_2CO_3$ (10 ml) and ethyl acetate (20 ml) was added in, and fully shaking to separate the organic phase. The separated organic phase was washed by saturated aqueous solution of $Na_2CO_3$. $MgSO_4$, used as desiccant, was added. The solvent was removed by rotary evaporator after the desiccant was removed by filtration. Using silica gel column or plate chromatography (using methylene dichloride containing 5 v/v %-20 v/v % methanol as eluent) to separate the residue, and the product 9 was obtained.

Synthetic Scheme 2 (Formula VW)

Referring to the formula V, and according to the formula VII, compound 7 (96 mg, 0.3 mmol), 3-chloropropyl-substituted amine 10 (0.5 mmol) and $K_2CO_3$ (0.21 g, 1.5 mmol) were added in into the flask prefilled with 3 ml of DMF, heating it up to 90° C. and keeping for 4 hours, and then cooling down to the room temperature. 10 ml water was added in, and the organic phases, extracted by ethyl acetate (10 ml×3), were combined. The combined organic phase was washed by water and saturated aqueous solution of $Na_2CO_3$ respectively. $MgSO_4$, used as desiccant, was added. The solvent was removed by rotary evaporator after the desiccant was removed by filtration. Using silica gel column or plate chromatography (using methylene dichloride containing 5 v/v %-20 v/v % methanol as eluent) to separate the residue, and the product 9 was obtained.

Example 1

Using a procedure identical to that described in synthetic scheme 1, the compound 4-(3'-chloro-4'-fluorophenylamino)-6-[3-(2-oxa-6-azaspiro[3.3]heptane-6-yl)-propoxy]-7-methoxyquinazoline (3-C—B) was obtained.

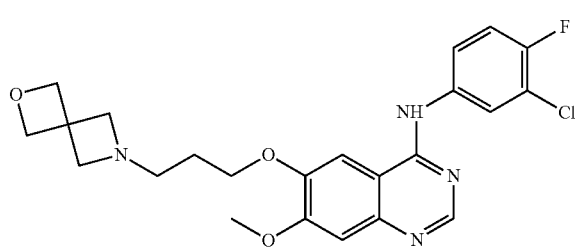 [SMILES: COc1cc2ncnc(Nc3ccc(F)c(Cl)c3)c2cc1OCCCN1CC2(COC2)C1]

$^1$H NMR (CDCl$_3$) 8.67 (s, 1H), 8.03 (s, 2H), 7.68 (br, 1H), 7.46 (s, 1H), 7.25 (s, 1H), 7.18 (m, 1H), 4.79 (s, 4H), 4.25 (m, 2H), 4.01 (s, 3H), 3.66 (s, 4H), 2.80 (m, 2H), 2.03 (m, 2H). ES-MS (m/z): 459.1 (MH$^+$).

Example 2

Using a procedure identical to that described in synthetic scheme 1, the compound 4-(3'-chloro-4'-fluorophenylamino)-6-[3-(2-oxa-6-azaspiro[3.4]octane-6-yl)-propoxy]-7-methoxyquinazoline (3-C—C) was obtained.

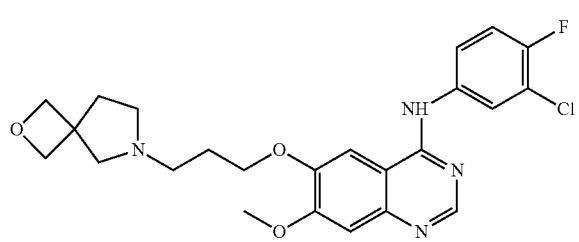 [SMILES: COc1cc2ncnc(Nc3ccc(F)c(Cl)c3)c2cc1OCCCN1CCC2(COC2)C1]

$^1$H NMR (CDCl$_3$) 8.67 (s, 1H), 8.20 (s, 1H), 8.07 (q, J=2.4 Hz, 1H), 7.70 (m, 1H), 7.57 (s, 1H), 7.25 (s, 1H), 7.17 (t, J=8.8 Hz, 1H), 4.69 (q, J=6.4 Hz, 4H), 4.30 (t, J=6.8 Hz, 2H), 4.01 (s, 3H), 3.18 (s, 2H), 2.90 (t, J=6.4 Hz, 4H), 2.33 (t, J=7.2 Hz, 2H), 2.22 (m, 2H). ES-MS (m/z): 473.0 (MH$^+$).

Example 3

Using a procedure identical to that described in synthetic scheme 2, the compound 4-(3'-chloro-4'-fluorophenylamino)-6-[2-(2-oxa-6-azaspiro[3.4]octane-6-yl)-oxethyl]-7-methoxyquinazoline (2-C—C) was obtained.

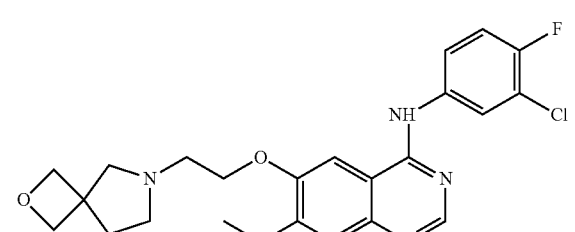

$^1$H NMR (CDCl$_3$) 8.68 (s, 1H), 7.93 (q, J=2.4 Hz, 1H), 7.56 (m, 1H), 7.46 (m, 1H), 7.23 (s, 1H), 7.17 (t, J=8.8 Hz, 1H), 4.67 (s, 4H), 4.34 (t, J=6.4 Hz, 2H), 4.04 (s, 3H), 3.04 (t, J=4.8 Hz, 4H), 2.75 (t, J=6.8 Hz, 2H), 2.19 (q, J=7.2 Hz, 2H). ES-MS (m/z): 459.8 (MH$^+$).

Example 4

Using a procedure identical to that described in synthetic scheme 1, the compound 4-(3'-chloro-4'-fluorophenylamino)-6-[3-(7-oxa-2-azaspiro[3.5]nonane-2-yl)-propoxy]-7-methoxyquinazoline (3-C—F) was obtained.

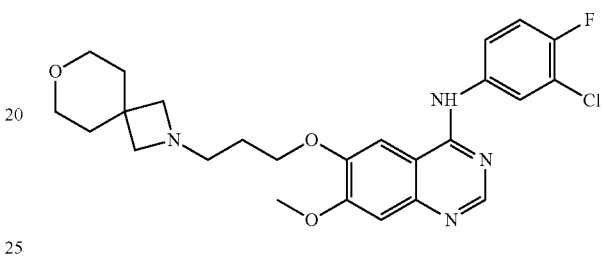

$^1$H NMR (CDCl$_3$) 8.67 (s, 1H), 8.48 (br, 1H), 8.23 (d, J=4.4 Hz, 1H), 8.08 (br, 1H), 7.82 (t, J=6.0 Hz, 1H), 7.27 (s, 1H), 7.17 (t, J=8.8 Hz, 1H), 4.50 (t, J=6.4 Hz, 2H), 4.03 (s, 3H), 3.75 (m, 4H), 3.62 (t, J=4.8 Hz, 4H), 3.23 (s, 2H), 2.23 (t, J=6.4 Hz, 2H), 1.97 (m, 4H). ES-MS (m/z): 487.8 (MH$^+$).

Example 5

Using a procedure identical to that described in synthetic scheme 1, the compound 4-(3'-chloro-4'-fluorophenylamino)-6-[3-(2-oxa-7-azaspiro[3.5]nonane-7-yl)-propoxy]-7-methoxyquinazoline (3-C-G) was obtained.

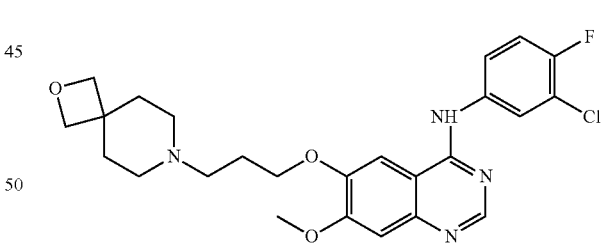

$^1$H NMR (CDCl$_3$) 8.68 (s, 1H), 8.00 (q, J=2.4 Hz, 1H), 7.64 (m, 2H), 7.30 (br, 1H), 7.19 (t, J=8.8 Hz, 1H), 4.45 (s, 4H), 4.30 (t, J=6.8 Hz, 2H), 4.04 (s, 3H), 2.73 (m, 2H), 2.61 (m, 4H), 2.23 (t, J=6.8 Hz, 2H), 2.06 (s, 4H). ES-MS (m/z): 487.8 (MH$^+$).

Example 6

Using a procedure identical to that described in synthetic scheme 1, the compound 4-(3'-chloro-4'-fluorophenylamino)-6-[2-(7-oxa-2-azaspiro[3.5]nonane-2-yl)-oxethyl]-7-methoxyquinazoline (2-C-G) was obtained.

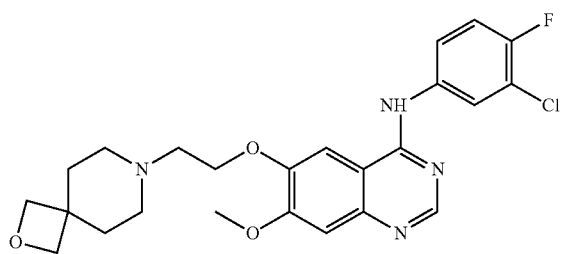 [SMILES: COc1cc2ncnc(Nc3ccc(F)c(Cl)c3)c2cc1OCCN1CCC2(CC1)COC2]

¹H NMR (CDCl₃) 8.68 (s, 1H), 7.94 (q, J=2.4 Hz, 1H), 7.60 (m, 1H), 7.54 (m, 1H), 7.31 (s, 1H), 7.19 (t, J=8.8 Hz, 1H), 4.45 (s, 4H), 4.36 (t, J=6.4 Hz, 2H), 4.03 (s, 3H), 2.91 (t, J=6.4 Hz, 2H), 2.51 (m, 4H), 1.92 (m, 4H). ES-MS (m/z): 473.3 (MH⁺).

Example 7

Using a procedure identical to that described in synthetic scheme 1, the compound 4-(3'-chloro-4'-fluorophenylamino)-6-[3-(2-oxa-7-azaspiro[4.4]nonane-7-yl)-propoxy]-7-methoxyquinazoline (3-C—H) was obtained.

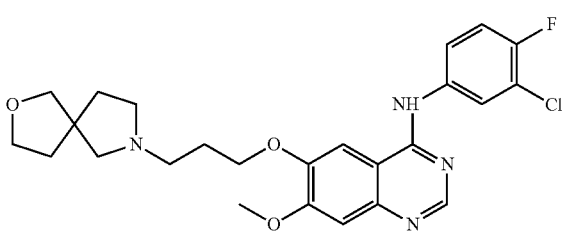 [SMILES: COc1cc2ncnc(Nc3ccc(F)c(Cl)c3)c2cc1OCCCN1CCC2(CCOC2)C1]

¹H NMR (CDCl₃) 8.64 (s, 1H), 8.33 (s, 1H), 8.24 (dd, J, J=2.4 Hz, 1H), 7.86 (m, 1H), 7.33 (s, 1H), 7.14 (t, J=8.8 Hz, 1H), 4.60 (t, J=10.9 Hz, 2H), 4.02 (s, 3H), 3.93 (m, 2H), 3.84 (d, J=8.4 Hz, 1H), 3.73 (t, J=8.8 Hz, 2H), 3.40 (t, J=6.4 Hz, 3H), 2.43 (m, 2H), 2.27 (m, 4H), 2.12 (m, 2H). ES-MS (m/z): 487.3 (MH⁺).

Example 8

Using a procedure identical to that described in synthetic scheme 1, the compound 4-(3'-chloro-4'-fluorophenylamino)-6-[2-(2-oxa-7-azaspiro[4.4]nonane-7-yl)-oxethyl]-7-methoxyquinazoline (2-C—H) was obtained.

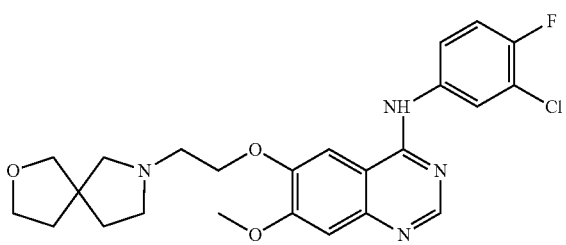

¹H NMR (CDCl₃) 8.68 (s, 1H), 8.02 (q, J=2.4 Hz, 1H), 7.91 (s, 1H), 7.64 (m, 1H), 7.50 (s, 1H), 7.18 (t, J=8.8 Hz, 1H), 4.45 (t, J=6.4 Hz, 2H), 4.03 (s, 3H), 3.91 (m, 2H), 3.78 (d, J=8.4 Hz, 1H), 3.62 (d, J=8.4 Hz, 1H), 3.15 (m, 2H), 3.01 (m, 3H), 2.78 (m, 1H), 2.02 (m, 4H). ES-MS (m/z): 473.3 (MH⁺).

Example 9

Using a procedure identical to that described in synthetic scheme 1, the compound 4-(3'-chloro-4'-fluorophenylamino)-6-[3-(8-oxa-2-azaspiro[4.5]decane-2-yl)-propoxy]-7-methoxyquinazoline (3-C—K) was obtained.

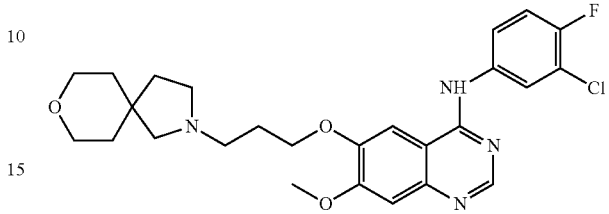

¹H NMR (CDCl₃) 10.20 (br, 1H), 8.63 (s, 1H), 8.50 (s, 1H), 8.11 (q, J=2.4 Hz, 1H), 7.81 (m, 1H), 7.58 (s, 1H), 7.16 (t, J=8.8 Hz, 1H), 4.61 (t, J=6.4 Hz, 2H), 4.04 (s, 3H), 3.68 (m, 4H), 3.43 (m, 3H), 2.46 (m, 3H), 2.23 (m, 4H), 1.82 (m, 4H). ES-MS (m/z): 501.3 (MH⁺).

Example 10

Using a procedure identical to that described in synthetic scheme 1, the compound 4-(3'-chloro-4'-fluorophenylamino)-6-[2-(8-oxa-2-azaspiro[4.5]decane-2-yl)-oxethyl]-7-methoxyquinazoline (2-C—K) was obtained.

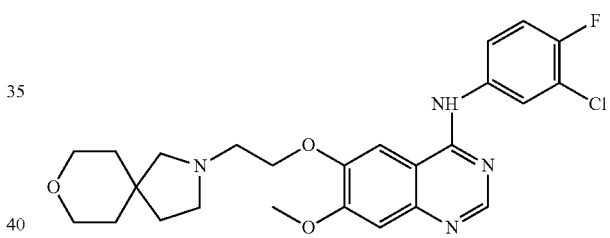

¹H NMR (CDCl₃) 8.68 (s, 1H), 7.98 (q, J=2.4 Hz, 1H), 7.73 (br, 1H), 7.62 (m, 1H), 7.40 (s, 1H), 7.19 (t, J=8.8 Hz, 1H), 4.42 (t, J=6.4 Hz, 2H), 4.04 (s, 3H), 3.67 (t, J=5.2 Hz, 4H), 3.10 (t, J=6.4 Hz, 2H), 2.90 (t, J=6.4 Hz, 2H), 2.73 (s, 2H), 1.82 (m, 4H), 1.64 (m, 2H). ES-MS (m/z): 487.3 (MH⁺).

Example 11

Using a procedure identical to that described in synthetic scheme 1, the compound 4-(3'-chloro-4'-fluorophenylamino)-6-[2-(8-oxa-3-azabicyclo[3.2.1]octane-3-yl)-oxethyl]-7-methoxyquinazoline (2-C-M) was obtained.

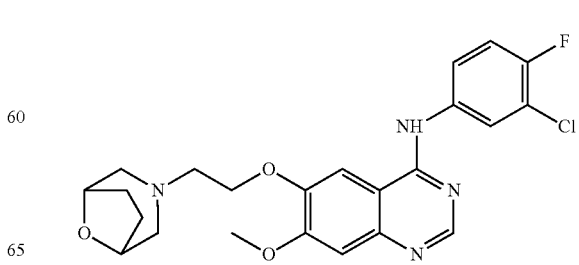

¹H NMR (CDCl₃) 8.69 (s, 1H), 7.99 (q, J=2.4 Hz, 1H), 7.61 (m, 2H), 7.37 (s, 1H), 7.20 (t, J=8.8 Hz, 1H), 4.41 (t, J=6.8 Hz, 2H), 4.04 (s, 3H), 3.87 (d, J=10.8 Hz, 2H), 3.59 (d, J=10.8 Hz, 2H), 3.30 (s, 2H), 2.95 (m, 2H), 2.05 (m, 4H). ES-MS (m/z): 459.1 (MH⁺).

Example 12

Using a procedure identical to that described in synthetic scheme 1, the compound 4-(3'-chloro-4'-fluorophenylamino)-6-[3-(8-oxa-3-azabicyclo[3.2.1]octane-3-yl)-propoxy]-7-methoxyquinazolin (3-C—O) was obtained.

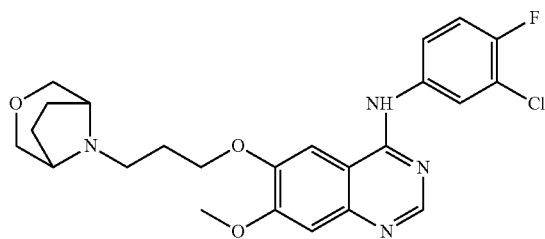 [SMILES: COc1cc2ncnc(Nc3ccc(F)c(Cl)c3)c2cc1OCCCN1C2CCC1COC2]

¹H NMR (CDCl₃) 8.69 (s, 1H), 7.90 (q, J=2.4 Hz, 1H), 7.56 (m, 1H), 7.20 (t, J=8.8 Hz, 1H), 7.12 (s, 1H), 7.03 (s, 1H), 4.33 (s, 2H), 4.22 (t, J=6.8 Hz, 2H), 4.04 (s, 3H), 2.67 (d, J=10.7 Hz, 2H), 2.57 (t, J=6.8 Hz, 2H), 2.38 (d, J=10.9 Hz, 2H), 2.10 (m, 2H), 1.89 (m, 4H). ES-MS (m/z): 473.2 (MH⁺).

Example 13

Using a procedure identical to that described in synthetic scheme 1, the compound 4-(3'-chloro-4'-fluorophenylamino)-6-[2-(3-oxa-8-azabicyclo[3.2.1]octane-8-yl)-oxethyl]-7-methoxyquinazoline (2-C—O) was obtained.

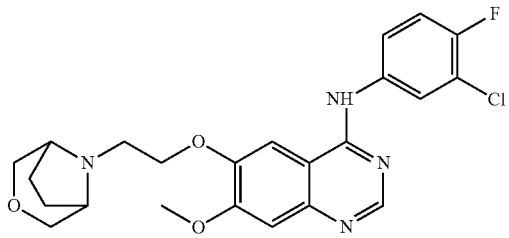 [SMILES: COc1cc2ncnc(Nc3ccc(F)c(Cl)c3)c2cc1OCCN1C2CCC1COC2]

¹H NMR (CDCl₃) 8.69 (s, 1H), 7.92 (q, J=2.4 Hz, 1H), 7.56 (m, 1H), 7.28 (s, 1H), 7.21 (t, J=8.8 Hz, 1H), 7.09 (s, 1H), 4.34 (d, J=2.4 Hz, 2H), 4.28 (t, J=6.0 Hz, 2H), 4.04 (s, 3H), 2.93 (t, J=6.0 Hz, 2H), 2.73 (d, J=10.0 Hz, 2H), 2.57 (d, J=9.6 Hz, 2H), 1.98 (m, 2H), 1.90 (m, 2H). ES-MS (m/z): 459.1 (MH⁺).

Example 14

Using a procedure identical to that described in synthetic scheme 1, the compound 4-(5'-chloro-2'-fluorophenylamino)-6-[3-(2-oxa-6-azaspiro[3.3]heptane-6-yl)-propoxy]-7-methoxyquinazoline (3-2-B) was obtained.

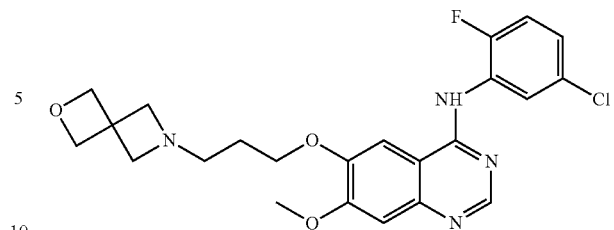

¹H NMR (CDCl₃) 8.72 (s, 1H), 8.47 (d, J=6.0 Hz, 1H), 7.90 (br, 1H), 7.50 (s, 1H), 7.10 (m, 2H), 4.81 (s, 4H), 4.34 (t, J=6.4 Hz, 2H), 4.04 (s, 3H), 3.86 (s, 4H), 2.96 (m, 2H), 2.12 (m, 2H). ES-MS (m/z): 459.1 (MH⁺).

Example 15

Using a procedure identical to that described in synthetic scheme 1, the compound 4-(5'-chloro-2'-fluorophenylamino)-6-[3-(2-oxa-7-azaspiro[4.4]nonane-7-yl)-propoxy]-7-methoxyquinazoline (3-2-H) was obtained.

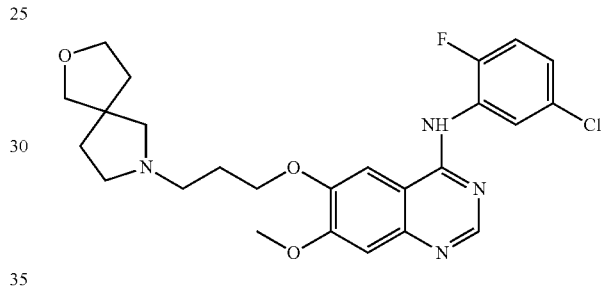

¹H NMR (CDCl₃) 8.67 (s, 1H), 8.46 (s, 1H), 8.25 (d, J=6.0 Hz, 1H), 7.76 (s, 1H), 7.29 (s, 1H), 7.10 (m, 1H), 4.45 (t, J=6.4 Hz, 2H), 4.03 (s, 3H), 3.92 (m, 2H), 3.80 (d, J=8.8 Hz, 1H), 3.70 (d, J=8.8 Hz, 1H), 3.42 (br, 1H), 3.24 (m, 5H), 2.42 (m, 2H), 2.18 (m, 3H), 2.06 (m, 1H). ES-MS (m/z): 487.0 (MH⁺).

Example 16

Using a procedure identical to that described in synthetic scheme 1, the compound 4-(5'-chloro-2'-fluorophenylamino)-6-[3-(3-oxa-8-azabicyclo[3.2.1]octane-8-yl)-propoxy]-7-methoxyquinazolin (3-2-O) was obtained.

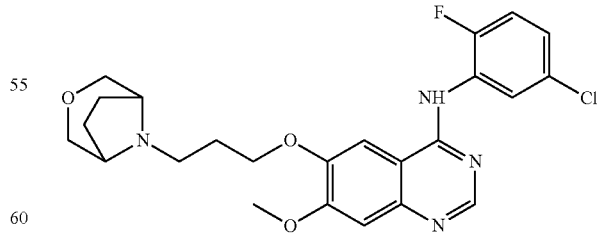

¹H NMR (CDCl₃) 8.78 (m, 2H), 7.55 (br, 1H), 7.32 (br, 1H), 7.08 (m, 3H), 4.33 (s, 2H), 4.28 (t, J=6.4 Hz, 2H), 4.05 (s, 3H), 2.81 (d, J=9.6 Hz, 2H), 2.61 (m, 2H), 2.40 (d, J=10.8 Hz, 2H), 2.12 (t, J=6.8 Hz, 2H), 1.88 (m, 4H). ES-MS (m/z): 473.0 (MH⁺).

Example 17

Using a procedure identical to that described in synthetic scheme 1, the compound 4-(3'-chloro-4'-fluorophenylamino)-6-[3-(8-oxa-2-azaspiro[4.5]decane-2-yl)-propoxy]-7-methoxyquinazoline (3-2-K) was obtained.

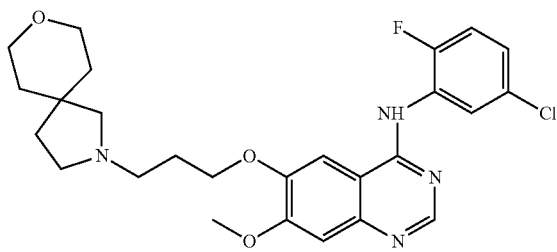 [SMILES: COc1cc2ncnc(Nc3cc(Cl)ccc3F)c2cc1OCCCN1CCC2(CCOCC2)C1]

$^1$H NMR (CDCl$_3$) 8.68 (s, 1H), 8.36 (br, 1H), 8.23 (d, J=6.4 Hz, 1H), 7.77 (s, 1H), 7.10 (m, 2H), 4.46 (t, J=6.0 Hz, 2H), 4.03 (s, 3H), 3.68 (t, J=8.8 Hz, 4H), 3.24 (m, 4H), 2.43 (m, 3H), 2.09 (m, 3H), 1.77 (m, 4H). ES-MS (m/z): 500.8 (MH$^+$).

Example 18

Using a procedure identical to that described in synthetic scheme 1, the compound 4-(5'-chloro-2'-fluorophenylamino)-6-[3-(7-oxa-2-azaspiro[3.5]-nonane-2-yl)-propoxy]-7-methoxyquinazoline (3-2-F) was obtained.

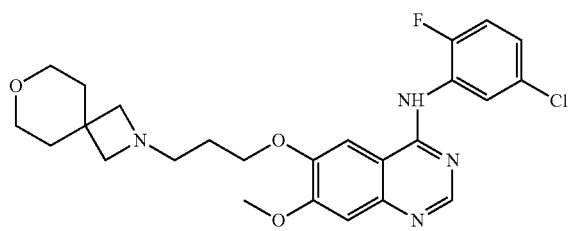 [SMILES: COc1cc2ncnc(Nc3cc(Cl)ccc3F)c2cc1OCCCN1CC2(CCOCC2)C1]

$^1$H NMR (CDCl$_3$) 8.68 (s, 1H), 8.42 (br, 1H), 8.21 (d, J=6.8 Hz, 2H), 7.80 (s, 1H), 7.11 (m, 2H), 4.44 (t, J=6.4 Hz, 2H), 4.03 (s, 3H), 3.79 (s, 4H), 3.61 (t, J=4.8 Hz, 4H), 3.27 (t, J=6.4 Hz, 2H), 2.26 (m, 2H), 1.96 (s, 4H). ES-MS (m/z): 486.8 (MH$^+$).

Example 19

Using a procedure identical to that described in synthetic scheme 2, the compound 4-(5'-chloro-2'-fluorophenylamino)-6-[3-(7-acetyl-2,7-diazaspiro[4.4]-nonane-2-yl)-propoxy]-7-methoxyquinazoline (3-2-7) was obtained.

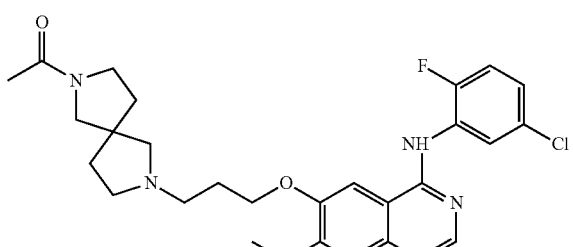

$^1$H NMR (CDCl$_3$) 8.71 (s, 1H), 8.39 (m, 1H), 8.06 (m, 1H), 7.51 (s, 1H), 7.30 (s, 1H), 7.10 (m, 2H), 4.31 (t, J=6.0 Hz, 2H), 4.04 (s, 3H), 3.54 (m, 3H), 3.38 (m, 1H), 3.04 (m, 1H), 2.85 (m, 1H), 2.23 (t, J=6.8 Hz, 2H), 2.05 (s, 3H), 1.90 (m, 4H). ES-MS (m/z): 527.8 (MH$^+$).

Example 20

Using a procedure identical to that described in synthetic scheme 1, the compound 4-(5'-chloro-2'-fluorophenylamino)-6-[3-(7-acetyl-2,7-diazaspiro[4.4]-nonane-2-yl)-propoxy]-7-methoxyquinazoline (3-2-11) was obtained.

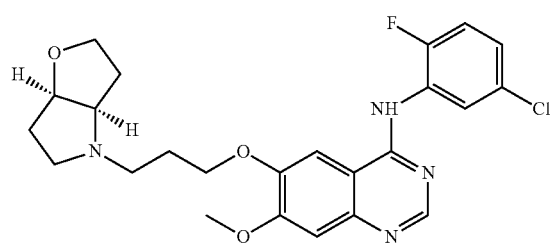 [SMILES: COc1cc2ncnc(Nc3cc(Cl)ccc3F)c2cc1OCCCN1CC[C@H]2OCC[C@H]21]

$^1$H NMR (CDCl$_3$) 8.74 (s, 1H), 8.62 (br, 1H), 7.65 (m, 1H), 7.31 (s, 1H), 7.09 (m, 2H), 4.61 (m, 1H), 4.33 (t, J=6.0 Hz, 2H), 4.05 (s, 3H), 3.93 (m, 1H), 3.79 (m, 1H), 3.54 (br, 1H), 3.20 (m, 1H), 3.05 (m, 1H), 2.55 (br, 1H), 2.25 (m, 4H), 1.93 (m, 4H). ES-MS (m/z): 472.8 (MH$^+$).

Example 21

Using a procedure identical to that described in synthetic scheme 1, the compound 4-(5'-chloro-2'-fluorophenylamino)-6-[3-(2,8-diazaspiro[4.5]decyl-3-ketone-8-yl)-propoxy]-7-methoxyquinazoline (3-2-20) was obtained.

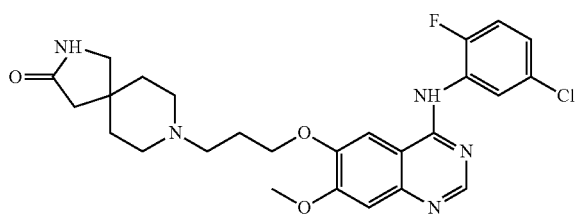 [SMILES: COc1cc2ncnc(Nc3cc(Cl)ccc3F)c2cc1OCCCN1CCC2(CC1)CNC(=O)C2]

$^1$H NMR (CDCl$_3$) 8.75 (s, 1H), 8.65 (br, 1H), 7.60 (m, 1H), 7.30 (s, 1H), 7.09 (m, 2H), 5.50 (s, 1H), 4.30 (t, J=6.4 Hz, 2H), 4.04 (s, 3H), 3.25 (s, 2H), 2.90 (m, 2H), 2.69 (m, 2H), 2.32 (m, 2H), 2.27 (s, 2H), 2.04 (m, 2H), 1.90 (m, 4H). ES-MS (m/z): 514.1 (MH$^+$).

Example 22

Using a procedure identical to that described in synthetic scheme 1, the compound 4-(5'-chloro-2'-fluorophenylamino)-6-[3-(2,7-diazaspiro[4.4]nonane-1-ketone-7-yl)-propoxy]-7-methoxyquinazoline (3-2-21) was obtained.

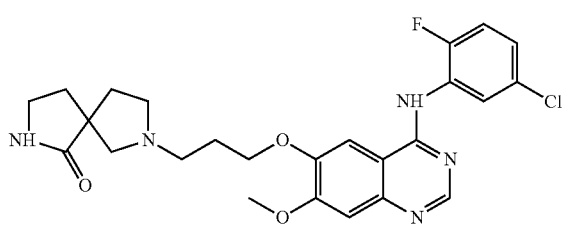 [SMILES: COc1cc2ncnc(Nc3cc(Cl)ccc3F)c2cc1OCCCN1CCC2(CCNC2=O)C1]

¹H NMR (CDCl₃) 8.74 (s, 1H), 8.58 (br, 1H), 7.75 (br, 1H), 7.30 (s, 1H), 7.10 (m, 2H), 5.60 (s, 1H), 4.32 (t, J=6.4 Hz, 2H), 4.04 (s, 3H), 3.52 (d, J=9.2 Hz, 1H), 3.37 (d, J=10.0 Hz, 1H), 3.12 (m, 2H), 2.93 (m, 2H), 2.85 (m, 1H), 2.72 (d, J=9.2 Hz, 1H), 2.44 (m, 2H), 2.25 (m, 2H), 2.06 (m, 2H). ES-MS (m/z): 500.0 (MH⁺).

Example 23

Using a procedure identical to that described in synthetic scheme 1, the compound 4-(5'-chloro-2'-fluorophenylamino)-6-[3-(2-methyl-2,7-diazaspiro[4.4]nonane-1-ketone-7-yl)-propoxy]-7-methoxyquinazoline (3-2-22) was obtained.

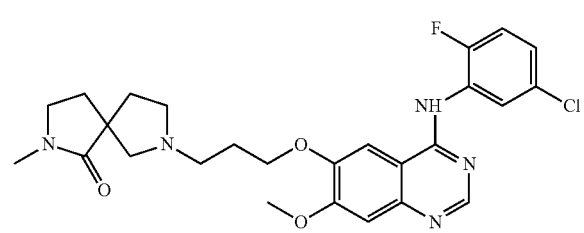 [SMILES: COc1cc2ncnc(Nc3cc(Cl)ccc3F)c2cc1OCCCN1CCC2(CCN(C)C2=O)C1]

¹H NMR (CDCl₃) 8.68 (s, 1H), 8.40 (br, 1H), 8.19 (d, J=6.8 Hz, 1H), 7.83 (s, 1H), 7.11 (m, 2H), 4.50 (m, 2H), 4.04 (s, 3H), 3.53 (m, 4H), 3.35 (m, 2H), 3.19 (m, 2H), 2.88 (s, 3H), 2.30 (m, 4H), 2.20 (m, 2H). ES-MS (m/z): 514.1 (MH⁺).

Example 24

Using a procedure identical to that described in synthetic scheme 1, the compound 4-(5'-chloro-2'-fluorophenylamino)-6-[3-(2-methyl-2,8-diazaspiro[4.5]decane-3-ketone-8-yl)-propoxy]-7-methoxyquinazoline (3-2-24) was obtained.

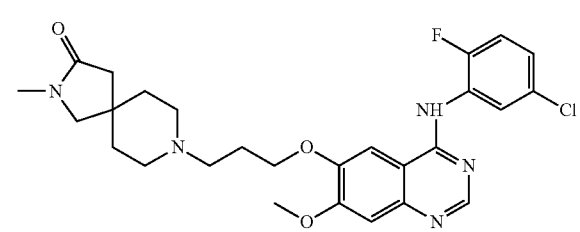 [SMILES: COc1cc2ncnc(Nc3cc(Cl)ccc3F)c2cc1OCCCN1CCC2(CC1)CC(=O)N(C)C2]

¹H NMR (CDCl₃) 8.72 (s, 1H), 8.44 (br, 1H), 7.99 (m, 1H), 7.49 (s, 1H), 7.30 (s, 1H), 7.10 (m, 2H), 4.35 (t, J=6.4 Hz, 2H), 4.04 (s, 3H), 3.23 (s, 2H), 2.95 (m, 2H), 2.87 (s, 3H), 2.69 (m, 2H), 2.30 (m, 4H), 2.05 (m, 3H), 1.84 (m, 3H). ES-MS (m/z): 528.0 (MH⁺).

Example 25

Using a procedure identical to that described in synthetic scheme 1, the compound 4-(5'-chloro-2'-fluorophenylamino)-6-[3-(1,8-diazaspiro[4.5]decane-2-ketone-8-yl)-propoxy]-7-methoxyquinazoline (3-2-25) was obtained.

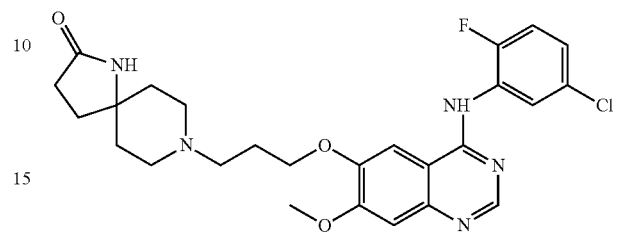

¹H NMR (CDCl₃) 8.71 (s, 1H), 8.40 (br, 1H), 7.50 (m, 1H), 7.30 (s, 1H) 7.10 (m, 2H), 4.35 (m, 2H), 4.03 (s, 3H), 3.02 (m, 4H), 2.42 (t, J=8.0 Hz, 2H), 2.32 (m, 2H), 2.00 ((t, J=8.0 Hz, 2H), 1.74 (m, 6H). ES-MS (m/z): 514.1 (MH⁺).

Example 26

Using a procedure identical to that described in synthetic scheme 1, the compound 4-(5'-chloro-2'-fluorophenylamino)-6-[3-(2-methyl-2,8-diazaspiro[4.5]decane-1-ketone-8-yl)-propoxy]-7-methoxyquinazoline (3-2-26) was obtained.

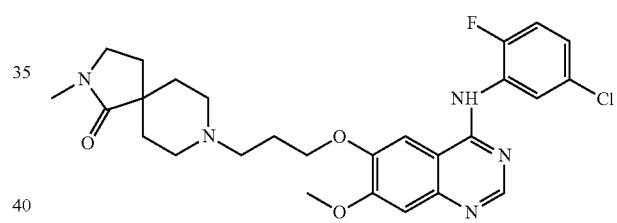

¹H NMR (CDCl₃) 8.70 (s, 1H), 8.35 (br, 1H), 8.04 (s, 1H), 7.74 (m, 1H), 7.11 (m, 2H), 4.40 (t, J=5.6 Hz, 2H), 4.04 (s, 3H), 3.46 (m, 2H), 3.35 (t, J=4.8 Hz, 2H), 3.05 (m, 2H), 2.86 (s, 3H), 2.38 (m, 2H), 1.97 (m, 4H), 1.72 (m, 4H). ES-MS (m/z): 528.0 (MH⁺).

Example 27

Using a procedure identical to that described in synthetic scheme 1, the compound 4-(5'-chloro-2'-fluorophenylamino)-6-[3-(2,6-diazaspiro[3.4]octane-7-ketone-2-yl)]-propoxy]-7-methoxyquinazoline (3-2-27) was obtained.

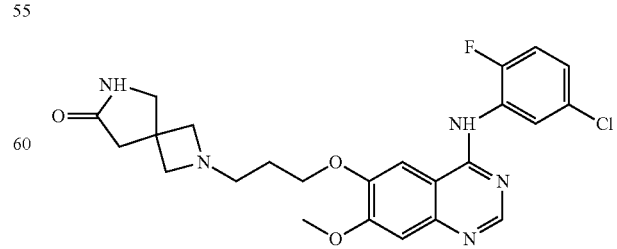

¹H NMR (CDCl₃) 8.75 (s, 1H), 8.61 (d, J=4.8 Hz, 1H), 8.04 (s, 1H), 7.68 (m, 1H), 7.10 (m, 2H), 5.53 (s, 1H), 4.30

(t, J=6.4 Hz, 2H), 4.04 (s, 3H), 3.69 (s, 2H), 3.61 (m, 2H), 3.45 (d, J=6.0 Hz, 2H), 2.90 (m, 2H), 2.58 (s, 2H), 2.09 (m, 2H). ES-MS (m/z): 486.0 (MH+).

Example 28

Using a procedure identical to that described in synthetic scheme 1, the compound 4-(3'-chloro-2'-fluorophenylamino)-6-[3-(2-oxa-6-azaspiro[3.4]octane-6-yl)-propoxy]-7-methoxyquinazoline (3-3-C) was obtained.

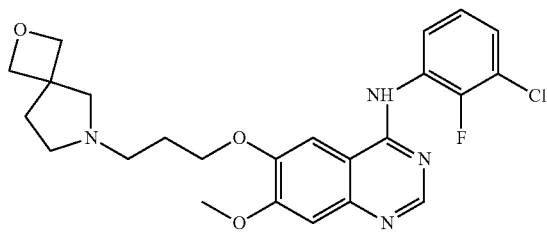 [SMILES: COc1cc2ncnc(Nc3cccc(Cl)c3F)c2cc1OCCCN1CCC2(COC2)C1]

$^1$H NMR (CDCl$_3$) 8.68 (s, 1H), 8.15 (t, J=6.4 Hz, 1H), 8.08 (br, 1H), 7.54 (s, 1H), 7.17 (m, 2H), 4.70 (dd, J=6.4 Hz, 4H), 4.38 (t, J=6.4 Hz, 2H), 4.03 (s, 3H), 3.28 (s, 2H), 3.02 (t, J=6.8 Hz, 4H), 2.35 (m, 2H), 2.28 (m, 2H). ES-MS (m/z): 473.3 (MH+).

Example 29

Using a procedure identical to that described in synthetic scheme 1, the compound 4-(3'-chloro-2'-fluorophenylamino)-6-[3-(2,7-diazaspiro[4.4]nonane-1-ketone-7-yl)-propoxy]-7-methoxyquinazoline (3-3-21) was obtained.

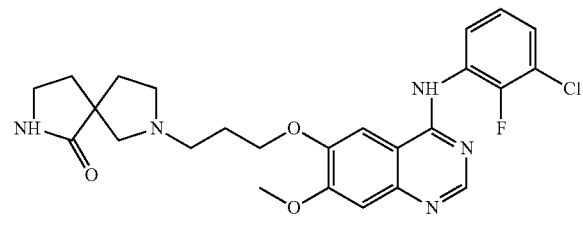 [SMILES: COc1cc2ncnc(Nc3cccc(Cl)c3F)c2cc1OCCCN1CCC2(CCNC2=O)C1]

$^1$H NMR (CDCl$_3$) 8.71 (s, 1H), 8.38 (br, 1H), 7.65 (br, 1H), 7.30 (s, 1H), 7.18 (m, 2H), 5.55 (s, 1H), 4.30 (t, J=6.4 Hz, 2H), 4.04 (s, 3H), 3.38 (d, J=9.6 Hz, 1H), 3.36 (d, J=9.6 Hz, 1H), 3.01 (m, 2H), 2.86 (m, 2H), 2.78 (m, 1H), 2.65 (m, 1H), 2.42 (d, J=5.6 Hz, 2H), 2.21 (t, J=6.8 Hz, 2H), 2.03 (m, 2H). ES-MS (m/z): 499.9 (MH+).

Example 30

Using a procedure identical to that described in synthetic scheme 1, the compound 4-(3'-chloro-2'-fluorophenylamino)-6-[3-(2-methyl-2,7-diazaspiro[4.4]nonane-1-ketone-7-yl)-propoxy]-7-methoxyquinazoline (3-3-22) was obtained.

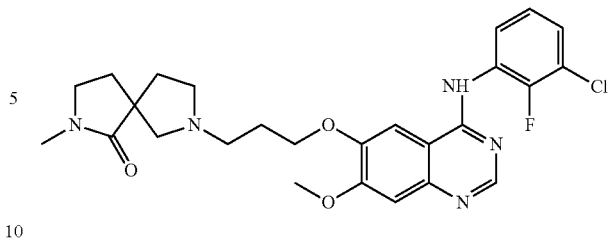

$^1$H NMR (CDCl$_3$) 8.64 (s, 1H), 8.45 (br, 1H), 7.98 (m, 1H), 7.80 (s, 1H), 7.17 (m, 1H), 7.13 (m, 1H), 4.51 (m, 1H), 4.46 (m, 1H), 4.04 (s, 3H), 3.35 (m, 3H), 3.10 (m, 3H), 2.84 (s, 3H), 2.30 (m, 4H), 2.26 (m, 2H), 2.15 (m, 2H). ES-MS (m/z): 514.3 (MH+).

Example 31

Using a procedure identical to that described in synthetic scheme 1, the compound 4-(3'-chloro-2'-fluorophenylamino)-6-[3-(2-methyl-2,8-diazaspiro[4.5]decane-3-ketone-8-yl)-propoxy]-7-methoxyquinazoline (3-3-24) was obtained.

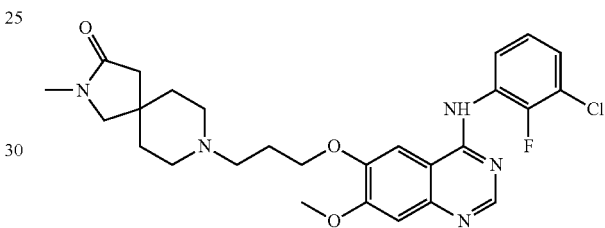

$^1$H NMR (CDCl$_3$) 8.70 (s, 1H), 8.33 (br, 1H), 7.72 (br, 1H), 7.33 (m, 1H), 7.18 (m, 2H), 4.31 (t, J=6.4 Hz, 2H), 4.04 (s, 3H), 3.20 (s, 2H), 2.86 (s, 3H), 2.78 (m, 2H), 2.56 (m, 2H), 2.31 (s, 2H), 2.24 (t, J=6.4 Hz, 2H), 1.88 (m, 4H), 1.78 (m, 2H). ES-MS (m/z): 527.8 (MH+).

Example 32

Using a procedure identical to that described in synthetic scheme 1, the compound 4-(3'-chloro-2'-fluorophenylamino)-6-[3-(1,8-diazaspiro[4.5]decane-2-ketone-8-yl)-propoxy]-7-methoxyquinazoline (3-3-25) was obtained.

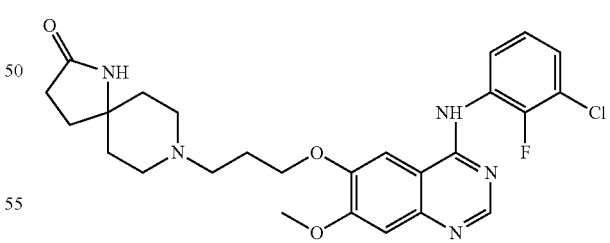

$^1$H NMR (CDCl$_3$) 8.67 (s, 1H), 8.28 (br, 1H), 7.86 (br, 1H), 7.39 (s, 1H), 7.18 (m, 2H), 4.31 (t, J=6.4 Hz, 2H), 4.04 (s, 3H), 2.80 (m, 4H), 2.41 (t, J=8.0 Hz, 2H), 2.25 (t, J=6.4 Hz, 2H)), 2.08 (m, 2H), 1.82 (m, 6H). ES-MS (m/z): 514.3 (MH+).

Example 33

Using a procedure identical to that described in synthetic scheme 1, the compound 4-(3'-chloro-2'-fluorophenylamino)-6-[3-(2,6-diazaspiro[3.4]octane-7-ketone-2-yl)]-propoxy]-7-methoxyquinazoline (3-3-27) was obtained.

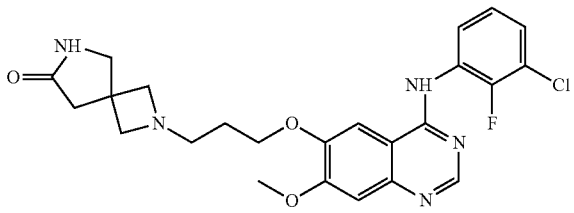 [SMILES: COc1cc2ncnc(Nc3cccc(Cl)c3F)c2cc1OCCCN1CC2(CNC(=O)C2)C1]

$^1$H NMR (CDCl$_3$) 8.72 (s, 1H), 8.47 (m, 1H), 7.42 (br, 1H), 7.31 (s, 1H), 7.18 (m, 2H), 5.48 (s, 1H), 4.25 (t, J=6.4 Hz, 2H), 4.05 (s, 3H), 3.62 (s, 2H), 3.39 (d, J=6.0 Hz, 2H), 3.28 (d, J=6.8 Hz, 2H), 2.74 (d, J=6.4 Hz, 2H), 2.55 (s, 2H), 2.02 (m, 2H). ES-MS (m/z): 485.8 (MH$^+$).

Example 34

Using a procedure identical to that described in synthetic scheme 1, the compound 4-(3'-chloro-2'-fluorophenylamino)-6-[3-(1-oxa-3,8-diazaspiro[4.5]decane-2-ketone-8-yl)-propoxy]-7-methoxyquinazoline (3-3-28) was obtained.

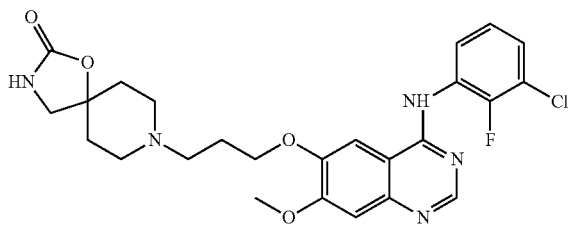 [SMILES: COc1cc2ncnc(Nc3cccc(Cl)c3F)c2cc1OCCCN1CCC2(CC1)CNC(=O)O2]

$^1$H NMR (CDCl$_3$) 8.70 (s, 1H), 8.36 (m, 1H), 7.69 (br, 1H), 7.30 (s, 1H), 7.18 (m, 2H), 5.10 (s, 1H), 4.31 (t, J=6.4 Hz, 2H), 4.04 (s, 3H), 3.38 (s, 2H), 2.90 (m, 2H), 2.79 (m, 4H), 2.24 (m, 2H), 2.05 (m, 4H). ES-MS (m/z): 516.3 (MH$^+$).

Example 35

Using a procedure identical to that described in synthetic scheme 1, the compound 4-(3'-chloro-2'-fluorophenylamino)-6-[3-(3-methyl-1-oxa-3,7-diazaspiro[4.4]nonane-2-ketone-7-yl)-propoxy]-7-methoxycquinazoline (3-3-30) was obtained.

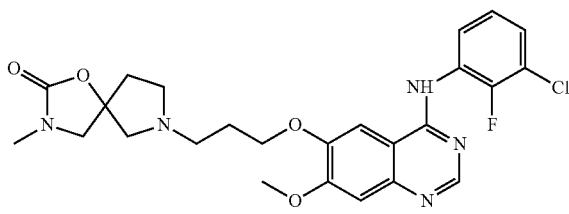 [SMILES: COc1cc2ncnc(Nc3cccc(Cl)c3F)c2cc1OCCCN1CCC2(C1)CN(C)C(=O)O2]

$^1$H NMR (CDCl$_3$) 8.71 (s, 1H), 8.39 (br, 1H), 7.51 (br, 1H), 7.31 (s, 1H), 7.19 (m, 2H), 4.29 (t, J=6.4 Hz, 2H), 4.05 (s, 3H), 3.59 (d, J=8.8 Hz, 1H), 3.52 (d, J=8.8 Hz, 1H), 2.98 (m, 2H), 2.90 (s, 3H), 2.83 (m, 3H), 2.35 (m, 1H), 2.18 (t, J=5.4 Hz, 2H), 2.05 (m, 2H). ES-MS (m/z): 515.8 (MH$^+$).

Example 36

Using a procedure identical to that described in synthetic scheme 1, the compound 4-(3'-chloro-2'-fluorophenylamino)-6-[3-(5-oxa-2,7-diazaspiro[3.4]octane-6-ketone-2-yl)-propoxy]-7-methoxyquinazoline (3-3-31) was obtained.

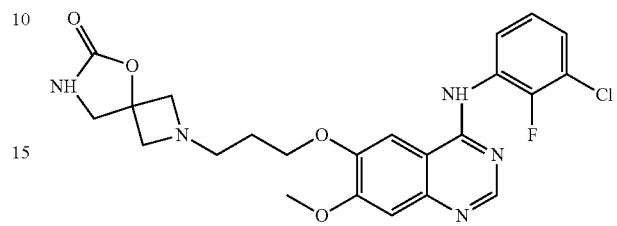

$^1$H NMR (CDCl$_3$) 8.72 (s, 1H), 8.48 (m, 1H), 7.41 (br, 1H), 7.30 (s, 1H), 7.17 (m, 2H), 7.11 (s, 1H), 5.00 (s, 1H), 4.23 (t, J=6.4 Hz, 2H), 4.05 (s, 3H), 3.89 (s, 2H), 3.61 (d, J=8.0 Hz, 2H), 3.47 (d, J=8.4 Hz, 2H), 2.80 (t, J=6.8 Hz, 2H), 2.03 (m, 2H). ES-MS (m/z): 487.8 (MH$^+$).

Example 37

Using a procedure identical to that described in synthetic scheme 1, the compound 4-(3'-chloro-2'-fluorophenylamino)-6-[3-(7-methyl-5-oxa-2,7-diazaspiro[3.4]octane-6-ketone-2-yl)-propoxy]-7-methoxyquinazoline (3-3-32) was obtained.

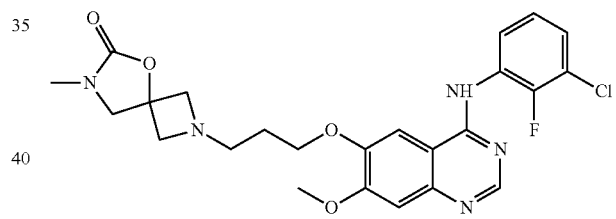

$^1$H NMR (CDCl$_3$) 8.72 (s, 1H), 8.48 (m, 1H), 7.40 (br, 1H), 7.31 (s, 1H), 7.18 (m, 2H), 7.12 (s, 1H), 4.24 (t, J=6.4 Hz, 2H), 4.04 (s, 3H), 3.78 (s, 2H), 3.61 (d, J=8.8 Hz, 2H), 3.44 (d, J=9.2 Hz, 2H), 2.90 (s, 3H), 2.80 (t, J=6.8 Hz, 2H), 2.03 (m, 2H). ES-MS (m/z): 501.8 (MH$^+$).

Example 38

Using a procedure identical to that described in synthetic scheme 1, the compound 4-(3'-ethynylphenylamino)-6-[3-(2-oxa-6-azaspiro[3.3]heptane-6-yl)-propoxy]-7-methoxyquinazoline (3-4-B) was obtained.

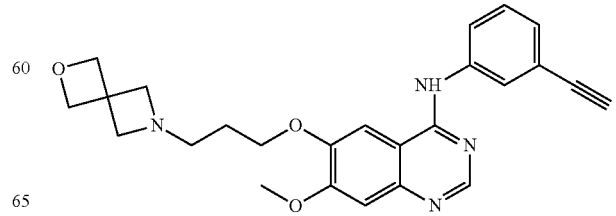

¹H NMR (CDCl₃) 8.69 (s, 1H), 7.98 (s, 2H), 7.86 (d d, J=8.8 Hz, 1H), 7.69 (br, 1H), 7.38 (d, J=8.0 Hz, 1H), 7.30 (s, 1H), 7.27 (s, 1H), 4.78 (s, 4H), 4.27 (t, J=6.4 Hz, 2H), 4.02 (s, 3H), 3.61 (s, 4H), 3.16 (s, 1H), 2.77 (t, J=6.4 Hz, 2H), 2.02 (m, 2H). ES-MS (m/z): 430.9 (MH⁺).

Example 39

Using a procedure identical to that described in synthetic scheme 1, the compound 4-(3'-ethynylphenylamino)-6-[3-(7-oxa-2-azaspiro[3.5]nonane-2-yl)-propoxy]-7-methoxy-quinazoline (3-4-F) was obtained.

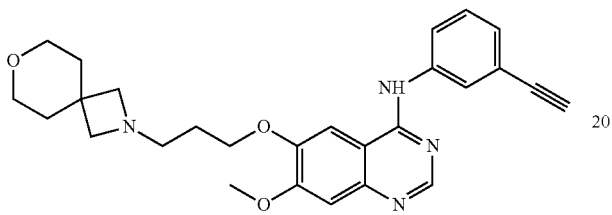

¹H NMR (CDCl₃) 8.84 (br, 1H), 8.67 (s, 1H), 8.23 (s, 1H), 7.99 (d, J=8.4 Hz, 1H), 7.35 (t, J=8.0 Hz, 2H), 7.24 (m, 2H), 4.51 (t, J=6.8 Hz, 2H), 4.01 (s, 3H), 3.80 (s, 4H), 3.58 (t, J=5.2 Hz, 4H), 3.26 (t, J=6.0 Hz, 2H), 3.09 (s, 1H), 2.21 (m, 2H), 1.96 (s, 4H). ES-MS (m/z): 458.9 (MH⁺).

Example 40

Using a procedure identical to that described in synthetic scheme 1, the compound 4-(3'-ethynylphenylamino)-6-[3-(2-oxa-7-azaspiro[4.4]-nonane-7-yl)-propoxy]-7-methoxy-quinazoline (3-4-H) was obtained.

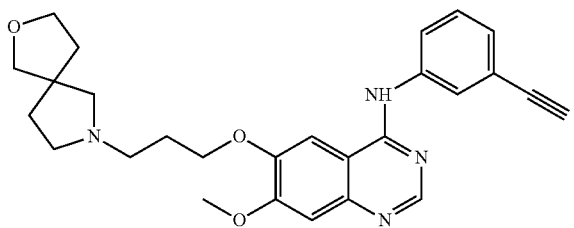 [SMILES: C#Cc1cccc(Nc2ncnc3cc(OC)c(OCCCN4CCC5(CCOC5)C4)cc23)c1]

¹H NMR (CDCl₃) 8.68 (s, 1H), 8.63 (br, 1H), 8.18 (s, 1H), 7.94 (m, 2H), 7.35 (t, J=6.4 Hz, 1H), 7.25 (m, 2H), 4.47 (t, J=6.8 Hz, 2H), 4.01 (s, 3H), 3.90 (m, 2H), 3.78 (d, J=8.8 Hz, 1H), 3.67 (d, J=8.8 Hz, 1H), 3.32 (m, 1H), 3.14 (m, 4H), 3.09 (s, 1H), 2.34 (m, 2H), 2.12 (m, 4H), 2.03 (m, 1H). ES-MS (m/z): 458.9 (MH⁺).

Example 41

Using a procedure identical to that described in synthetic scheme 1, the compound 4-(3'-ethynylphenylamino)-6-[3-(8-oxa-2-azaspiro[4.5]decane-2-yl)-propoxy]-7-methoxy-quinazoline (3-4-K) was obtained.

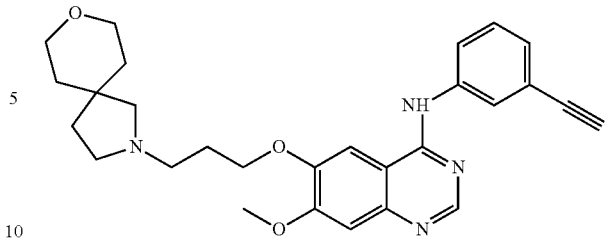

¹H NMR (CDCl₃) 8.78 (br, 1H), 8.67 (s, 1H), 8.18 (s, 1H), 7.96 (m, 2H), 7.34 (t, J=6.4 Hz, 1H), 7.25 (m, 2H), 4.46 (t, J=6.8 Hz, 2H), 4.00 (s, 3H), 3.64 (t, J=5.2 Hz, 4H), 3.26 (m, 2H), 3.17 (t, J=6.8 Hz, 2H), 3.08 (s, 1H), 3.04 (m, 2H), 2.34 (m, 2H), 2.05 (t, J=7.2 Hz, 2H), 1.73 (m, 4H). ES-MS (m/z): 472.9 (MH⁺).

Example 42

Using a procedure identical to that described in synthetic scheme 1, the compound 4-(3'-ethynylphenylamino)-6-[3-(3-oxa-8-azabicyclo[3.2.1]octane-8-yl)-propoxy]-7-methoxyquinazoline (3-4-O) was obtained.

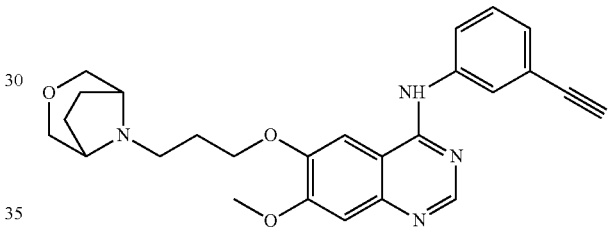

¹H NMR (CDCl₃) 8.69 (s, 1H), 8.04 (s, 1H), 7.95 (s, 1H), 7.85 (d, J=7.6 Hz, 1H), 7.38 (t, J=8.0 Hz, 1H), 7.30 (s, 1H), 7.24 (s, 1H), 4.36 (m, 2H), 4.23 (t, J=6.4 Hz, 2H), 4.02 (s, 3H), 3.11 (s, 1H), 2.84 (m, 2H), 2.71 (m, 2H), 2.52 (d, J=10.8 Hz, 2H), 2.16 (m, 2H), 2.09 (m, 2H), 1.93 (m, 2H). ES-MS (m/z): 444.9 (MH⁺).

Example 43

Using a procedure identical to that described in synthetic scheme 1, the compound 4-(3'-ethynylphenylamino)-6-[3-(2,8-diazaspiro[4.5]decane-3-ketone-8-yl)-propoxy]-7-methoxyquinazoline (3-4-P) was obtained.

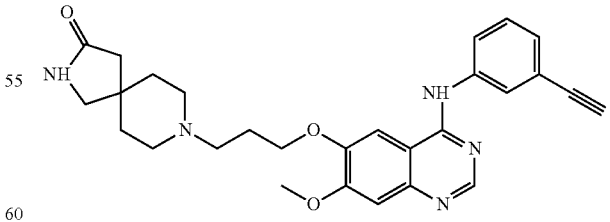

¹H NMR (CDCl₃) 8.69 (s, 1H), 8.03 (m, 1H), 7.89 (d, J=8.0 Hz, 1H), 7.53 (m, 1H), 7.38 (t, J=8.0 Hz, 1H), 7.30 (s, 1H), 7.24 (s, 1H), 5.51 (m, 1H), 4.33 (t, J=6.4 Hz, 2H), 4.03 (s, 3H), 3.23 (s, 2H), 3.11 (s, 1H), 2.84 (m, 2H), 2.62 (m, 2H), 2.26 (m, 4H), 1.97 (m, 2H), 1.84 (m, 4H). ES-MS (m/z): 485.9 (MH⁺).

Example 44

Using a procedure identical to that described in synthetic scheme 1, the compound 4-(3'-ethynylphenylamino)-6-[3-(2-methyl-2,8-diazaspiro[4.5]decane-3-ketone-8-yl) propoxy]-7-methoxyquinazoline (3-4-26) was obtained.

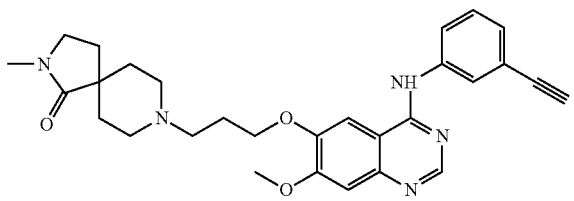 [SMILES: C#Cc1cccc(Nc2ncnc3cc(OC)c(OCCCN4CCC5(CC4)CCN(C)C5=O)cc23)c1]

$^1$H NMR (CDCl$_3$) 8.98 (br, 1H), 8.66 (s, 1H), 8.21 (s, 1H), 8.06 (m, 1H), 7.79 (d, J=8.0 Hz, 1H), 7.34 (d, J=7.6 Hz, 1H), 7.24 (s, 1H), 4.50 (t, J=6.4 Hz, 2H), 4.01 (s, 3H), 3.58 (m, 2H), 3.35 (t, J=6.8 Hz, 2H), 3.23 (m, 2H), 3.17 (m, 2H), 3.08 (s, 1H), 2.85 (s, 3H), 2.39 (t, J=6.8 Hz, 2H), 2.28 (m, 2H), 1.95 (m, 4H). ES-MS (m/z): 500.1 (MH$^+$).

Example 45

Using a procedure identical to that described in synthetic scheme 1, the compound 4-(3'-ethynylphenylamino)-6-[3-(2,6-diazaspiro[3.4]octane-7-ketone-2-yl)-propoxy]-7-methoxyquinazoline (3-4-27) was obtained.

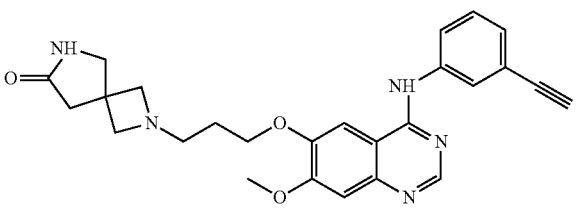 [SMILES: C#Cc1cccc(Nc2ncnc3cc(OC)c(OCCCN4CC5(CNC(=O)C5)C4)cc23)c1]

$^1$H NMR (CDCl$_3$) 8.70 (s, 1H), 7.91 (s, 1H), 7.84 (d, J=7.6 Hz, 1H), 7.54 (s, 1H), 7.39 (t, J=7.6 Hz, 1H), 7.28 (s, 1H), 7.24 (s, 1H), 5.57 (s, 1H), 4.24 (t, J=6.8 Hz, 2H), 4.03 (s, 3H), 3.62 (s, 2H), 3.41 (d, J=7.6 Hz, 2H), 3.30 (d, J=7.6 Hz, 2H), 3.31 (s, 1H), 2.75 (t, J=6.4 Hz, 2H), 2.55 (s, 2H), 2.02 (t, J=6.4 Hz, 2H). ES-MS (m/z): 457.8 (MH$^+$).

Example 46

Using a procedure identical to that described in synthetic scheme 1, the compound 4-(3'-ethynylphenylamino)-6-[3-(1-oxa-3,8-diazaspiro[4.5]decane-2-ketone-8-yl)-propoxy]-7-methoxyquinazoline (3-4-28) was obtained.

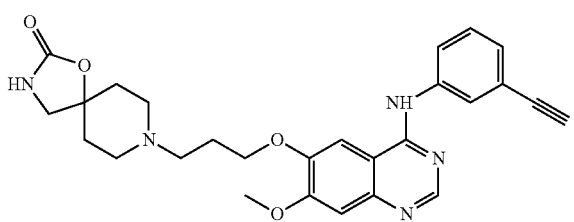

$^1$H NMR (CDCl$_3$) 8.69 (s, 1H), 7.97 (s, 1H), 7.87 (d, J=7.2 Hz, 2H), 7.43 (m, 2H), 7.39 (t, J=8.0 Hz, 1H), 5.04 (s, 1H), 4.30 (t, J=6.8 Hz, 2H), 4.02 (s, 3H), 3.37 (s, 2H), 3.11 (s, 1H), 2.90 (m, 2H), 2.76 (m, 4H), 2.22 (t, J=6.8 Hz, 2H), 2.02 (m, 4H). ES-MS (m/z): 487.9 (MH$^+$).

Example 47

Using a procedure identical to that described in synthetic scheme 1, the compound 4-(3'-ethynylphenylamino)-6-[3-(3-methyl-1-oxa-3,7-diazaspiro[4.4]nonane-2-ketone-7-yl)-propoxy]-7-methoxyquinazoline (3-4-30) was obtained.

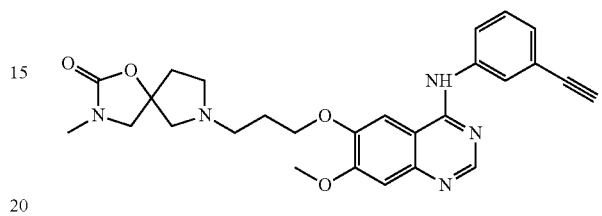

$^1$H NMR (CDCl$_3$) 8.67 (s, 1H), 7.94 (s, 1H), 7.84 (m, 2H), 7.37 (m, 2H), 7.28 (s, 1H), 4.26 (t, J=6.8 Hz, 2H), 4.02 (s, 3H), 3.52 (q, J=9.2 Hz, 2H), 3.10 (s, 1H), 3.03 (m, 2H), 2.89 (s, 3H), 2.85 (m, 4H), 2.32 (m, 1H), 2.13 (m, 3H). ES-MS (m/z): 487.9 (MH$^+$).

Example 48

Using a procedure identical to that described in synthetic scheme 1, the compound 4-(3'-ethynylphenylamino)-6-[3-[(5-oxa-2,7-diazaspiro[3.4]octane-6-ketone-2-yl)-propoxy]-7-methoxyquinazoline (3-4-31) was obtained.

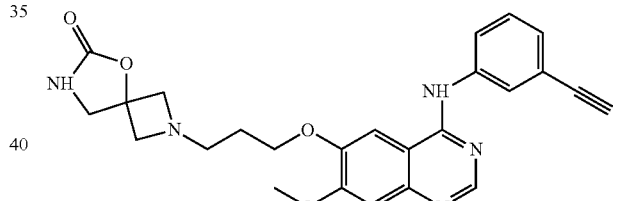

$^1$H NMR (CDCl$_3$) 8.69 (s, 1H), 7.89 (s, 1H), 7.83 (d, J=8.4 Hz, 1H), 7.63 (s, 1H), 7.38 (m, 1H), 7.30 (m, 1H), 7.23 (s, 1H), 5.26 (s, 1H), 4.20 (t, J=6.8 Hz, 2H), 4.02 (s, 3H), 3.81 (s, 2H), 3.51 (dd, J=8.8 Hz, 4H), 3.12 (s, 1H), 2.77 (t, J=6.4 Hz, 2H), 2.01 (m, 2H). ES-MS (m/z): 459.9 (MH$^+$).

Example 49

Using a procedure identical to that described in synthetic scheme 1, the compound 4-(3'-ethynylphenylamino)-6-[3-[(7-methyl-5-oxa-2,7-diazaspiro[3.4]octane-6-ketone-2-yl)-propoxy]-7-methoxyquinazoline (3-4-32) was obtained.

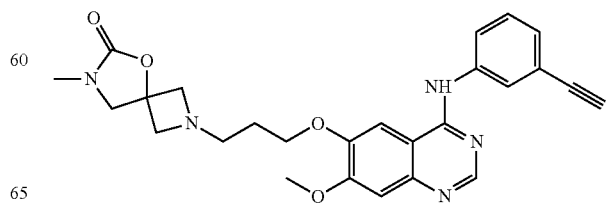

¹H NMR (CDCl₃) 8.70 (s, 1H), 7.88 (s, 1H), 7.82 (d, J=8.4 Hz, 1H), 7.40 (m, 3H), 7.15 (s, 1H), 4.22 (t, J=6.4 Hz, 2H), 4.03 (s, 3H), 3.75 (s, 2H), 3.58 (d, J=8.8 Hz, 2H), 3.46 (d, J=8.8 Hz, 2H), 3.13 (s, 1H), 2.88 (s, 3H), 2.78 (t, J=6.8 Hz, 2H), 2.02 (m, 2H). ES-MS (m/z): 473.9 (MH⁺).

Example 50

Using a procedure identical to that described in synthetic scheme 1, the compound 4-(3'-ethynylphenylamino)-6-[3-(cis-hexahydrofuro[3,2-b]pyrrole-4-yl)-propoxy]-7-methoxyquinazoline (3-4-11) was obtained.

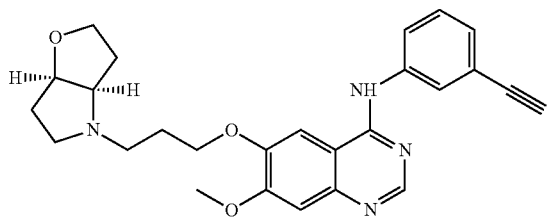 [SMILES: C#Cc1cccc(Nc2ncnc3cc(OC)c(OCCCN4CC[C@H]5OCC[C@H]54)cc23)c1]

¹H NMR (CDCl₃) 8.70 (s, 1H), 7.97 (s, 1H), 7.83 (d, J=8.4 Hz, 1H), 7.70 (br, 1H), 7.38 (t, J=8.0 Hz, 1H), 7.34 (s, 1H), 7.30 (s, 1H), 4.58 (m, 1H), 4.29 (m, 2H), 4.03 (s, 3H), 3.90 (m, 1H), 3.78 (m, 1H), 3.36 (m, 1H), 3.17 (m, 1H), 3.11 (s, 1H), 3.02 (m, 1H), 2.69 (m, 1H), 2.49 (m, 1H), 2.20 (m, 2H), 2.05 (m, 2H), 1.93 (m, 2H). ES-MS (m/z): 444.8 (MH⁺).

Example 51

Using a procedure identical to that described in synthetic scheme 1, the compound 4-(3'-ethynylphenylamino)-6-[3-(7-acetyl-2,7-diazaspiro[4.4]-nonane-2-yl)-propoxy]-7-methoxyquinazoline (3-4-7) was obtained.

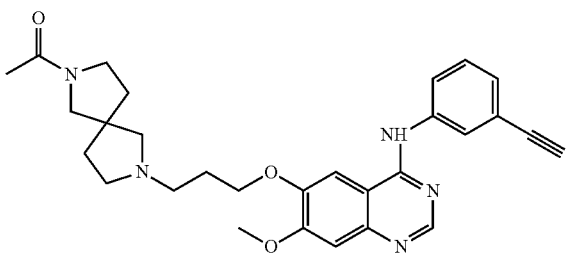 [SMILES: C#Cc1cccc(Nc2ncnc3cc(OC)c(OCCCN4CCC5(CCN(C(C)=O)C5)C4)cc23)c1]

¹H NMR (CDCl₃) 8.68 (d, J=6.8 Hz, 1H), 8.44 (br, 1H), 8.00 (m, 1H), 7.87 (d, J=8.4 Hz, 1H), 7.55 (s, 1H), 7.36 (t, J=6.0 Hz, 1H), 7.26 (s, 1H), 4.28 (m, 2H), 4.02 (s, 3H), 3.73 (d, J=11.2 Hz, 1H), 3.50 (m, 3H), 3.39 (d, J=10.0 Hz, 1H), 3.26 (d, J=12.0 Hz, 1H), 3.10 (s, 1H), 2.87 (m, 1H), 2.79 (m, 1H), 2.67 (m, 2H), 2.19 (m, 2H), 2.05 (m, 5H), 1.89 (m, 2H). ES-MS (m/z): 499.8 (MH⁺).

Example 52

Using a procedure identical to that described in synthetic scheme 1, the compound 4-(3'-chloro-4'-fluorophenylamino)-6-[2-(7-methyl-2,7-diazaspiro[4.4]nonane-2-yl)-oxethyl]-7-methoxyquinazoline (2-C-1) was obtained.

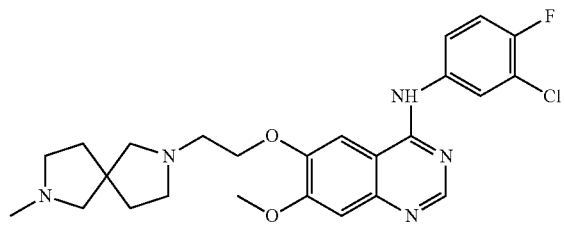 [SMILES: COc1cc2ncnc(Nc3ccc(F)c(Cl)c3)c2cc1OCCN1CCC2(CCN(C)C2)C1]

¹H NMR (CDCl₃) 8.95 (s, 1H), 8.63 (s, 1H), 8.16 (m, 1H), 8.02 (s, 1H), 7.86 (m, 1H), 7.24 (s, 2H), 7.14 (t, J=8.8 Hz, 1H), 4.45 (m, 2H), 4.02 (s, 3H), 3.63 (m, 2H), 3.52 (m, 2H), 3.25 (m, 1H), 3.06 (m, 1H), 2.90 (m, 2H), 2.74 (s, 3H), 2.58 (m, 2H), 2.37 (s, 2H), 2.10 (m, 2H). ES-MS (m/z): 486.3 (MH⁺).

Example 53

Using a procedure identical to that described in synthetic scheme 1, the compound 4-(3'-chloro-4'-fluorophenylamino)-6-[3-(7-oxa-2-azaspiro[3.5]nonane-2-yl)-oxethyl]-7-methoxyquinazoline (2-C—F) was obtained.

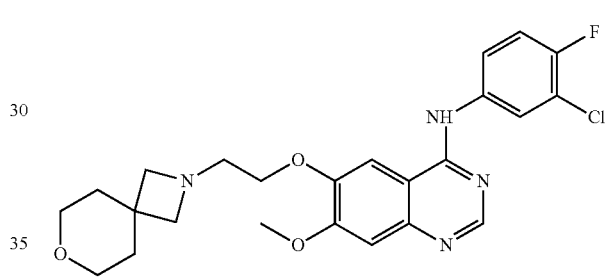

¹H NMR (CDCl₃) 8.67 (s, 1H), 7.95 (dd, J=2.4, 2.4 Hz, 1H), 7.80 (s, 1H), 7.65 (m, 1H), 7.23 (s, 1H), 7.19 (t, J=8.8 Hz, 1H), 4.27 (t, J=6.0 Hz, 2H), 4.04 (s, 3H), 3.62 (t, J=5.2 Hz, 4H), 3.27 (s, 4H), 3.07 (t, J=5.2 Hz, 2H), 1.81 (t, J=5.2 Hz, 4H). ES-MS (m/z): 473.3 (MH⁺).

Example 54

Using a procedure identical to that described in synthetic scheme 1, the compound 4-(3'-chloro-4'-fluorophenylamino)-)-6-[3-(cis-hexahydrofuro[3,2-b]pyrrole-4-yl)-propoxy]-7-methoxyquinazoline (2-C-11) was obtained.

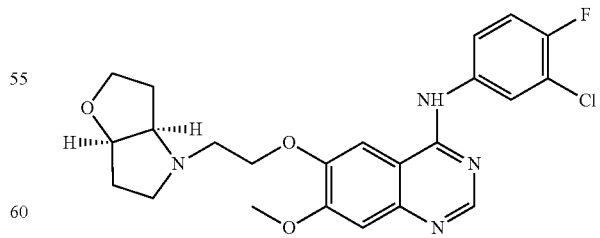

¹H NMR (CDCl₃) 8.67 (s, 1H), 7.95 (m, 1H), 7.59 (m, 2H), 7.39 (s, 1H), 7.19 (t, J=8.8 Hz, 1H), 4.58 (m, 1H), 4.37 (m, 2H), 4.03 (s, 3H), 3.97 (m, 1H), 3.84 (m, 1H), 3.35 (m, 1H), 3.21 (m, 2H), 2.98 (m, 1H), 2.53 (m, 1H), 2.16 (m, 1H), 1.93 (m, 3H). ES-MS (m/z): 458.8 (MH⁺).

Example 55

Using a procedure identical to that described in synthetic scheme 1, the compound 4-(3'-chloro-4'-fluorophenylamino)-6-[2-(2,7-diazaspiro[4.4]-nonane-1-ketone-7-yl)-oxethyl]-7-methoxyquinazoline (2-C-21) was obtained.

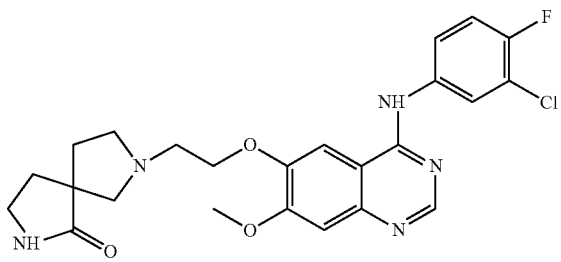 [SMILES: COc1cc2ncnc(Nc3ccc(F)c(Cl)c3)c2cc1OCCN1CCC2(CCNC2=O)C1]

$^1$H NMR (CDCl$_3$) 8.68 (s, 1H), 7.93 (m, 1H), 7.58 (m, 2H), 7.24 (s, 1H), 7.19 (t, J=8.8 Hz, 1H), 5.56 (s, 1H), 4.31 (t, J=6.4 Hz, 2H), 4.03 (s, 3H), 3.38 (m, 2H), 3.07 (t, J=6.0 Hz, 1H), 2.98 (m, 2H), 2.90 (m, 2H), 2.85 (d, J=9.6 Hz, 1H), 2.44 (m, 2H), 2.01 (t, J=6.8 Hz, 2H). ES-MS (m/z): 485.9 (MH$^+$).

Example 56

Using a procedure identical to that described in synthetic scheme 1, the compound 4-(3'-chloro-4'-fluorophenylamino)-6-[2-(2-methyl-2,8-diazaspiro[4.5]decane-2-ketone-8-yl)-oxethyl]-7-methoxyquinazoline (2-C-24) was obtained.

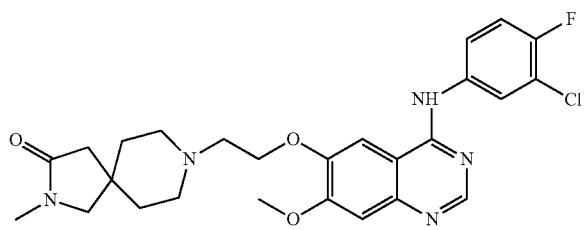 [SMILES: COc1cc2ncnc(Nc3ccc(F)c(Cl)c3)c2cc1OCCN1CCC2(CC1)CC(=O)N(C)C2]

$^1$H NMR (CDCl$_3$) 8.67 (s, 1H), 7.98 (m, 1H), 7.89 (s, 1H), 7.65 (m, 1H), 7.46 (s, 1H), 7.18 (t, J=8.8 Hz, 1H), 4.44 (t, J=6.4 Hz, 2H), 4.02 (s, 3H), 3.21 (s, 2H), 3.02 (t, J=6.4 Hz, 2H), 2.90 (s, 3H), 2.87 (m, 2H), 2.62 (m, 2H), 2.32 (s, 2H), 1.80 (m, 4H). ES-MS (m/z): 513.9 (MH$^+$).

Example 57

Using a procedure identical to that described in synthetic scheme 1, the compound 4-(3'-chloro-4'-fluorophenylamino)-6-[2-(2,6-diazaspiro[3.4]octane-7-ketone-2-yl)-oxethyl]-7-m ethoxyquinazoline (2-C-27) was obtained.

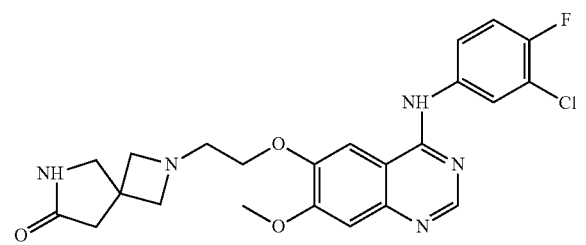 [SMILES: COc1cc2ncnc(Nc3ccc(F)c(Cl)c3)c2cc1OCCN1CC2(CNC(=O)C2)C1]

$^1$H NMR (CDCl$_3$) 8.68 (s, 1H), 7.94 (m, 1H), 7.54 (s, 1H), 7.41 (m, 1H), 7.17 (m, 1H), 7.02 (s, 1H), 5.55 (s, 1H), 4.24 (m, 2H), 4.04 (s, 3H), 3.64 (s, 2H), 3.52 (m, 2H), 3.08 (m, 2H), 2.58 (s, 2H), 2.12 (m, 2H). ES-MS (m/z): 471.9 (MH$^+$).

Example 58

Using a procedure identical to that described in synthetic scheme 1, the compound 4-(3'-chloro-4'-fluorophenylamino)-6-[2-(1-oxa-3,8-diazaspiro[4.5]decane-2-ketone-8-yl)-oxethyl]-7-methoxyquinazoline (2-C-28) was obtained.

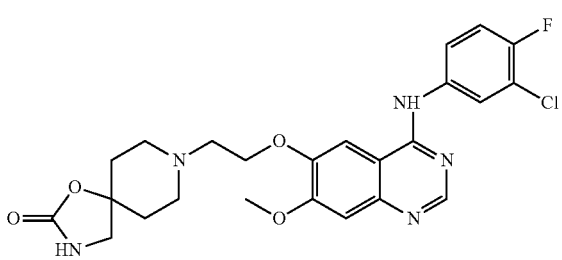 [SMILES: COc1cc2ncnc(Nc3ccc(F)c(Cl)c3)c2cc1OCCN1CCC2(CC1)CNC(=O)O2]

$^1$H NMR (CDCl$_3$) 8.68 (s, 1H), 7.93 (d, J=4.0 Hz, 1H), 7.62 (m, 2H), 7.35 (m, 1H), 7.19 (t, J=8.8 Hz, 1H), 4.92 (s, 1H), 4.39 (m, 2H), 4.04 (s, 3H), 3.39 (s, 2H), 3.04 (t, J=6.8 Hz, 2H), 2.87 (m, 2H), 2.78 (m, 2H), 2.08 (m, 2H), 1.92 (m, 2H). ES-MS (m/z): 501.8 (MH$^+$).

Example 59

Using a procedure identical to that described in synthetic scheme 1, the compound 4-(3'-chloro-4'-fluorophenylamino)-6-[2-(3-methyl-1-oxa-3,7-diazaspiro[4.4]nonane-2-ketone-7-yl)-oxethyl]-7-methoxyquinazoline (2-C-30) was obtained.

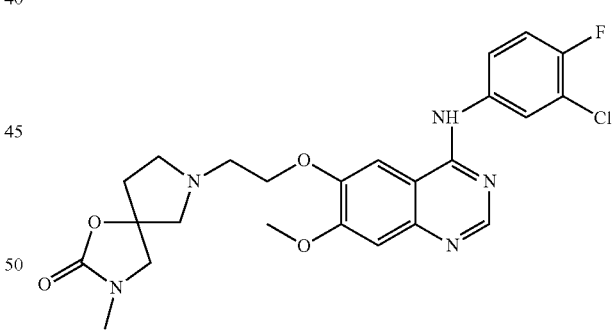

$^1$H NMR (CDCl$_3$) 8.67 (s, 1H), 8.15 (s, 1H), 7.97 (m, 1H), 7.62 (m, 1H), 7.45 (s, 2H), 7.18 (t, J=8.8 Hz, 1H), 4.31 (d, J=4.0 Hz, 2H), 4.01 (s, 3H), 3.55 (d, J=4.0 Hz, 2H), 3.18 (d, J=10.8 Hz, 1H), 3.08 (m, 3H), 2.90 (s, 3H), 2.85 (m, 2H), 2.36 (m, 1H), 2.08 (m, 1H). ES-MS (m/z): 501.8 (MH$^+$).

Example 60

Using a procedure identical to that described in synthetic scheme 1, the compound 4-(3'-chloro-4'-fluorophenylamino)-6-[2-(5-oxa-2,7-diazaspiro[3.4]octane-6-ketone-2-yl)-oxethyl]-7-methoxyquinazoline (2-C-31) was obtained.

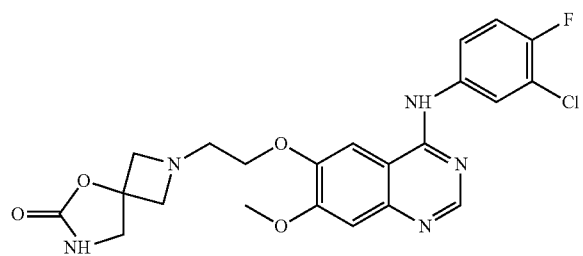 [SMILES: COc1cc2ncnc(Nc3ccc(F)c(Cl)c3)c2cc1OCCN1CC2(CNC(=O)O2)C1]

¹H NMR (CDCl₃)) 8.68 (s, 1H), 7.96 (m, 1H), 7.60 (m, 2H), 7.25 (s, 1H), 7.17 (m, 1H), 4.95 (s, 1H), 4.25 (t, J=5.2 Hz, 2H), 4.04 (s, 3H), 3.87 (s, 2H), 3.71 (m, 4H), 3.12 (m, 2H). ES-MS (m/z): 473.8 (MH⁺).

Example 61

Using a procedure identical to that described in synthetic scheme 1, the compound 4-(3'-chloro-4'-fluorophenylamino)-6-[2-(7-methyl-5-oxa-2,7-diazaspiro[3.4]octane-6-ketone-2-yl)-oxethyl]-7-methoxyquinazoline (2-C-32) was obtained.

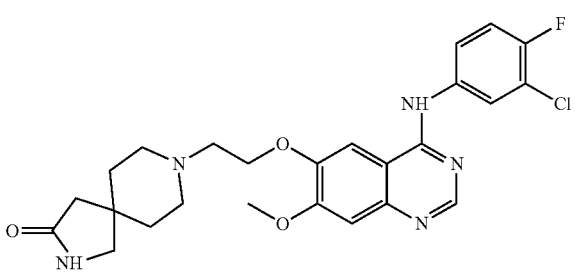 [SMILES: COc1cc2ncnc(Nc3ccc(F)c(Cl)c3)c2cc1OCCN1CCC2(CC1)CNC(=O)C2]

¹H NMR (CDCl₃) 8.67 (s, 1H), 7.94 (m, 1H), 7.58 (m, 2H), 7.20 (m, 2H), 4.22 (t, J=5.2 Hz, 2H), 4.02 (s, 3H), 3.77 (s, 2H), 3.64 (m, 4H), 3.07 (t, J=5.2 Hz, 2H), 2.89 (s, 3H). ES-MS (m/z): 487.8 (MH⁺).

Example 62

Using a procedure identical to that described in synthetic scheme 1, the compound 4-(3'-chloro-4'-fluorophenylamino)-6-[2-(2-oxa-6-azaspiro[3.3]heptane-6-yl)-oxethyl]-7-methoxyquinazoline (2-C—B) was obtained.

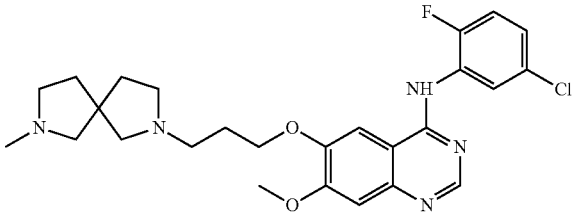 [SMILES: COc1cc2ncnc(Nc3cc(Cl)ccc3F)c2cc1OCCCN1CCC2(CCN(C)C2)C1]

¹H NMR (CDCl₃) 8.67 (s, 1H), 7.92 (q, J=2.8 Hz, 1H), 7.57 (m, 1H), 7.45 (s, 1H), 7.19 (t, J=8.8 Hz, 2H), 4.78 (s, 4H), 4.19 (t, J=5.6 Hz, 2H), 4.04 (s, 3H), 3.56 (s, 4H), 2.95 (t, J=5.6 Hz, 2H). ES-MS (m/z): 445.2 (MH⁺).

Example 63

Using a procedure identical to that described in synthetic scheme 1, the compound 4-(3'-chloro-4'-fluorophenylamino)-6-[2-(2,8-diazaspiro[4.5]decane-3-ketone-8-yl)-oxethyl]-7-methoxyquinazoline (2-C—P) was obtained.

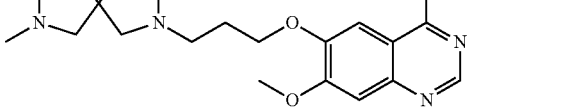

¹H NMR (CDCl₃) 8.68 (s, 1H), 8.44 (m, 1H), 8.27 (m, 1H), 7.85 (m, 1H), 7.54 (s, 1H), 7.17 (t, J=8.8 Hz, 1H), 5.51 (s, 1H), 4.98 (m, 2H), 4.02 (s, 3H), 3.62 (m, 1H), 3.40 (m, 2H), 3.33 (s, 2H), 2.98 (m, 1H), 2.34 (s, 2H), 2.08 (m, 2H), 1.63 (m, 4H). ES-MS (m/z): 500.3 (MH⁺).

Example 64

Using a procedure identical to that described in synthetic scheme 1, the compound 4-(5'-chloro-22'-fluorophenylamino)-6-[3-(7-methyl-2,7-diazaspiro[4.4]nonane-2-yl)-propoxy]-7-methoxyquinazoline (3-2-1) was obtained.

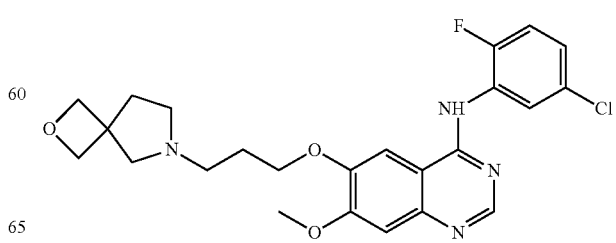

¹H NMR (CDCl₃) 7.98 (br, 1H), 7.67 (s, 1H), 7.12 (s, 1H), 6.90 (q, J=8.8 Hz, 2H), 6.60 (m, 2H), 4.48 (s, 1H), 4.25 (t, J=6.4 Hz, 2H), 4.16 (t, J=6.4 Hz, 2H), 4.00 (s, 3H), 3.80 (t, J=6.4 Hz, 2H), 3.73 (t, J=6.4 Hz, 1H), 3.67 (t, J=6.4 Hz, 1H), 3.58 (m, 2H), 3.52 (t, J=6.4 Hz, 1H), 2.33 (m, 5H), 1.62 (m, 2H), 1.40 (m, 2H). ES-MS (m/z): 500.1 (MH⁺).

Example 65

Using a procedure identical to that described in synthetic scheme 1, the compound 4-(5'-chloro-2'-fluorophenylamino)-6-[3-(2-oxa-6-azaspiro[3.4]octane-6-yl)-propoxy-7-methoxyquinazoline (3-2-C) was obtained.

¹H NMR (CDCl₃) 8.72 (s, 1H), 8.47 (d, J=6.8 Hz, 1H), 7.91 (br, 1H), 7.45 (s, 1H), 7.30 (s, 1H), 7.09 (m, 2H), 4.70 (dd, J=6.4, 6.4 Hz, 4H), 4.37 (t, J=6.4 Hz, 2H), 4.04 (s, 3H), 3.26 (s, 2H), 3.00 (m, 4H), 2.38 (t, J=6.4 Hz, 2H), 2.31 (t, J=6.8 Hz, 2H). ES-MS (m/z): 473.2 (MH⁺).

Example 66

Using a procedure identical to that described in synthetic scheme 1, the compound 4-(5'-chloro-2'-fluorophenylamino)-6-[3-(2,8-diazaspiro[4.5]-decane-3-ketone-8-yl)-propoxy]-7-methoxyquinazoline (3-2-P) was obtained.

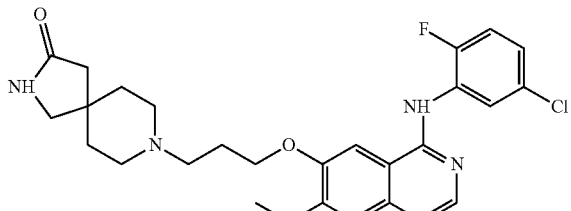

¹H NMR (CDCl₃) 8.75 (s, 1H), 8.65 (m, 1H), 8.04 (s, 1H), 7.31 (s, 1H), 7.25 (m, 1H), 7.12 (q, J=8.4 Hz, 1H), 7.06 (m, 1H), 4.30 (t, J=6.4 Hz, 2H), 4.05 (s, 3H), 3.23 (s, 2H), 2.77 (m, 3H), 2.56 (m, 2H), 2.25 (s, 4H), 1.82 (m, 5H). ES-MS (m/z): 513.8 (MH⁺).

Example 67

Using a procedure identical to that described in synthetic scheme 1, the compound 4-(5'-chloro-2'-fluorophenylamino)-6-[3-(7-methyl-2,7-diazaspiro[4.4]-nonane-2-yl)-propoxy]-7-methoxyquinazoline (3-3-1) was obtained.

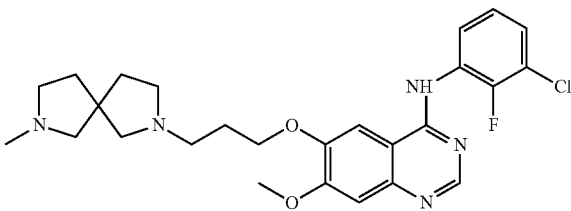 [SMILES: COc1cc2ncnc(Nc3cccc(Cl)c3F)c2cc1OCCCN1CCC2(CCN(C)C2)C1]

¹H NMR (CDCl₃) 8.63 (s, 1H), 8.04 (s, 1H), 7.95 (m, 1H), 7.84 (m, 1H), 7.23 (m, 1H), 7.15 (m, 1H), 4.38 (m, 2H), 4.04 (s, 3H), 3.64 (s, 2H), 3.52 (m, 2H), 3.08 (m, 2H), 2.58 (s, 3H), 2.24 (m, 2H), 2.12 (m, 4H), 1.86 (m, 4H). ES-MS (m/z): 500.1 (MH⁺).

Example 68

Using a procedure identical to that described in synthetic scheme 1, the compound 4-(3'-ethynylphenylamino)-6-[3-(7-methyl-2,7-diazaspiro[4.4]nonyl)-propoxy]-7-methoxyquinazoline (3-4-1) was obtained.

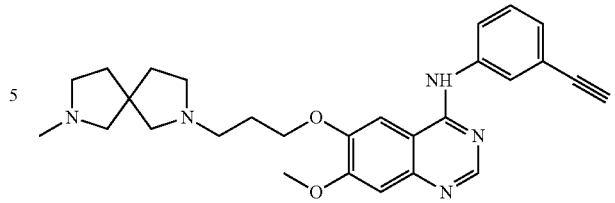

¹H NMR (CDCl₃) 9.04 (s, 1H), 8.66 (s, 1H), 8.24 (s, 1H), 8.13 (s, 1H), 7.96 (m, 1H), 7.34 (m, 1H), 7.24 (m, 1H), 4.49 (t, J=6.8 Hz, 2H), 4.00 (s, 3H), 3.16 (m, 3H), 2.90 (s, 3H), 2.43 (m, 4H), 2.04 (m, 5H), 1.67 (m, 4H). ES-MS (m/z): 471.9 (MH⁺).

Example 69

Using a procedure identical to that described in synthetic scheme 1, the compound 4-(3'-ethynylphenylamino)-6-[3-(2,8-diazaspiro[4.5]decane-3-ketone-8-yl)-propoxy]-7-methoxyquinazoline (3-4-20) was obtained.

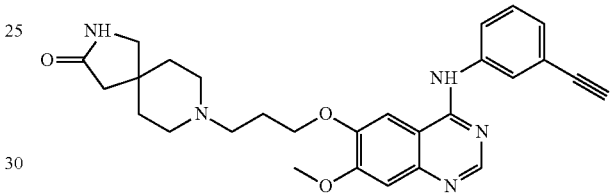

¹H NMR (CDCl₃) 8.69 (s, 1H), 8.00 (s, 1H), 7.87 (d, J=8.0 Hz, 2H), 7.48 (br, 1H), 7.38 (t, J=8.0 Hz, 1H), 7.30 (s, 1H), 5.50 (s, 1H), 4.32 (m, 2H), 4.03 (s, 3H), 3.23 (s, 2H), 3.12 (s, 1H), 2.81 (m, 4H), 2.59 (m, 2H), 2.26 (s, 4H), 1.94 (m, 4H). ES-MS (m/z): 485.9 (MH⁺).

Example 70

Using a procedure identical to that described in synthetic scheme 1, the compound 4-(3'-ethynylphenylamino)-6-[3-(2,7-diazaspiro[4.4]-nonane-1-ketone-7-yl)-propoxy]-7-methoxyquinazoline (3-4-21) was obtained.

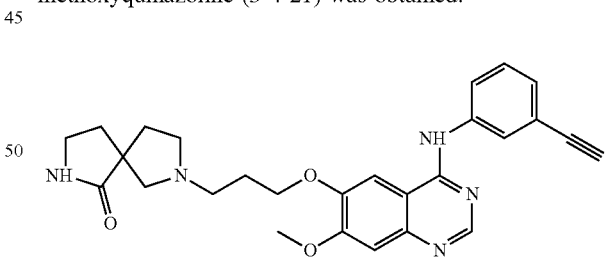

¹H NMR (CDCl₃) 8.66 (s, 1H), 8.54 (s, 1H), 8.17 (br, 1H), 7.92 (d, J=6.4 Hz, 1H), 7.68 (m, 1H), 7.37 (m, 2H), 5.60 (s, 1H), 4.68 (m, 2H), 4.08 (s, 3H), 3.91 (m, 1H), 3.79 (d, J=12.0, 1H), 3.54 (t, J=6.4 Hz, 2H), 3.43 (m, 4H), 3.12 (s, 1H), 2.44 (m, 6H). ES-MS (m/z): 472.1 (MH⁺).

Example 71

Using a procedure identical to that described in synthetic scheme 1, the compound 4-(3'-ethynylphenylamino)-6-[3-(2-methyl-2,7-diazaspiro[4.4]-nonane-1-ketone-7-yl)-propoxy]-7-methoxyquinazoline (3-4-22) was obtained.

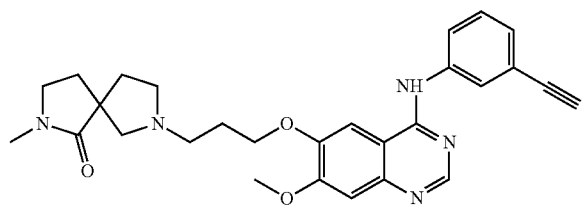 [SMILES: C#Cc1cccc(Nc2ncnc3cc(OC)c(OCCCN4CCC5(CCN(C)C5=O)C4)cc23)c1]

$^1$H NMR (CDCl$_3$) 8.96 (br, 1H), 8.67 (s, 1H), 8.22 (s, 1H), 8.18 (s, 1H), 7.97 (d, J=7.6 Hz, 1H), 7.34 (t, J=8.0 Hz, 1H), 7.25 (s, 1H), 4.59 (m, 2H), 4.02 (s, 3H), 3.66 (s, 1H), 3.50 (m, 1H), 3.34 (m, 6H), 3.08 (s, 1H), 2.88 (s, 3H), 2.30 (m, 6H). ES-MS (m/z): 486.1 (MH$^+$).

Example 72

Using a procedure identical to that described in synthetic scheme 1, the compound 4-(3'-ethynylphenylamino)-6-[3-(2,8-diazaspiro[4.5]decane-1-ketone-8-yl)-propoxy]-7-methoxyquinazoline (3-4-23) was obtained.

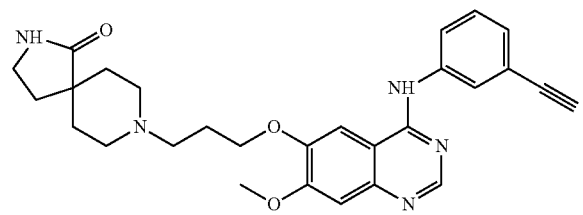 [SMILES: C#Cc1cccc(Nc2ncnc3cc(OC)c(OCCCN4CCC5(CCNC5=O)CC4)cc23)c1]

$^1$H NMR (CDCl$_3$) 8.95 (br, 1H), 8.67 (s, 1H), 8.26 (s, 1H), 8.16 (br, 1H), 7.98 (d, J=8.0 Hz, 1H), 7.35 (t, J=8.0 Hz, 1H), 7.24 (s, 1H), 7.22 (s, 1H), 4.55 (t, J=6.4 Hz, 2H), 4.02 (s, 3H), 3.61 (m, 2H), 3.38 (t, J=6.8 Hz, 2H), 3.35 (m, 2H), 3.22 (m, 2H), 3.08 (s, 1H), 2.42 (t, J=6.8 Hz, 4H), 2.07 (t, J=6.8 Hz, 2H), 1.99 (m, 2H). ES-MS (m/z): 485.9 (MH$^+$).

Example 73

Using a procedure identical to that described in synthetic scheme 1, the compound 4-(3'-ethynylphenylamino)-6-[3-(2-methyl-2,8-diazaspiro[4.5]decane-3-ketone-8-yl)-propoxy]-7-methoxyquinazoline (3-4-24) was obtained.

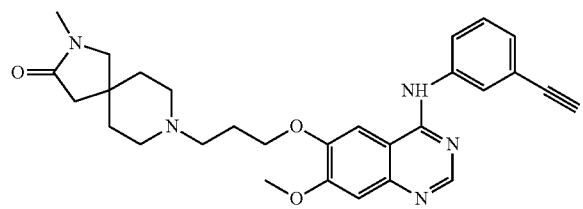 [SMILES: C#Cc1cccc(Nc2ncnc3cc(OC)c(OCCCN4CCC5(CC4)CC(=O)N(C)C5)cc23)c1]

$^1$H NMR (CDCl$_3$) 8.68 (s, 1H), 8.49 (br, 1H), 8.10 (s, 1H), 7.94 (d, J=7.2, 1H), 7.78 (s, 1H), 7.36 (t, J=8.0 Hz, 1H), 7.25 (s, 1H), 4.36 (t, J=6.4 Hz, 2H), 4.01 (s, 3H), 3.20 (s, 2H), 3.10 (s, 1H), 2.97 (m, 2H), 2.86 (s, 3H), 2.71 (m, 2H), 2.31 (m, 5H), 2.11 (m, 3H), 1.84 (m, 2H). ES-MS (m/z): 500.0 (MH$^+$).

Example 74

Using a procedure identical to that described in synthetic scheme 1, the compound 4-(3'-ethynylphenylamino)-6-[3-(1,8-diazaspiro[4.5]decane-2-ketone-8-yl)-propoxy]-7-methoxyquinazoline (3-4-25) was obtained.

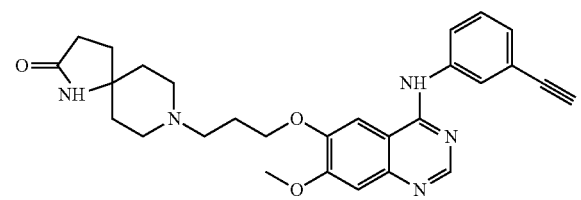 [SMILES: C#Cc1cccc(Nc2ncnc3cc(OC)c(OCCCN4CCC5(CCC(=O)N5)CC4)cc23)c1]

$^1$H NMR (CDCl$_3$) 8.68 (s, 1H), 8.14 (br, 1H), 7.95 (d, J=8.0 Hz, 1H), 7.35 (t, J=8.0 Hz, 1H), 7.25 (m, 2H), 4.40 (m, 2H), 4.00 (s, 3H), 3.13 (m, 4H), 3.10 (s, 1H), 2.43 (t, J=8.0 Hz, 2H), 2.33 (m, 4H), 2.01 (t, J=8.0 Hz, 2H), 1.83 (m, 4H). ES-MS (m/z): 485.9 (MH$^+$).

Example 75

Using a procedure identical to that described in synthetic scheme 1, the compound 4-(3'-ethynylphenylamino)-6-[3-(2-oxa-6-azaspiro[3.4]octane-6-yl)-propoxy]-7-methoxyquinazoline (3-4-C) was obtained.

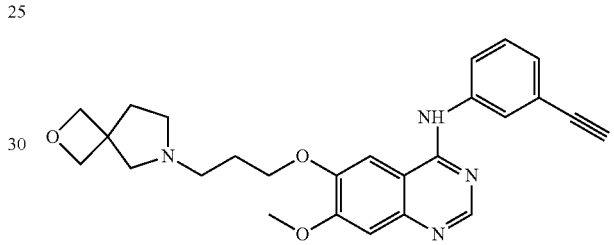

$^1$H NMR (CDCl$_3$) 8.69 (s, 1H), 8.07 (s, 1H), 7.89 (d, J=8.4 Hz, 1H), 7.64 (s, 1H), 7.37 (t, J=8.0 Hz, 1H), 7.27 (s, 1H), 4.70 (q, J=6.4 Hz, 4H), 4.40 (t, J=6.8 Hz, 2H), 4.03 (s, 3H), 3.25 (s, 2H), 3.11 (s, 1H), 2.98 (m, 4H), 2.37 (t, J=6.8 Hz, 2H), 2.29 (m, 2H). ES-MS (m/z): 445.3 (MH$^+$).

Example 76

Using a procedure identical to that described in synthetic scheme 1, the compound 4-(3'-chloro-4'-fluorophenylamino)-6-[3-(7-methyl-2,7-diazaspiro[4.4]nonane-2-yl)-propoxy]-7-methoxyquinazoline (3-C-1) was obtained.

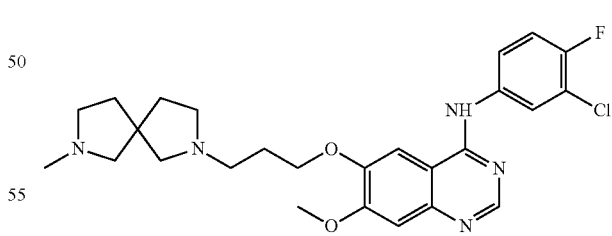

$^1$H NMR (CDCl$_3$) 8.67 (s, 1H), 7.96 (m, 2H), 7.66 (m, 1H), 7.38 (s, 1H), 7.18 (t, J=8.8 Hz, 1H), 4.25 (m, 2H), 4.03 (s, 3H), 2.80 (m, 4H), 2.61 (m 3H), 2.45 (m, 1H), 2.41 (s, 3H), 2.15 (m, 2H), 2.12 (m, 2H), 1.94 (m, 4H). ES-MS (m/z): 500.2 (MH$^+$).

Example 77

Using a procedure identical to that described in synthetic scheme 1, the compound 4-(3'-chloro-4'-4-fluorophenylamino)-6-[3-(7-tertbutyloxycarbonyl-2,7-diazaspiro[4.5]decane-2-yl)-propoxy]-7-methoxyquinazoline (3-C-10) was obtained.

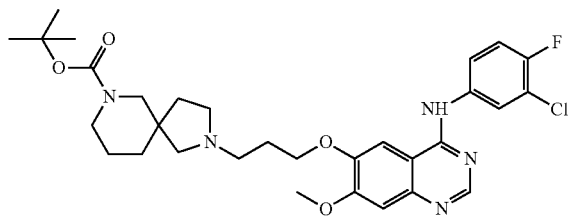 [SMILES: COc1cc2ncnc(Nc3ccc(F)c(Cl)c3)c2cc1OCCCN1CCC2(CCCN(C(=O)OC(C)(C)C)C2)C1]

$^1$H NMR (CDCl$_3$) 9.01 (s, 1H), 8.66 (s, 1H), 8.17 (br, 2H), 7.81 (m, 1H), 7.25 (s, 1H), 7.13 (t, J=8.8 Hz, 1H), 4.56 (m, 2H), 4.03 (s, 3H), 3.80 (m, 2H), 3.22 (m, 2H), 3.05 (m, 2H), 2.90 (m, 2H), 2.30 (m, 2H), 1.69 (m, 6H), 1.14 (s, 9H). ES-MS (m/z): 600.2 (MH$^+$).

Example 78

Using a procedure identical to that described in synthetic scheme 1, the compound 4-(3'-chloro-4'-fluorophenylamino)-6-[3-(cis-hexahydrofuro[3,2-b]pyrrole-4-yl)-propoxy]-7-methoxyquinazoline (3-C-11) was obtained.

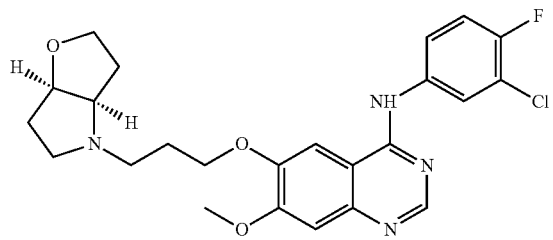 [SMILES: COc1cc2ncnc(Nc3ccc(F)c(Cl)c3)c2cc1OCCCN1CC[C@H]2OCC[C@H]21]

$^1$H NMR (CDCl$_3$) 8.68 (s, 1H), 7.95 (m, 1H), 7.60 (m, 2H), 7.26 (s, 1H), 7.19 (t, J=8.8 Hz, 1H), 4.55 (m, 1H), 4.26 (m, 2H), 4.03 (s, 3H), 3.89 (m, 1H), 3.22 (m, 1H), 3.14 (m, 2H), 2.95 (m, 1H), 2.60 (m, 1H), 2.37 (m, 1H), 2.16 (m, 2H), 2.03 (m, 2H), 1.87 (m, 2H). ES-MS (m/z): 473.2 (MH$^+$).

Example 79

Using a procedure identical to that described in synthetic scheme 1, the compound 4-(3'-chloro-4'-fluorophenylamino)-6-[3-(3,8-diazaspiro[4,5]-decyl-2-ketone)-propoxy-7-methoxyquinazoline (3-C-20) was obtained.

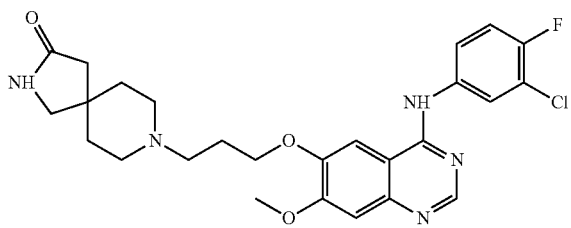 [SMILES: COc1cc2ncnc(Nc3ccc(F)c(Cl)c3)c2cc1OCCCN1CCC2(CC1)CNC(=O)C2]

$^1$H NMR (CDCl$_3$) 8.67 (s, 1H), 8.29 (br, 1H), 8.08 (m, 1H), 7.73 (m, 1H), 7.68 (s, 1H), 7.28 (s, 1H), 7.17 (t, J=8.8 Hz, 1H), 5.62 (s, 1H), 4.35 (t, J=6.4 Hz, 2H), 4.02 (s, 3H), 3.26 (s, 2H), 2.91 (m, 4H), 2.69 (m, 2H), 2.30 (m, 4H), 2.06 (m, 2H), 1.88 (m, 2H). ES-MS (m/z): 514.1 (MH$^+$).

Example 80

Using a procedure identical to that described in synthetic scheme 1, the compound 4-(3'-chloro-4'-fluorophenylamino)-6-[3-(2,7-diazaspiro[4.4]-nonane-1-ketone-7-yl)-propoxy]-7-methoxyquinazoline (3-C-21) was obtained.

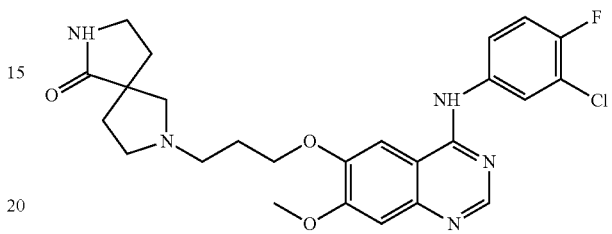

$^1$H NMR (CDCl$_3$) 8.88 (s, 1H), 8.65 (s, 1H), 8.13 (dd, J=2.4, 2.4 Hz, 1H), 8.24 (s, 1H), 7.80 (m, 1H), 7.25 (s, 1H), 7.15 (t, J=8.8 Hz, 1H), 5.57 (s, 1H), 4.52 (m, 2H), 4.03 (s, 3H), 3.40 (m, 2H), 3.28 (d, J=10.4 Hz, 1H), 3.15 (m, 3H), 3.04 (m, 2H), 2.31 (m, 4H), 2.08 (m, 2H). ES-MS (m/z): 500.1 (MH$^+$).

Example 81

Using a procedure identical to that described in synthetic scheme 1, the compound 4-(3'-chloro-4'-fluorophenylamino)-6-[3-(2-methyl-2,7-diazaspiro[4.4]-nonane-1-ketone-7-yl)-propoxy]-7-methoxyquinazoline (3-C-22) was obtained.

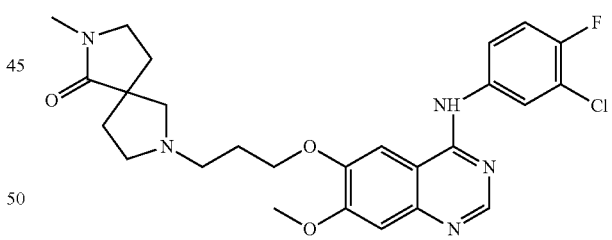

$^1$H NMR (CDCl$_3$) 8.97 (br, 1H), 8.63 (s, 1H), 8.07 dd, J=2.4, 2.4 Hz, 1H), 8.01 (s, 1H), 7.77 (m, 1H), 7.24 (s, 1H), 7.14 (t, J=8.8 Hz, 1H), 4.50 (m, 2H), 4.02 (s, 3H), 3.37 (m, 2H), 3.25 (d, J=10.4 Hz, 1H), 3.12 (m, 3H), 2.95 (m, 2H), 2.90 (s, 3H), 2.19 (m, 5H), 1.99 (m, 1H). ES-MS (m/z): 514.1 (MH$^+$).

Example 82

Using a procedure identical to that described in synthetic scheme 1, the compound 4-(3'-chloro-4'-fluorophenylamino)-6-[3-(2,8-diazaspiro[4.5]decane-1-ketone-8-yl)-propoxy]-7-methoxyquinazoline (3-C-23) was obtained.

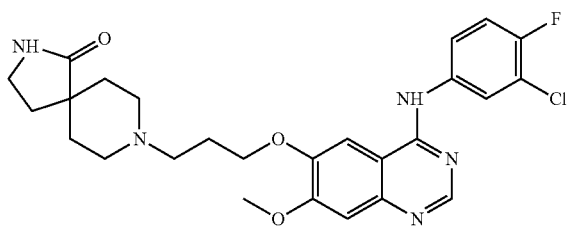 [SMILES: COc1cc2ncnc(Nc3ccc(F)c(Cl)c3)c2cc1OCCCN1CCC2(CCNC2=O)CC1]

¹H NMR (CDCl₃) 8.65 (s, 1H), 8.63 (br, 1H), 8.06 (m, 1H), 7.70 (m, 2H), 7.24 (s, 1H), 7.15 (t, J=8.0 Hz, 1H), 5.72 (s, 1H), 4.30 (t, J=6.4 Hz, 2H), 4.00 (s, 3H), 3.36 (t, J=6.8 Hz, 2H), 3.15 (s, 2H), 2.79 (s, 2H), 2.21 (m, 4H), 2.06 (t, J=6.8 Hz, 2H), 1.98 (m, 2H), 1.79 (m, 2H). ES-MS (m/z): 514.1 (MH⁺).

Example 83

Using a procedure identical to that described in synthetic scheme 1, the compound 4-(3'-chloro-4'-fluorophenylamino)-6-[3-(2-methyl-2,8-diazaspiro[4.5]decane-3-ketone-8-yl)-propoxy]-7-methoxyquinazoline (3-C-24) was obtained.

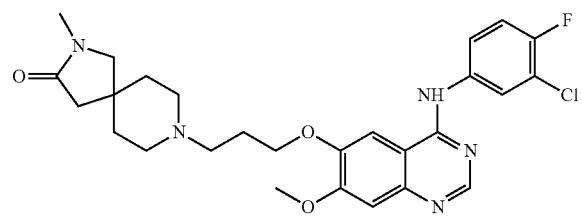 [SMILES: COc1cc2ncnc(Nc3ccc(F)c(Cl)c3)c2cc1OCCCN1CCC2(CC1)CC(=O)N(C)C2]

¹H NMR (CDCl₃) 8.67 (s, 1H), 8.54 (br, 1H), 8.14 (dd, J=2.4, 2.4 Hz, 1H), 7.86 (s, 1H), 7.78 (m, 1H), 7.27 (s, 1H), 7.17 (t, J=8.8 Hz, 1H), 4.41 (t, J=6.8 Hz, 2H), 4.02 (s, 3H), 3.25 (s, 2H), 3.04 (m, 2H), 2.88 (s, 3H), 2.77 (m, 2H), 2.36 (m, 4H), 2.18 (m, 2H), 1.87 (m, 4H). ES-MS (m/z): 528.1 (MH⁺).

Example 84

Using a procedure identical to that described in synthetic scheme 1, the compound 4-(3'-chloro-4'-fluorophenylamino)-6-[3-(1,8-diazaspiro[4.5]decane-2-ketone-8-yl)-propoxy]-7-methoxyquinazoline (3-C-25) was obtained.

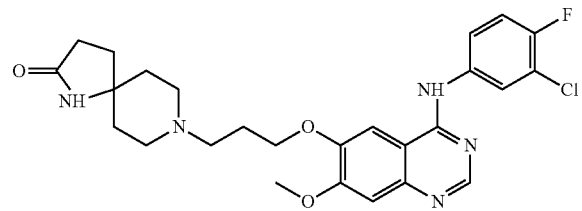 [SMILES: COc1cc2ncnc(Nc3ccc(F)c(Cl)c3)c2cc1OCCCN1CCC2(CCC(=O)N2)CC1]

¹H NMR (CDCl₃) 8.68 (s, 1H), 8.06 (br, 1H), 7.71 (m, 1H), 7.54 (m, 1H), 7.27 (s, 1H), 7.17 (t, J=8.8 Hz, 1H), 4.33 (m, 2H), 4.02 (s, 3H), 2.89 (m, 2H), 2.83 (m, 2H), 2.44 (t, J=8.0 Hz, 2H), 2.26 (m, 2H), 2.01 (m, 4H), 1.84 (m, 4H). ES-MS (m/z): 514.1 (MH⁺).

Example 85

Using a procedure identical to that described in synthetic scheme 1, the compound 4-(3'-chloro-4'-fluorophenylamino)-6-[3-(2-methyl-2,8-diazaspiro[4.5]decane-ketone-8-yl)]-propoxy]-7-methoxyquinazoline (3-C-26) was obtained.

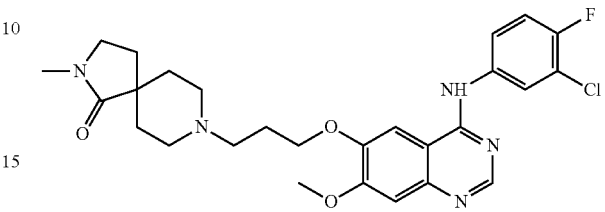

¹H NMR (CDCl₃) 8.76 (br, 1H), 8.66 (s, 1H), 8.16 (d, J=5.2 Hz, 1H), 7.92 (br, 1H), 7.80 (m, 1H), 7.25 (s, 1H), 7.16 (t, J=8.8 Hz, 1H), 4.42 (t, J=6.8 Hz, 2H), 4.02 (s, 3H), 3.42 (m, 2H), 3.36 (t, J=6.8 Hz, 2H), 2.99 (m, 3H), 2.86 (s, 3H), 2.32 (t, J=6.4 Hz, 2H), 2.06 (m, 2H), 1.98 (m, 5H). ES-MS (m/z): 528.1 (MH⁺).

Example 86

Using a procedure identical to that described in synthetic scheme 1, the compound 4-(3'-chloro-4'-fluorophenylamino)-6-[3-(2,6-diazaspiro[3.4]octane-7-ketone-2-yl)-propoxy]-7-methoxyquinazoline (3-C-27) was obtained.

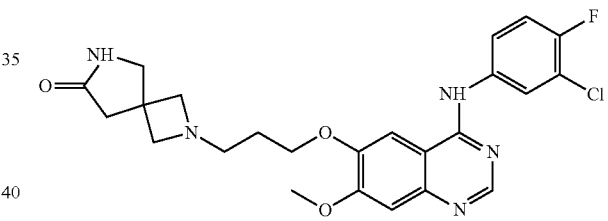

¹H NMR (CDCl₃) 8.67 (s, 1H), 7.97 (m, 1H), 7.68 (m, 2H), 7.28 (s, 1H), 7.19 (t, J=8.8 Hz, 2H), 5.56 (s, 1H), 4.25 (t, J=6.8 Hz, 2H), 4.03 (s, 3H), 3.62 (s, 2H), 3.44 (d, J=8.0 Hz, 2H), 3.33 (d, J=8.0 Hz, 2H), 2.78 (t, J=6.8 Hz, 2H), 2.55 (s, 2H), 2.02 (t, J=6.4 Hz, 2H). ES-MS (m/z): 485.9 (MH⁺).

Example 87

Using a procedure identical to that described in synthetic scheme 1, the compound 4-(3'-chloro-4'-fluorophenylamino)-6-[3-(1-oxa-3,8-diazaspiro[4.5]decane-2-ketone-8-yl)-propoxy]-7-methoxyquinazoline (3-C-28) was obtained.

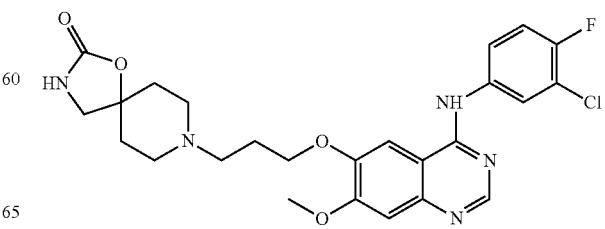

¹H NMR (CDCl₃) 8.67 (s, 1H), 8.06 (br, 1H), 8.01 (q, J=4.0 Hz, 1H), 7.69 (m, 1H), 7.51 (s, 1H), 7.17 (t, J=8.8 Hz, 2H), 5.13 (s, 1H), 4.31 (t, J=6.8 Hz, 2H), 4.02 (s, 3H), 3.40 (s, 2H), 2.83 (m, 2H), 2.76 (m, 2H), 2.23 (t, J=6.4 Hz, 2H), 2.08 (m, 2H), 1.98 (m, 4H). ES-MS (m/z): 515.9 (MH⁺).

Example 88

Using a procedure identical to that described in synthetic scheme 1, the compound 4-(3'-chloro-4'-fluorophenylamino)-6-[3-(5-tertbutyloxycarbonyl-hexahydropyrrolo[3,4-c]pyrrole-2-yl)-propoxy]-7-methoxyquinazoline (3-C-3) was obtained.

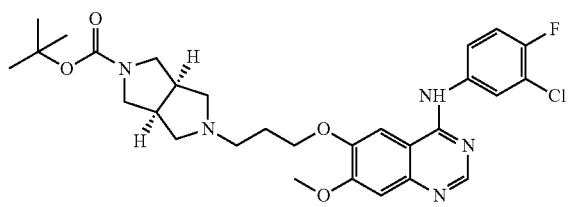 [SMILES: COc1cc2ncnc(Nc3ccc(F)c(Cl)c3)c2cc1OCCCN1C[C@@H]2CN(C(=O)OC(C)(C)C)C[C@@H]2C1]

¹H NMR (CDCl₃) 8.70 (s, 1H), 8.36 (m, 1H), 7.69 (br, 1H), 7.30 (s, 1H), 7.18 (m, 2H), 5.10 (s, 1H), 4.31 (t, J=6.4 Hz, 2H), 4.04 (s, 3H), 3.38 (s, 2H), 2.90 (m, 2H), 2.79 (m, 4H), 2.24 (m, 2H), 2.05 (m, 4H). ES-MS (m/z): 572.2 (MH⁺).

Example 89

Using a procedure identical to that described in synthetic scheme 1, the compound 4-(3'-chloro-4'-fluorophenylamino)-6-[3-[3-methyl-1-oxa-3,7-diazaspiro[4.4]nonane-2-ketone-7-yl)-propoxy]-7-methoxyquinazoline (3-C-30) was obtained.

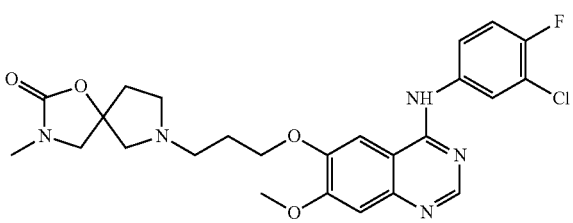 [SMILES: COc1cc2ncnc(Nc3ccc(F)c(Cl)c3)c2cc1OCCCN1CCC2(C1)CN(C)C(=O)O2]

¹H NMR (CDCl₃) 8.67 (s, 1H), 7.96 (m, 1H), 7.79 (br, 1H), 7.62 (m, 1H), 7.34 (s, 1H), 7.12 (t, J=8.8 Hz, 1H), 4.27 (q, J=6.8 Hz, 2H), 4.02 (s, 3H), 3.52 (q, J=6.0 Hz, 2H), 3.07 (d, J=10.8 Hz, 1H), 2.94 (m, 3H), 2.90 (s, 3H), 2.81 (m, 3H), 2.32 (m, 1H), 2.15 (m, 2H). ES-MS (m/z): 515.8 (MH⁺).

Example 90

Using a procedure identical to that described in synthetic scheme 1, the compound 4-(3'-chloro-4'-fluorophenylamino)-6-[3-(5-oxa-2,7-diazaspiro[3.4]octane-6-ketone-2-yl)-propoxy]-7-methoxyquinazoline (3-C-31) was obtained.

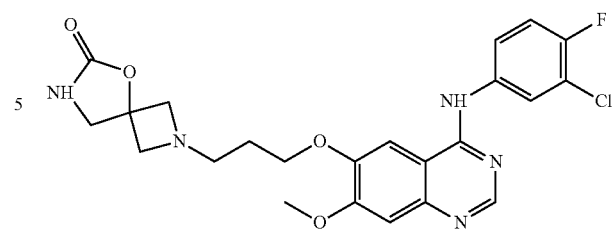

¹H NMR (CDCl₃) 8.68 (s, 1H), 7.95 (m, 1H), 7.58 (br, 1H), 7.30 (s, 1H), 7.20 (m, 2H), 7.08 (s, 1H), 4.95 (s, 1H), 4.25 (t, J=6.4 Hz, 2H), 4.04 (s, 3H), 3.84 (s, 2H), 3.60 (m, 4H), 2.82 (t, J=6.8 Hz, 2H), 2.04 (m, 2H). ES-MS (m/z): 487.8 (MH⁺).

Example 91

Using a procedure identical to that described in synthetic scheme 1, the compound 4-(3'-chloro-4'-fluorophenylamino)-6-[3-(7-methyl-5-oxa-2,7-diazaspiro[3.4]octane-6-ketone-2-yl)-propoxy]-7-methoxyquinazoline (3-C-32) was obtained.

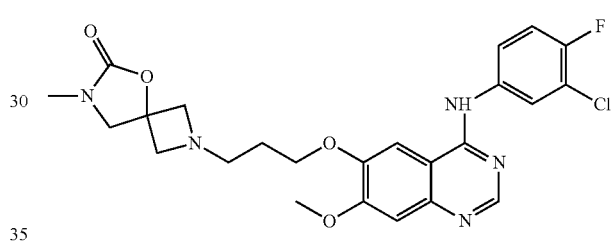

¹H NMR (CDCl₃) 8.68 (s, 1H), 7.93 (qJ=2.4 Hz, 1H), 7.60 (m, 1H), 7.45 (br, 1H), 7.20 (m, 2H), 4.22 (t, J=6.4 Hz, 2H), 4.03 (s, 3H), 3.74 (s, 2H), 3.55 (d, J=9.2 Hz, 2H), 3.46 (d, J=9.2 Hz, 2H), 2.89 (s, 3H), 2.78 (t, J=6.8 Hz, 2H), 2.03 (t, J=6.8 Hz, 2H). ES-MS (m/z): 501.8 (MH⁺).

Example 92

Using a procedure identical to that described in synthetic scheme 1, the compound 4-(3'-chloro-4'-fluorophenylamino)-6-[3-(7-acetyl-2,7-diazaspiro[4.4]-nonane-2-yl)-propoxy]-7-methoxyquinazoline (3-C-7) was obtained.

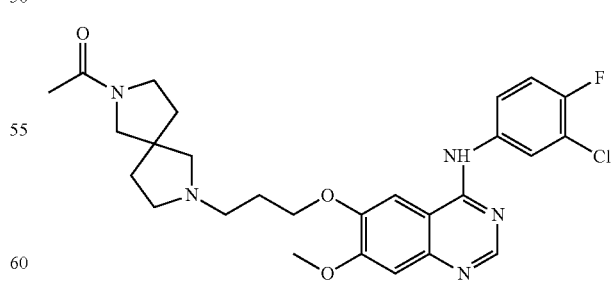

¹H NMR (CDCl₃) 8.78 (s, 1H), 8.66 (s, 1H), 8.01 (m, 1H), 7.70 (m, 1H), 7.53 (s, 1H), 7.27 (s, 1H), 7.15 (m, 1H), 4.28 (m, 2H), 4.02 (s, 3H), 3.82 (d, J=11.6, 1H), 3.52 (m, 3H), 3.21 (m, 1H), 2.67 (m, 4H), 2.20 (m, 4H), 2.04 (s, 3H), 1.92 (m, 3H). ES-MS (m/z): 528.2 (MH⁺).

Example 93

Using a procedure identical to that described in synthetic scheme 1, the compound 4-(3'-chloro-4'-fluorophenylamino)-6-[3-(8-oxa-3-aza-azabicyclo[3.2.1]octane-3-yl)-propoxy]-7-methoxyquinazoline (3-C-M) was obtained.

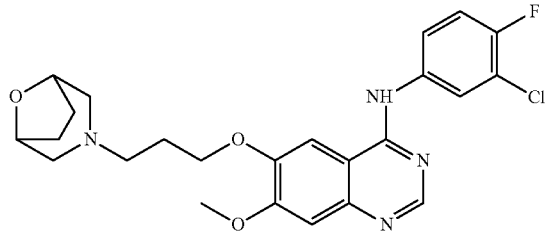 [SMILES: COc1cc2ncnc(Nc3ccc(F)c(Cl)c3)c2cc1OCCCN1CC2CCC(C1)O2]

¹H NMR (CDCl₃) 8.66 (s, 1H), 8.24 (m, 1H), 7.89 (m, 1H), 7.52 (s, 1H), 7.18 (t, J=8.8 Hz, 1H), 7.02 (s, 1H), 4.26 (t, J=6.8 Hz, 2H), 4.03 (s, 3H), 3.68 (m, 2H), 3.56 (m, 2H), 3.31 (m, 2H), 2.84 (m, 2H), 2.12 (m, 2H), 1.98 (m, 4H). ES-MS (m/z): 472.9 (MH⁺).

Example 94

Using a procedure identical to that described in synthetic scheme 1, the compound 4-(3'-chloro-4'-fluorophenylamino)-6-[3-(2,8-diazaspiro[4.5]decane-3-ketone-8-yl)-propoxy]-7-methoxyquinazoline (3-C—P) was obtained.

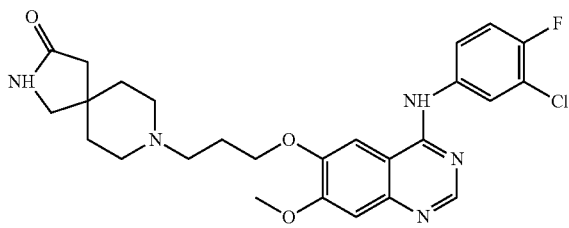 [SMILES: COc1cc2ncnc(Nc3ccc(F)c(Cl)c3)c2cc1OCCCN1CCC2(CC1)CNC(=O)C2]

¹H NMR (CDCl₃) 8.68 (s, 1H), 8.02 (m, 1H), 7.93 (br, 1H), 7.67 (m, 1H), 7.45 (s, 1H), 7.19 (t, J=8.8 Hz, 1H), 5.57 (s, 1H), 4.30 (m, 2H), 4.03 (s, 3H), 3.24 (s, 2H), 2.80 (m, 3H), 2.58 (m, 2H), 2.25 (s, 5H), 1.95 (m, 2H), 1.84 (m, 2H). ES-MS (m/z): 514.3 (MH⁺).

Example 95

Using a procedure identical to that described in synthetic scheme 1, the compound 4-(3'-chloro-4'-fluorophenylamino)-6-[3-(1-oxa-3,8-diazaspiro[4.5]decane-2-ketone-8-yl)-propoxy]-7-deuterated methoxyquinazoline (M5-28) was obtained.

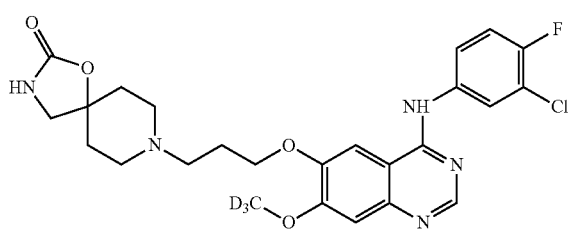 [SMILES: [2H]C([2H])([2H])Oc1cc2ncnc(Nc3ccc(F)c(Cl)c3)c2cc1OCCCN1CCC2(CC1)CNC(=O)O2]

¹H NMR (CDCl₃) 8.68 (s, 1H), 7.92 (q, J=2.4 Hz, 1H), 7.69 (s, 1H), 7.61 (t, J=4.8 Hz, 1H), 7.20 (m, 2H), 5.38 (br, 1H), 5.05 (s, 1H), 4.24 (t, J=6.8 Hz, 2H), 3.36 (s, 2H), 2.64 (m, 4H), 2.16 (m, 2H), 2.01 (m, 4H), 1.89 (m, 2H). ES-MS (m/z): 518.9 (MH⁺).

Example 96

Using a procedure identical to that described in synthetic scheme 1, the compound 4-(3'-chloro-4'-fluorophenylamino)-6-[3-(3-methyl-1-oxa-3,7-diazaspiro[4.4]nonane-2-ketone-7-yl)-propoxy]-7-deuterated methoxyquinazoline (M5-30) was obtained.

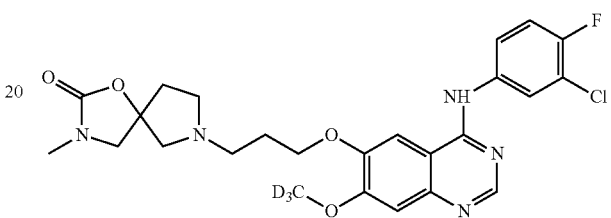

¹H NMR (CDCl₃) 8.66 (s, 1H), 7.96 (q, J=2.4 Hz, 1H), 7.62 (m, 1H), 7.39 (s, 1H), 7.26 (s, 1H), 7.17 (t, J=8.8 Hz, 1H), 4.24 (m, 2H), 3.53 (m, 2H), 3.05 (d, J=10.0 Hz, 1H), 2.90 (s, 3H), 2.76 (m, 4H), 2.30 (m, 1H), 2.11 (m, 4H). ES-MS (m/z): 518.9 (MH⁺).

Example 97

Using a procedure identical to that described in synthetic scheme 1, the compound 4-(3'-chloro-4'-fluorophenylamino)-6-[3-(5-oxa-2,7-diazaspiro[3.4]octane-6-ketone-2-yl)-propoxy]-7-deuterated methoxyquinazoline (M5-31) was obtained.

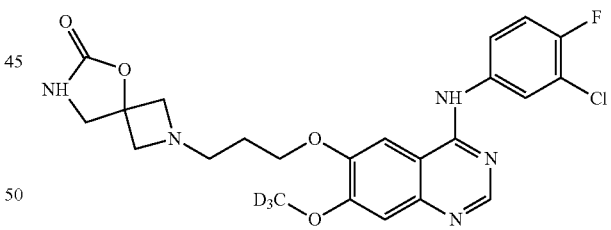

¹H NMR (CDCl₃) 8.66 (s, 1H), 7.93 (q, J=2.8 Hz, 1H), 7.65 (m, 1H), 7.34 (s, 1H), 7.25 (s, 1H), 7.17 (t, J=8.8 Hz, 1H), 5.62 (s, 1H), 4.20 (t, J=6.8 Hz, 2H), 3.81 (s, 2H), 3.50 (s, 4H), 2.76 (t, J=6.8 Hz, 2H), 2.03 (m, 2H). ES-MS (m/z): 490.9 (MH⁺).

Example 98

Using a procedure identical to that described in synthetic scheme 1, the compound 4-(3'-chloro-4'-fluorophenylamino)-6-[3-(7-methyl-5-oxa-2,7-diazaspiro[3.4]octane-6-ketone-2-yl)-propoxy]-7-deuterated methoxyquinazoline (M5-32) was obtained.

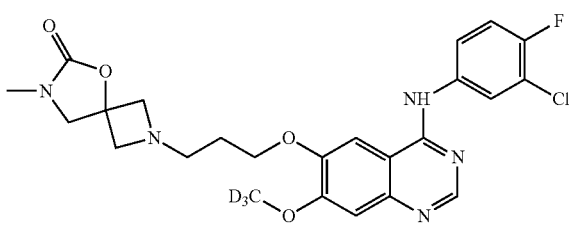 [SMILES: [2H]C([2H])([2H])Oc1cc2ncnc(Nc3ccc(F)c(Cl)c3)c2cc1OCCCN1CC2(C1)CN(C)C(=O)O2]

¹H NMR (CDCl₃) 8.67 (s, 1H), 7.91 (q, J=2.8 Hz, 1H), 7.86 (br, 1H), 7.62 (m, 1H), 7.25 (s, 1H), 7.18 (t, J=8.8 Hz, 1H), 4.18 (t, J=6.4 Hz, 2H), 3.73 (s, 2H), 3.50 (d, J=9.2 Hz, 2H), 3.42 (d, J=9.2 Hz, 2H), 2.87 (s, 3H), 2.873 (t, J=6.8 Hz, 2H), 2.02 (m, 2H). ES-MS (m/z): 504.9 (MH⁺).

Example 99

Using a procedure identical to that described in synthetic scheme 1, the compound 4-(3'-chloro-4'-fluorophenylamino)-6-[3-(2-oxa-6-azaspiro[3.4]octane-6-yl)-propoxy]-7-deuterated methoxyquinazoline (M5-C) was obtained.

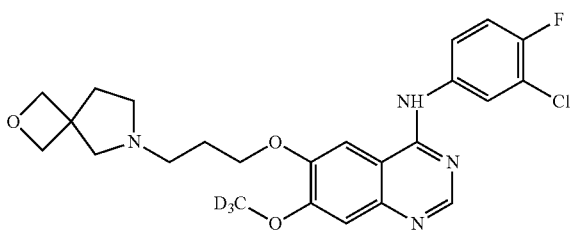 [SMILES: [2H]C([2H])([2H])Oc1cc2ncnc(Nc3ccc(F)c(Cl)c3)c2cc1OCCCN1CCC2(COC2)C1]

¹H NMR (CDCl₃) 8.67 (s, 1H), 7.97 (m, 1H), 7.82 (br, 1H), 7.64 (m, 1H), 7.33 (s, 1H), 7.25 (s, 1H), 7.18 (t, J=8.8 Hz, 1H), 4.66 (s, 4H), 4.26 (t, J=6.8 Hz, 2H), 3.01 (s, 2H), 2.72 (m, 4H), 2.23 (m, 2H), 2.06 (m, 2H). ES-MS (m/z): 475.9 (MH⁺).

Example 100

Using a procedure identical to that described in synthetic scheme 1, the compound 4-(3'-chloro-2'-fluorophenylamino)-6-[3-(1-oxa-3,8-diazaspiro[4.5]decane-2-ketone-8-yl)-propoxy]-7-methoxyquinazoline (3-2-28) was obtained.

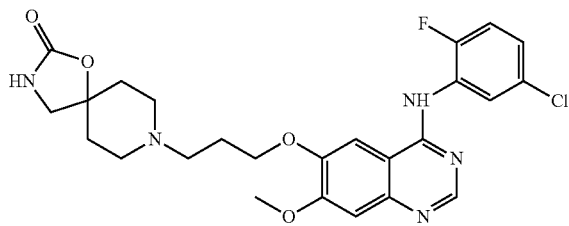 [SMILES: COc1cc2ncnc(Nc3cc(Cl)ccc3F)c2cc1OCCCN1CCC2(CC1)CNC(=O)O2]

¹H NMR (CDCl₃) 8.74 (s, 1H), 8.65 (d, J=5.2 Hz, 1H), 7.56 (br, 1H), 7.30 (s, 1H), 7.19 (s, 1H), 7.09 (m, 2H), 5.19 (s, 1H), 4.28 (t, J=6.4 Hz, 2H), 4.04 (s, 3H), 3.37 (s, 2H), 2.73 (m, 6H), 2.20 (t, J=6.8 Hz, 2H), 2.04 (m, 2H), 1.95 (m, 2H). ES-MS (m/z): 515.9 (MH⁺).

Example 101

Using a procedure identical to that described in synthetic scheme 1, the compound 4-(3'-chloro-2'-fluorophenylamino)-6-[3-(3-methyl-1-oxa-3,7-diazaspiro[4.4]nonane-2-ketone-7-yl)-propoxy]-7-methoxyquinazoline (3-2-30) was obtained.

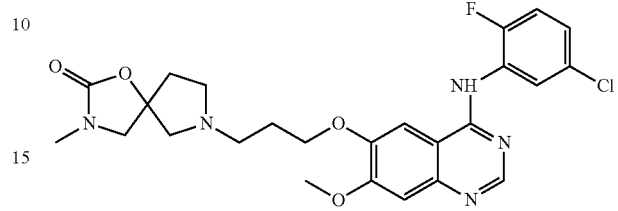

¹H NMR (CDCl₃) 8.75 (s, 1H), 8.69 (m, 1H), 7.50 (br, 1H), 7.30 (s, 1H), 7.11 (m, 3H), 4.26 (m, 2H), 4.04 (s, 3H), 3.56 (d, J=8.8 Hz, 1H), 3.49 (d, J=8.8 Hz, 1H), 2.92 (m, 1H), 2.86 (s, 3H), 2.80 (m, 4H), 2.35 (m, 1H), 2.14 (t, J=6.8 Hz, 2H), 2.04 (m, 2H). ES-MS (m/z): 515.9 (MH⁺).

Example 102

Using a procedure identical to that described in synthetic scheme 1, the compound 4-(3'-chloro-2'-fluorophenylamino)-6-[3-(5-oxa-2,7-diazaspiro[3.4]octane-6-ketone-2-yl)-propoxy]-7-methoxyquinazoline (3-2-31) was obtained.

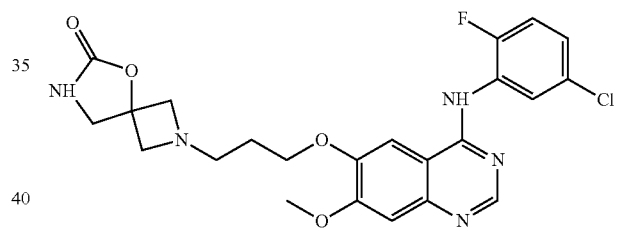

¹H NMR (CDCl₃) 8.75 (s, 1H), 8.71 (q, J=2.4 Hz, 1H), 7.45 (br, 1H), 7.30 (s, 1H), 7.10 (m, 3H), 5.22 (s, 1H), 4.22 (t, J=6.4 Hz, 2H), 4.04 (s, 3H), 3.83 (s, 2H), 3.57 (d, J=9.2 Hz, 2H), 3.45 (d, J=9.2 Hz, 2H), 2.78 (t, J=6.8 Hz, 2H), 2.03 (m, 2H). ES-MS (m/z): 487.9 (MH⁺).

Example 103

Using a procedure identical to that described in synthetic scheme 1, the compound 4-(5'-chloro-2'-fluorophenylamino)-6-[3-(7-methyl-5-oxa-2,7-diazaspiro[3.4]octane-6-ketone-2-yl)-propoxy]-7-methoxyquinazoline (3-2-32) was obtained.

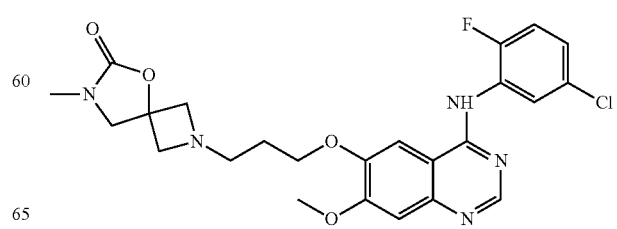

¹H NMR (CDCl₃) 8.76 (s, 1H), 8.74 (d, J=2.4 Hz, 1H), 7.40 (br, 1H), 7.31 (s, 1H), 7.08 (m, 3H), 4.23 (t, J=6.4 Hz, 2H), 4.05 (s, 3H), 3.76 (s, 2H), 3.56 (d, J=8.8 Hz, 2H), 3.43 (d, J=8.8 Hz, 2H), 2.89 (s, 3H), 2.78 (t, J=6.8 Hz, 2H), 2.02 (t, J=6.8 Hz, 2H). ES-MS (m/z): 501.9 (MH⁺).

Example 104

Using a procedure identical to that described in synthetic scheme 1, the compound 4-(3'-chloro-4'-fluorophenylamino)-6-[3-(5-oxa-2-azaspiro[3.4]octane-6-ketone-2-yl)-propoxy]-7-methoxyquinazoline (3-C-33) was obtained.

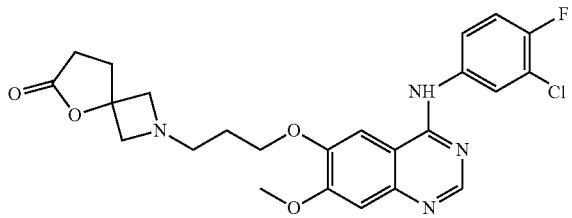 [SMILES: COc1cc2ncnc(Nc3ccc(F)c(Cl)c3)c2cc1OCCCN1CC2(CCC(=O)O2)C1]

¹H NMR (CDCl₃) 8.67 (s, 1H), 7.94 (q, J=2.4 Hz, 1H), 7.61 (m, 2H), 7.23 (s, 1H), 7.19 (t, J=8.8 Hz, 1H), 4.22 (t, J=6.8 Hz, 2H), 4.02 (s, 3H), 3.57 (d, J=9.2 Hz, 2H), 3.47 (d, J=9.2 Hz, 2H), 2.80 (t, J=6.8 Hz, 2H), 2.59 (m, 2H), 2.47 (m, 2H), 2.03 (m, 2H). ES-MS (m/z): 486.9 (MH⁺).

Example 105

Using a procedure identical to that described in synthetic scheme 1, the compound 4-(3'-chloro-4'-fluorophenylamino)-6-[3-(6-oxa-2-azaspiro[3.4]octane-7-ketone-2-yl)-propoxy]-7-methoxyquinazoline (3-C-34) was obtained.

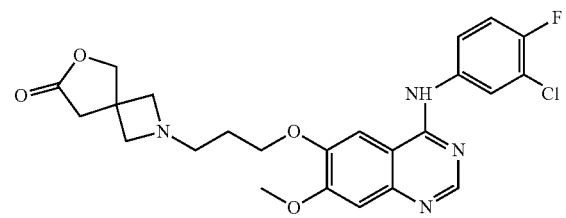 [SMILES: COc1cc2ncnc(Nc3ccc(F)c(Cl)c3)c2cc1OCCCN1CC2(COC(=O)C2)C1]

¹H NMR (CDCl₃) 8.68 (s, 1H), 7.94 (q, J=2.8 Hz, 1H), 7.62 (m, 1H), 7.50 (m, 1H), 7.19 (m, 2H), 4.45 (s, 2H), 4.21 (t, J=6.8 Hz, 2H), 4.03 (s, 3H), 3.38 (q, J=7.6 Hz, 4H), 2.75 (m, 4H), 2.03 (m, 2H). ES-MS (m/z): 486.9 (MH⁺).

Example 106

Using a procedure identical to that described in synthetic scheme 1, the compound 4-(3'-chloro-4'-fluorophenylamino)-6-[3-(6,6-dioxo-6-thia-2-azaspiro[3.4]octane-2-yl)propoxy]-7-methoxyquinazoline (3-C-35) was obtained.

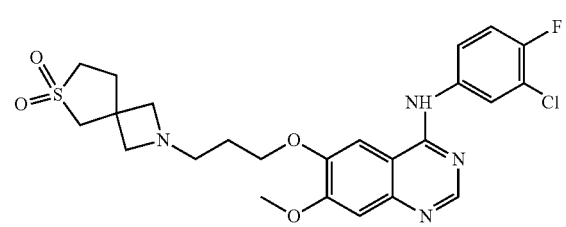 [SMILES: COc1cc2ncnc(Nc3ccc(F)c(Cl)c3)c2cc1OCCCN1CC2(CCS(=O)(=O)C2)C1]

¹H NMR (CDCl₃) 8.68 (s, 1H), 7.91 (m, 1H), 7.56 (m, 1H), 7.47 (br, 1H), 7.19 (t, J=8.8 Hz, 1H), 7.14 (s, 1H), 4.21 (t, J=6.4 Hz, 2H), 4.08 (s, 4H), 4.02 (s, 3H), 2.89 (s, 2H), 2.76 (m, 4H), 2.19 (t, J=7.2 Hz, 2H), 2.11 (t, J=6.8 Hz, 2H). ES-MS (m/z): 521.00 (MH⁺).

Example 107

Using a procedure identical to that described in synthetic scheme 1, the compound 4-(5'-chloro-2'-fluorophenylamino)-6-[3-(6,6-dioxo-thia-2-azaspiro[3.4]octane-2-yl)propoxy]-7-methoxyquinazoline (3-2-35) was obtained.

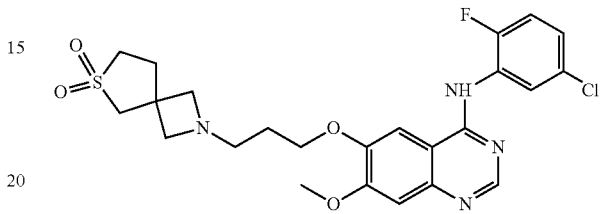

¹H NMR (CDCl₃) 8.76 (s, 1H), 8.73 (m, 1H), 7.42 (br, 1H), 7.31 (s, 1H), 7.08 (m, 3H), 4.25 (t, J=6.4 Hz, 2H), 4.10 (s, 4H), 4.04 (s, 3H), 2.93 (s, 2H), 2.80 (m, 4H), 2.22 (t, J=7.2 Hz, 2H), 2.16 (t, J=6.8 Hz, 2H). ES-MS (m/z): 521.00 (MH⁺).

Example 108

Using a procedure identical to that described in synthetic scheme 1, the compound 4-(3'-chloro-2'-fluorophenylamino)-6-[3-(6,6-dioxo-thia-2-azaspiro[3.4]octane-2-yl)propoxy]-7-methoxyquinazoline (3-3-35) was obtained.

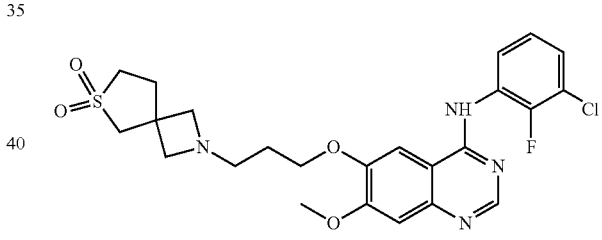

¹H NMR (CDCl₃) 8.72 (s, 1H), 8.45 (m, 1H), 7.47 (br, 1H), 7.31 (s, 1H), 7.18 (m, 1H), 7.12 (s, 1H), 4.24 (t, J=6.4 Hz, 2H), 4.10 (s, 4H), 4.04 (s, 3H), 2.93 (s, 2H), 2.80 (m, 4H), 2.22 (t, J=7.2 Hz, 2H), 2.16 (t, J=6.8 Hz, 2H). ES-MS (m/z): 521.00 (MH⁺).

Example 109

Using a procedure identical to that described in synthetic scheme 1, the compound 4-(3'-ethynylphenylamino)-6-[3-(6,6-dioxo-6-thia-2-azaspiro[3.4]octane-2-yl)propoxy]-7-methoxyquinazoline (3-4-35) was obtained.

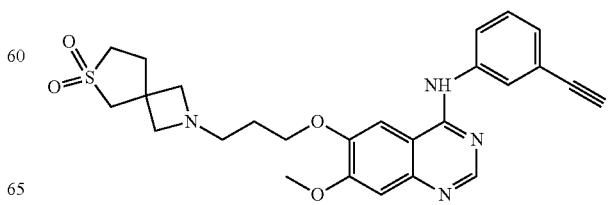

¹H NMR (CDCl₃) 8.70 (s, 1H), 7.87 (s, 1H), 7.80 (d, J=8.0 Hz, 1H), 7.50 (br, 1H), 7.38 (t, J=8.0 Hz, 1H), 7.31 (s, 1H), 7.16 (s, 1H), 4.20 (t, J=6.4 Hz, 2H), 4.09 (s, 4H), 4.02 (s, 3H), 3.13 (s, 1H), 2.90 (s, 2H), 2.78 (m, 4H), 2.18 (t, J=7.2 Hz, 2H), 2.12 (t, J=6.8 Hz, 2H). ES-MS (m/z): 493.1 (MH⁺).

Example 110

Using a procedure identical to that described in synthetic scheme 1 to prepare 4-(3'-ethynylphenylamino)-6-[3-(5-tert-butyloxycarbonyl-cis-hexahydropyrrolo[3,4-b]pyrrole-1-yl)-propoxyl]-7-methoxyquinazoline, and after ethyl acetate-dimethyl sulfide solution was dissolved into, the concentrated hydrochloric acid was added to remove Boc protection. Stirring at the room temperature till the reaction ended. After the dried crude product was washed by ether, 4-(3'-ethynylphenylamino)-6-[3-cis-hexahydropyrrolo[3,4-b]pyrrole-1-yl)-propoxyl]-7-methoxyquinazoline hydrochloride (3-4-2) was obtained by filtration and decompression.

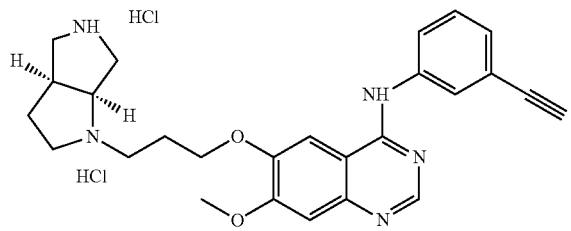 [SMILES: C#Cc1cccc(Nc2ncnc3cc(OC)c(OCCCN4CC[C@H]5CNC[C@H]54)cc23)c1 ; Cl ; Cl]

¹H NMR (CD₃OD) 8.67 (s, 1H), 8.15 (s, 1H), 7.86 (s, 1H), 7.74 (d, J=8.0 Hz, 1H), 7.45 (m, 2H), 7.32 (s, 1H), 4.55 (br, 1H), 4.44 (m, 2H), 4.10 (s, 3H), 3.95 (m, 2H), 3.79 (m, 1H), 3.62 (m, 1H), 3.50 (m, 4H), 2.55 (m, 1H), 2.44 (m, 2H), 2.02 (m, 3H). ES-MS (m/z): 444.2 (MH⁺).

Example 111

Using a procedure identical to that described in synthetic scheme 1 to prepare 4-(3'-ethynylphenylamino)-6-[3-(5-tert-butyloxycarbonyl-cis-hexahydropyrrolo[3,4-b]pyrrole-1-yl)-propoxyl]-7-methoxyquinazoline, and after ethyl acetate-dimethyl sulfide solution was dissolved into, the concentrated hydrochloric acid was added to remove Boc protection. Stirring at the room temperature till the reaction ended. After the dried crude product was washed by ether, 4-(3'-chloro-2'-fluorophenylamino)-6-[3-(cis-hexahydropyrrolo[3,4-b]pyrrole-1-yl)-propoxy]-7-methoxyquinazoline hydrochloride (3-3-2) was obtained by filtration and decompression.

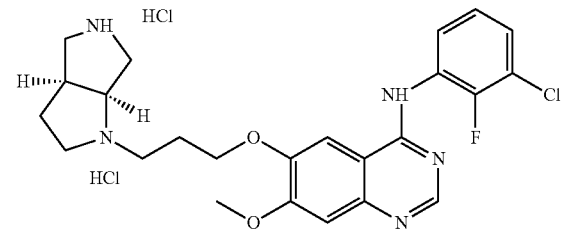 [SMILES: COc1cc2ncnc(Nc3cccc(Cl)c3F)c2cc1OCCCN1CC[C@H]2CNC[C@H]21 ; Cl ; Cl]

¹H NMR (CD₃OD) 8.67 (s, 1H), 8.13 (s, 1H), 7.55 (m, 2H), 7.40 (s, 1H), 7.34 (m, 2H), 4.45 (m, 2H), 4.14 (s, 3H), 3.95 (m, 2H), 3.89 (m, 1H), 3.71 (m, 1H), 3.60 (m, 4H), 2.55 (m, 1H), 2.48 (m, 2H), 2.05 (m, 3H). ES-MS (m/z): 472.1 (MH⁺).

Example 112

Using a procedure identical to that described in synthetic scheme 1 to prepare 4-(3'-ethynylphenylamino)-6-[3-(5-tert-butyloxycarbonyl-cis-hexahydropyrrolo[3,4-b]pyrrole-1-yl)-propoxyl]-7-methoxyquinazoline, and after ethyl acetate-dimethyl sulfide solution was dissolved into, the concentrated hydrochloric acid was added to remove Boc protection. Stirring at the room temperature till the reaction ended. After the dried crude product was washed by ether, 4-(3'-chloro-2'-fluorophenylamino)-6-[3-(cis-octahydropyrrol[3,2-c]pyrrole-1-yl)-propoxy]-7-methoxyquinazoline hydrochloride (3-3-4) was obtained by filtration and decompression.

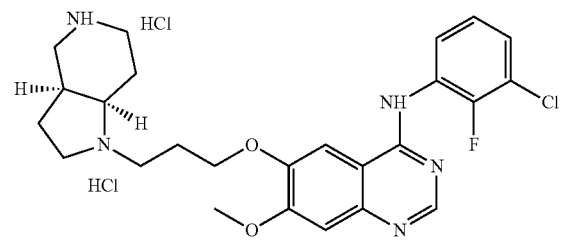 [SMILES: COc1cc2ncnc(Nc3cccc(Cl)c3F)c2cc1OCCCN1CC[C@H]2CNCC[C@H]21 ; Cl ; Cl]

¹H NMR (CD₃OD) 8.68 (s, 1H), 8.17 (s, 1H), 7.54 (m, 2H), 7.39 (s, 1H), 7.32 (m, 1H), 4.46 (m, 2H), 4.12 (s, 3H), 3.47 (m, 5H), 3.05 (m, 3H), 2.46 (m, 5H), 2.02 (m, 3H). ES-MS (m/z): 486.1 (MH⁺).

Example 113

Using a procedure identical to that described in synthetic scheme 1 to prepare 4-(3'-ethynylphenylamino)-6-[3-(5-tert-butyloxycarbonyl-cis-hexahydropyrrolo[3,4-b]pyrrole-1-yl)-propoxyl]-7-methoxyquinazoline, and after ethyl acetate-dimethyl sulfide solution was dissolved into, the concentrated hydrochloric acid was added to remove Boc protection. Stirring at the room temperature till the reaction ended. After the dried crude product was washed by ether, 4-(3'-chloro-2'-fluorophenylamino)-6-[3-(cis-octahydropyrrolo[3,4-c]azepine-2-yl)-propoxy]-7-methoxyquinazoline hydrochloride (3-3-5) was obtained by filtration and decompression.

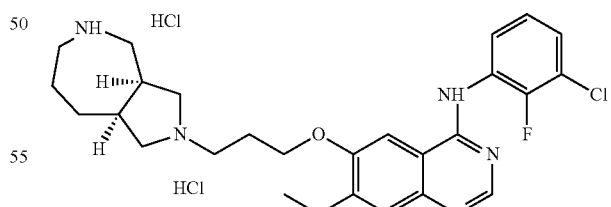

¹H NMR (CD₃OD) 8.71 (s, 1H), 8.12 (m, 1H), 7.56 (m, 2H), 7.32 (m, 1H), 4.50 (m, 2H), 4.16 (s, 3H), 3.56 (m, 4H), 3.15 (m, 4H), 2.52 (m, 2H), 2.11 (m, 5H), 1.34 (m, 3H). ES-MS (m/z): 500.1 (MH⁺).

Example 114

Using a procedure identical to that described in synthetic scheme 1, the compound 4-(3'-chloro-2'-fluorophenylamino)-6-[3-(5-tertbutyloxycarbonyl-cis-octahydropyr-rolo[3,4-c]pyrrole-2-yl)-propoxy]-7-methoxyquinazoline (3-3-6) was obtained.

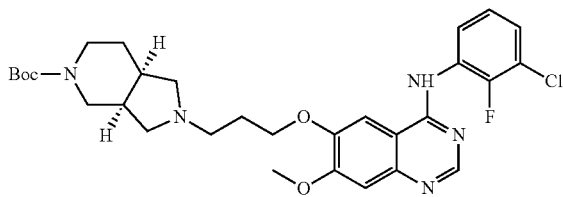 [SMILES: COc1cc2ncnc(Nc3cccc(Cl)c3F)c2cc1OCCCN1C[C@@H]2CCN(C(=O)OC(C)(C)C)C[C@@H]2C1]

$^1$H NMR (CDCl$_3$) 8.62 (s, 1H), 7.84 (m, 2H), 7.26 (s, 1H), 7.20 (m, 1H), 7.11 (m, 1H), 4.45 (m, 2H), 4.02 (s, 3H), 3.65 (m, 2H), 3.38 (m, 2H), 3.14 (m, 2H), 2.87 (m, 2H), 2.56 (m, 4H), 2.31 (m, 1H), 1.92 (m, 1H), 1.65 (m, 1H), 1.43 (s, 9H), 1.28 (m, 1H). ES-MS (m/z): 586.0 (MH$^+$).

Example 115

Using a procedure identical to that described in synthetic scheme 1, the compound 4-(3'-chloro-2'-fluorophenylamino)-6-[3-(5-oxa-2-azaspiro[3.4]octane-6-ketone-2-yl)-propoxy]-7-methoxyquinazoline (3-3-33) was obtained.

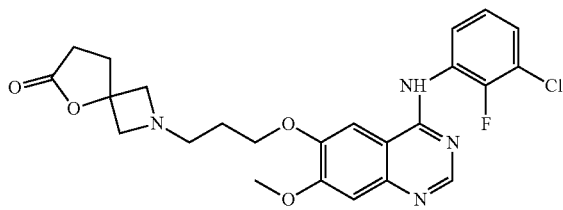 [SMILES: COc1cc2ncnc(Nc3cccc(Cl)c3F)c2cc1OCCCN1CC2(CCC(=O)O2)C1]

$^1$H NMR (CDCl$_3$) 8.72 (s, 1H), 8.48 (m, 1H), 7.41 (m, 1H), 7.30 (s, 1H), 7.19 (m, 1H), 7.11 (s, 1H), 4.24 (t, J=6.4 Hz, 2H), 4.05 (s, 3H), 3.56 (d, J=8.8 Hz, 2H), 3.41 (d, J=8.8 Hz, 2H), 2.79 (t, J=6.8 Hz, 2H), 2.58 (t, J=7.2 Hz, 2H), 2.51 (t, J=7.2 Hz, 2H), 2.03 (t, J=6.4 Hz, 2H). ES-MS (m/z): 487.1 (MH$^+$).

Example 116

Using a procedure identical to that described in synthetic scheme 1, the compound 4-(3'-chloro-2'-fluorophenylamino)-6-[3-(6-oxa-2-azaspiro[3.4]octane-7-ketone-2-yl)-propoxy]-7-methoxyquinazoline (3-3-34) was obtained.

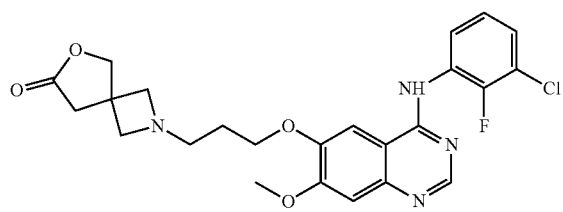 [SMILES: COc1cc2ncnc(Nc3cccc(Cl)c3F)c2cc1OCCCN1CC2(COC(=O)C2)C1]

$^1$H NMR (CDCl$_3$) 8.73 (s, 1H), 8.48 (m, 1H), 7.42 (br, 1H), 7.31 (s, 1H), 7.18 (m, 2H), 7.10 (s, 1H), 4.45 (s, 2H), 4.22 (t, J=6.4 Hz, 2H), 4.04 (s, 3H), 3.35 (dd, J=7.2 Hz, 7.2 Hz, 4H), 2.733 (m, 4H), 2.02 (m, 2H). ES-MS (m/z): 487.0 (MH$^+$).

Example 117

Using a procedure identical to that described in synthetic scheme 1, the compound 4-(3'-ethynylphenylamino)-6-[3-(5-oxa-2-azaspiro[3.4]octane-6-ketone-2-yl)-propoxy]-7-methoxyquinazoline (3-4-33) was obtained.

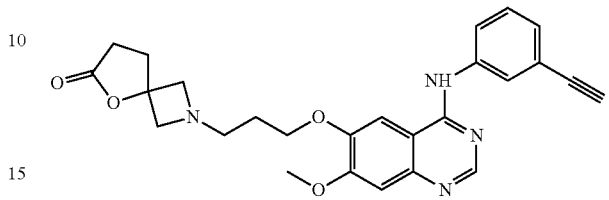

$^1$H NMR (CDCl$_3$) 8.70 (s, 1H), 7.92 (s, 1H), 7.82 (m, 1H), 7.45 (br, 1H), 7.39 (m, 1H), 7.31 (s, 1H), 7.21 (s, 1H), 4.26 (t, J=6.8 Hz, 2H), 4.04 (s, 3H), 3.66 (m, 2H), 3.51 (m, 2H), 3.12 (s, 1H), 2.86 (m, 2H), 2.56 (m, 4H), 2.06 (m, 2H). ES-MS (m/z): 459.1 (MH$^+$).

Example 118

Using a procedure identical to that described in synthetic scheme 1, the compound 4-(3'-ethynylphenylamino)-6-[3-(6-oxa-2-azaspiro[3.4]octane-7-ketone-2-yl)-propoxy]-7-methoxyquinazoline (3-4-34) was obtained.

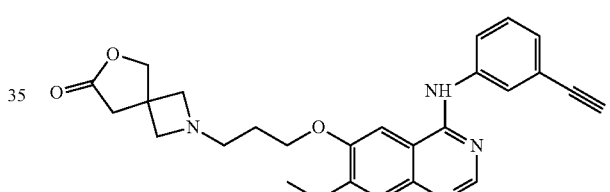

$^1$H NMR (CDCl$_3$) 8.70 (s, 1H), 7.89 (s, 1H), 7.81 (d, J=8.0 Hz, 1H), 7.39 (t, J=8.0 Hz, 2H), 7.31 (s, 2H), 7.14 (s, 1H), 4.45 (s, 2H), 4.21 (t, J=6.4 Hz, 2H), 4.03 (s, 3H), 3.37 (m, 4H), 3.13 (s, 1H), 2.74 (t, J=6.4 Hz, 4H), 2.02 (m, 2H). ES-MS (m/z): 459.2 (MH$^+$).

Example 119

Inhibitory Effect on Receptor Tyrosine Kinase EGFR of the Compounds

The inhibitory effect on the receptor tyrosine kinase EGFR (purchased from Shanghai 3bio Technology Co., Ltd., Lot No. 4018780925) of the compounds prepared in example 1-example 51 and example 53-example 99 was determined by in vitro testing, the specific testing methods were as follows:

Poly(Glu, Tyr)$_{4:1}$ was diluted into 100 μg/ml by PBS without potassium. Enzyme label plate was coated with 37 μl/well at 37° C. overnight, The liquid in the wells was removed. The plate was rinsed by T-PBS for 5 minutes, and dried at 37° C. after repeated 3 times.

The testing sample was diluted to the concentration concerned by reaction buffer solution, and added into the wells of the coated enzyme label plate. The concentration diluted should realize 1.0000 μg/ml, 0.1250 μg/ml, 0.0156 μg/ml, 0.00195 μg/ml and 0.00024 μg/ml in the 100 μl reaction.

Adding in ATP solution (4 μM of final concentration) diluted by reaction buffer solution, Finally, the tyrosine kinase diluted by reaction buffer solution was added, and forming the reaction with 100 μl total volume.

Meanwhile, negative control wells and enzyme-free control wells were prepared. The reaction was kept in the dark wet box for 1 hour at 37° C. The plate was rinsed by T-PBS for three times after the reaction ended, and blocked by 1% BSA 37% for 30 min, and then, PY99 antibody (1:1000 diluted by 0.05% PBST with 1% BSA) was added in 100 μl/well. After incubated at 37° C. for 30 minutes, the plate was rinsed by T-PBS for three times, and the goat anti-mouse IgG marked with HRP (1 mg/ml 1:1000 diluted by 0.05% PBST with 1% BSA) was then added in 100 μl/well. After incubated at 37° C. for 30 minutes, the plate was rinsed by T-PBS for three times.

Colorimetric solution OPD was added in 100 μl/well for 20 minutes' reaction in the dark side at the room temperature. Colorimetric substrate solution OPD was the solution of 0.1 mol/L citric acid-disodium hydrogen phosphate buffer (pH 5.0) with 20 mmol/L OPD and 12 mmol/L $H_2O_2$ (freshly prepared when using).

50 μl of 2M $H_2SO_4$ (2 mol/L sulfuric acid containing 0.1 mol/L sodium sulfate) was added in to terminate the reaction, and the $A_{492}$ value was read with adjustable wavelength micro late enzyme-labeling instrument VERSAmax.

The inhibition rate of samples is calculated by the following formula:

$$\text{Inhibition rate of samples \%} = \left(1 - \frac{OD \text{ value of compound} - OD \text{ value of enzyme} - \text{free control hole}}{OD \text{ value of negative control} - OD \text{ value of enzyme} - \text{free control hole}}\right) \times 100\%$$

TABLE 1

The results show that the compounds of the invention possesses strong inhibitory effect on activity of tyrosine kinase EGFR and the range of $IC_{50}$ value is shown in Table 1. In Table 1, the value of $IC_{50}$ larger than 1000 nM is referred to "*", the value of $IC_{50}$ between 100 nM-1000 nM is referred to "", the value of $IC_{50}$ between 10 nM-100 nM is referred to "*", and the value of $IC_{50}$ between 0.1 nM-10 nM is referred to "****".

| Compound | $IC_{50}$ (nM) |
| --- | --- |
| Example 1 | *** |
| Example 2 | **** |
| Example 3 | ** |
| Example 4 | *** |
| Example 5 | *** |
| Example 6 | *** |
| Example 7 | *** |
| Example 8 | *** |
| Example 9 | *** |
| Example 10 | *** |
| Example 11 | ** |
| Example 12 | *** |
| Example 13 | *** |
| Example 14 | **** |
| Example 15 | *** |
| Example 16 | *** |
| Example 17 | *** |

TABLE 1-continued

The results show that the compounds of the invention possesses strong inhibitory effect on activity of tyrosine kinase EGFR and the range of $IC_{50}$ value is shown in Table 1. In Table 1, the value of $IC_{50}$ larger than 1000 nM is referred to "*", the value of $IC_{50}$ between 100 nM-1000 nM is referred to "", the value of $IC_{50}$ between 10 nM-100 nM is referred to "*", and the value of $IC_{50}$ between 0.1 nM-10 nM is referred to "****".

| Compound | $IC_{50}$ (nM) |
| --- | --- |
| Example 18 | *** |
| Example 19 | *** |
| Example 20 | *** |
| Example 21 | *** |
| Example 22 | *** |
| Example 23 | *** |
| Example 24 | *** |
| Example 25 | *** |
| Example 26 | *** |
| Example 27 | *** |
| Example 28 | *** |
| Example 29 | *** |
| Example 30 | *** |
| Example 31 | *** |
| Example 32 | *** |
| Example 33 | *** |
| Example 34 | **** |
| Example 35 | **** |
| Example 36 | **** |
| Example 37 | **** |
| Example 38 | *** |
| Example 39 | *** |
| Example 40 | *** |
| Example 41 | ** |
| Example 42 | ** |
| Example 43 | *** |
| Example 44 | *** |
| Example 45 | *** |
| Example 46 | *** |
| Example 47 | *** |
| Example 48 | **** |
| Example 49 | **** |
| Example 50 | **** |
| Example 51 | **** |
| Example 53 | *** |
| Example 54 | * |
| Example 55 | ** |
| Example 56 | * |
| Example 57 | * |
| Example 58 | ** |
| Example 59 | *** |
| Example 60 | ** |
| Example 61 | *** |
| Example 62 | ** |
| Example 63 | ** |
| Example 64 | *** |
| Example 65 | *** |
| Example 66 | *** |
| Example 67 | **** |
| Example 68 | *** |
| Example 69 | *** |
| Example 70 | *** |
| Example 71 | *** |
| Example 72 | *** |
| Example 73 | *** |
| Example 74 | *** |
| Example 75 | *** |
| Example 76 | *** |
| Example 77 | * |
| Example 78 | *** |
| Example 79 | **** |
| Example 80 | **** |
| Example 81 | *** |
| Example 82 | *** |
| Example 83 | **** |
| Example 84 | *** |
| Example 85 | *** |
| Example 86 | *** |
| Example 87 | *** |
| Example 88 | * |

TABLE 1-continued

The results show that the compounds of the invention possesses strong inhibitory effect on activity of tyrosine kinase EGFR and the range of $IC_{50}$ value is shown in Table 1. In Table 1, the value of $IC_{50}$ larger than 1000 nM is referred to "*", the value of $IC_{50}$ between 100 nM-1000 nM is referred to "", the value of $IC_{50}$ between 10 nM-100 nM is referred to "*", and the value of $IC_{50}$ between 0.1 nM-10 nM is referred to "****".

| Compound | $IC_{50}$ (nM) |
| --- | --- |
| Example 89 | *** |
| Example 90 | **** |
| Example 91 | *** |
| Example 92 | *** |
| Example 93 | ** |
| Example 94 | *** |
| Example 95 | *** |
| Example 96 | *** |
| Example 97 | ** |
| Example 98 | **** |
| Example 99 | ** |

Example 120

Anticancer Effect of the Compounds

The inhibitory effect on the cancer cells of the compounds prepared in Example 1-Example 13, Example 20, Example 48, Example 49 and Example 57 was determined in vitro using cancer cells. The results are shown in table 2, and the specific detection methods are as follows:

1. Cell Culture

Human lung cancer cells were (A549, purchased from Shanghai FuMeng Gene Bio-technology Co., Ltd.) cultured in DMEM containing 2 m M/L-glutamine and 10% FBS, and inoculated in 96-well plate, 200 μL/well and 2000 cells per well; the plate was preincubated for 24 hours under the condition of 5% $CO_2$ and 100% relative humidity at 37° C., allowing for cell adherence.

2. Compounds Screening

When the cells adhered, the supernatant was removed, and 200 μL drug-containing culture medium was added with different concentration of compounds into each well (in concentration of 20 μg/ml, 12.5 g/ml, 6.25 μg/ml, 3.125 g/ml, 1.5625 μg/ml and 0.78125 μg/ml), 3 multiple wells were set up for each drug concentration as well as blank control (cell culture medium without cells), and drug-free control (with no drugs, filled with complete medium in equal amount only), cultured for 72 hours under the condition of 5% $CO_2$ incubator at 37° C. (100% relative humidity).

3. Cell Detection

After the culture ended, the supernatant was carefully removed, and adding 200 μl DMEM culture medium containing 3% FBS with 500 μg/ml MTT into each well, and culturing for 4 hours under the condition of 5% $CO_2$ incubator at 37° C. (100% relative humidity). After the supernatant was discarded, 150 μL DMSO was added in each well for solving. the $GI_{50}$ value was measured by detecting the absorbance in the 570 nm wavelength.

4. Screening Result

The compounds of the invention possess strong killing activity to human lungs cancer cell strain (A549), of which the $GI_{50}$ is between 1 μM and 60 μM, and have lower killing effect on normal endothelium.

TABLE 2

| Compound | $GI_{50}$ (μM) |
| --- | --- |
| Example 1 | 39.7 |
| Example 2 | 20.4 |
| Example 3 | 10.2 |
| Example 4 | 8.5 |
| Example 5 | 8.6 |
| Example 6 | 20.7 |
| Example 7 | 15.1 |
| Example 8 | 23.4 |
| Example 9 | 24.3 |
| Example 10 | 35.2 |
| Example 11 | 26.6 |
| Example 12 | 41.7 |
| Example 13 | 28.8 |
| Example 20 | 59.5 |
| Example 48 | 17.8 |
| Example 49 | 21.0 |
| Example 57 | 23.8 |

Example 121

Verifying the Tumor Inhibitory Effect of the Compounds on the Nude Mice

Referring the in vivo test methods recorded in "Antineoplastic Pharmacodynamics Guidelines" of SFDA, The inhibitory effect of 4-(3'-chloro-4'-fluorophenylamino)-6-[3-(2-oxa-6-azaspiro[3.4]octane-6-yl)-propoxy]-7-methoxy-quinazoline (Example 2, hereinafter referred to as Compound C) on the tumor of nude mice was evaluated.

After digesting and detaching the monolayer-cultured human lungs cancer cell strain A549 (purchased from Shanghai FuMeng Gene Bio-technology Co., Ltd.), cells were collected and resuspended in the serum-free culture medium, and the concentration was adjusted to be $2\times10^6/0.2$ mL. 0.2 mL cell suspension was taken by injector and transplanted under the skin of square scapula behind left armpit of nude mice, 0.2 mL for each mouse. The tumor volume was measured every 2 or 3 days. The nude mice bearing tumors which rapidly grew without any diabrosis were selected after two weeks. Under the condition of asepsis, the tumors were removed, and cut into tumor tissue with the diameter of approximately 2-3 mm, and then inoculate the tissue under the skin of square scapula behind left armpit of nude mice by trocar. After repetition in three generations, the nude mice received administration randomly in groups excluding the ones bearing too large or too small tumors, when the tumor grew to be about 100 $mm^3$ in volume.

The selected animals were 6-week old BALB/C nude mice. The male mice were 20-22 g in weight and provided by Shanghai Laboratory Animal Center (SIPPR BK) (production permit No. SCXK (Hu) 2008-0016). The experimental period was totally 111 days.

The experiment was randomly divided into 2 groups, the negative control group consisting of 12 mice (solvent administration only) and treatment group consisting of 12 mice (compound C, 100 mg/kg).

Ethanol was used as cosolvent to promote dissolution of compound C, adding 0.5 w/v % carboxymethyl cellulose to form suspension with a 0.5% final concentration of carboxymethyl cellulose and a 10 w/v % final concentration of ethanol, and then, using ultrasound to form uniform suspension. The dosage for intragastric administration was 0.1 ml/10 g, and the negative control group was only subjected to the same solvent. On the first day of experiment, compound C was given 100 mg/kg in the morning and in the evening respectively, and afterwards, 100 mg/kg was given in every morning only. The negative control group was only given 0.1 ml/10 g of 10 v/v % ethanol 0.5 w/v % carboxymethyl cellulose in every morning.

EXPERIMENTAL EVALUATION

Index: observing state of animals and measuring body weight daily; measuring tumors by calipers every two days. Sacrifice the animal in 24 hours after the last administration and measure the volume and size of tumor. Dissecting the animal and removing the tumor; weighing the tumor and nude mice; and then, drawing the curves of tumor volume and growth, nude mouse weight, tumor inhibition rate and animal death rate.

Tumor diameter measurement is used to observe the antitumor effect of the test substances dynamically. The formula for tumor volume (TV) calculation is:

$$v = 0.5 \times a \times b^2 (mm^3);$$

wherein, a and b stand for length and width respectively.

The relative tumor volume (RTV) is calculated according to the measurement result; RTV=Vt/V0, wherein V0 is the tumor volume measured at the beginning of administration (i.e. d0) and Vt is the tumor volume at each measurement.

The index to evaluate antitumor activity is relative tumor proliferation rate T/C (%)

$$T/C\ \% = \frac{TRTV}{CRTV} \times 100\%$$

In the above formula, TRTV: RTV of treatment group, CRTV: RTV of negative control group.

Tumor growth inhibition rate =

$$\frac{\text{Average tumor weight of administration group} - \text{average tumor weight of negative control group}}{\text{Average tumor weight of negative control group}} \times 100\%$$

The experiment was started after nude mice adapt to the environment of laboratory. During the whole experiment process, each group of planted nude mice behaved reduced activity, slightly reduced food intake, and normal drinking. About 4 days after administration, the activity of nude mice returned to normal gradually, and the food intake and the drinking returned to normal. Comparing with the control group, the body weight of the nude mice of the treatment group (compound C) is consistent fluctuation. The results are shown in FIG. 1.

After plantation, the formation of solid tumors can be touched in each nude mice group. At the same time in two days interval, the long diameters and the short diameters of the tumor were measured, and then, the volume of tumor is calculated accordingly. With the experiment proceeding, the tumor volume of the control group grows rapidly, and meanwhile the tumor volume of the treatment group grows relatively slowly. Two weeks after administration, the tumor volume and size of the treatment group is significantly less than the control group (p<0.05), and shown a statistically significant difference. The results are shown in FIG. 2.

The nude mice were sacrificed on the $21^{st}$ day after administration, and then, the tumors were removed and weighed. The average tumor weight of the treatment group is less than the negative group (P<0.05), and shown a statistically significant difference. According to the tumor volume and the tumor weight, the T/C % and the tumor inhibition rate are calculated. The results are shown in the table.

Table Inhibitory effects on tumors with nude mice

|  | Dose | Tumor volume (mm³) | RTV | T/C % | Tumor mass (g) | Tumor inhibition rate (%) |
|---|---|---|---|---|---|---|
| Negative group |  | 984.4 ± 315.8 | 10.52 ± 3.92 | 100 | 1.05 ± 0.42 | 0 |
| Treatment group | 100 mg/kg | 515.4 ± 388.0** | 4.57 ± 2.11** | 43.44 | 0.55 ± 0.43* | 47.62 |

*refers to the comparison with the Negative group, p < 0.05;
**refers to the comparison with the Negative group, p < 0.

The invention claimed is:

1. A heterocycle amino alkyloxy substituted quinazoline derivative of Formula II-III Formula II-III

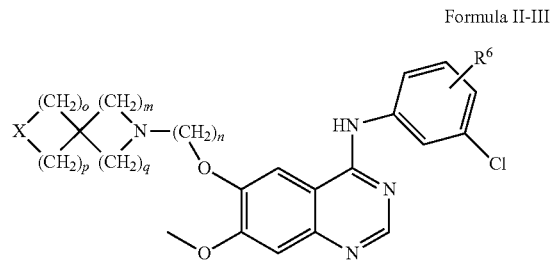

wherein group X is selected from the group consisting of

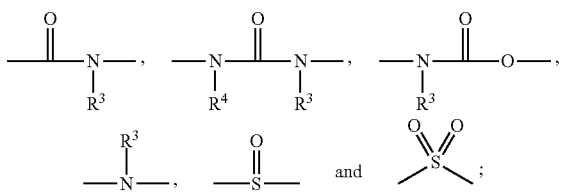

wherein each of group $R^3$ and group $R^4$ is independently selected from the group consisting of hydrogen, acyl, sulfonyl, substituted or unsubstituted C1-C6 alkyl, substituted or unsubstituted C3-C7 cycloalkyl, substituted or unsubstituted phenyl, and substituted or unsubstituted aromatic heterocycle;

m, and o are each independently an integer from 0 to 6;

n is an integer selected from 2 to 4;
p is 1, 2 or 3;
q is 1, 2 or 3; and
group $R^6$ is fluoro, chloro, bromo, cyano, or alkynyl;
or a pharmaceutically acceptable salt thereof.

2. A heterocycle amino alkyloxy substituted quinazoline derivative of Formula II-VI

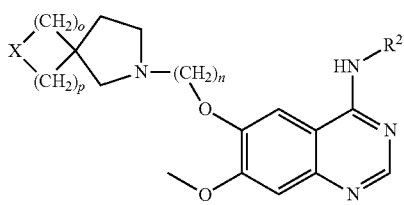

Formula II-VI wherein group X is selected from the group consisting of

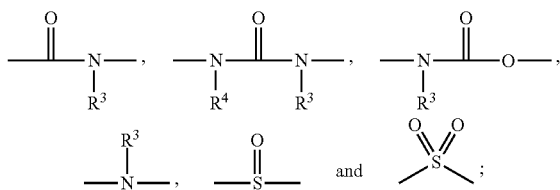

wherein each of group $R^3$ and group $R^4$ is independently selected from the group consisting of hydrogen, acyl, sulfonyl, substituted or unsubstituted C1-C6 alkyl, substituted or unsubstituted C3-C7 cycloalkyl, substituted or unsubstituted phenyl, and substituted or unsubstituted aromatic heterocycle;
o is 0, 1, 2 or 3;
wherein p is 1, 2 or 3;
n is an integer selected from 2 to 4; and
group $R^2$ is substituted or unsubstituted phenyl or substituted or unsubstituted aromatic heterocyclyl;
or a pharmaceutically acceptable salt thereof.

3. The heterocycle amino alkyloxy substituted quinazoline derivative according to claim 2, wherein group $R^2$ is phenyl having one or several substituents selected from the group consisting of halogen, alkyl, alkenyl and alkynyl.

4. The heterocycle amino alkyloxy substituted quinazoline derivative according to claim 2, wherein group $R^2$ is aromatic heterocyclyl having one or several substituents selected from the group consisting of halogen, alkyl, alkenyl and alkynyl.

5. The heterocycle amino alkyloxy substituted quinazoline derivative according to claim 2, wherein group $R^2$ is selected from the group consisting of

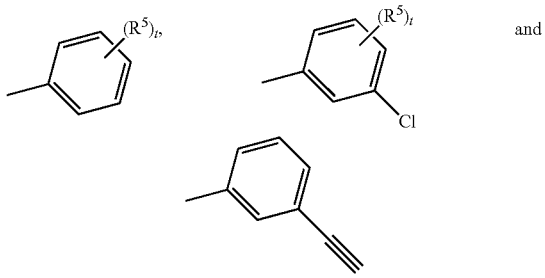

and wherein, t is 1 or 2; each group $R^5$, which may be the same or different, is independently selected from the group consisting of fluoro, chloro, bromo, cyano, and C2-C4 alkynyl; and wherein $R^6$ is selected from the group consisting of fluoro, chloro, bromo, cyano and alkynyl.

6. A pharmaceutical composition comprising a heterocycle amino alkyloxy substituted quinazoline derivative or a pharmaceutically acceptable salt thereof as an active ingredient, wherein the quinazoline derivative is selected from the group consisting of
compound 19: 4-(5'-chloro-2'-fluorophenylamino)-6-[3-(7-acetyl-2,7-diazaspiro[4.4]-nonane-2-yl)-propoxy]-7-methoxyquinazoline,
compound 22: 4-(5'-chloro-2'-fluorophenylamino)-6-[3-(2,7-diazaspiro[4.4]nonane-1-ketone-7-yl)-propoxy]-7-methoxyquinazoline,
compound 23: 4-(5'-chloro-2'-fluorophenylamino)-6-[3-(2-methyl-2,7-diazaspiro[4.4]nonane-1-ketone-7-yl)-propoxy]-7-methoxyquinazoline,
compound 27: 4-(5'-chloro-2'-fluorophenylamino)-6-[3-(2,6-diazaspiro[3.4]octane-7-ketone-2-yl)]-propoxy]-7-methoxyquinazoline,
compound 29: 4-(3'-chloro-2'-fluorophenylamino)-6-[3-(2,7-diazaspiro[4.4]nonane-1-ketone-7-yl)-propoxy]-7-methoxyquinazoline,
compound 30: 4-(3'-chloro-2'-fluorophenylamino)-6-[3-(2-methyl-2,7-diazaspiro[4.4]nonane-1-ketone-7-yl)-propoxy]-7-methoxyquinazoline,
compound 33: 4-(3'-chloro-2'-fluorophenylamino)-6-[3-(2,6-diazaspiro[3.4]octane-7-ketone-2-yl)]-propoxy]-7-methoxyquinazoline,
compound 35: 4-(3'-chloro-2'-fluorophenylamino)-6-[3-(3-methyl-1-oxa-3,7-diazaspiro[4.4]nonane-2-ketone-7-yl)-propoxy]-7-methoxyquinazoline,
compound 36: 4-(3'-chloro-2'-fluorophenylamino)-6-[3-(5-oxa-2,7-diazaspiro[3.4]octane-6-ketone-2-yl)-propoxy]-7-methoxyquinazoline,
compound 37: 4-(3'-chloro-2'-fluorophenylamino)-6-[3-(7-methyl-5-oxa-2,7-diazaspiro[3.4]octane-6-ketone-2-yl)-propoxy]-7-methoxyquinazoline,
compound 47: 4-(3'-ethynylphenylamino)-6-[3-(3-methyl-1-oxa-3,7-diazaspiro[4.4]nonane-2-ketone-7-yl)-propoxy]-7-methoxyquinazoline,
compound 48: 4-(3'-ethynylphenylamino)-6-[3-[(5-oxa-2,7-diazaspiro[3.4]octane-6-ketone-2-yl)-propoxy]-7-methoxyquinazoline,
compound 49: 4-(3'-ethynylphenylamino)-6-[3-[(7-methyl-5-oxa-2,7-diazaspiro[3.4]octane-6-ketone-2-yl)-propoxy]-7-methoxyquinazoline,
compound 51: 4-(3'-ethynylphenylamino)-6-[3-(7-acetyl-2,7-diazaspiro[4.4]-nonane-2-yl)-propoxy]-7-methoxyquinazoline,
compound 52: 4-(3'-chloro-4'-fluorophenylamino)-6-[2-(7-methyl-2,7-diazaspiro[4.4]nonane-2-yl)-oxethyl]-7-methoxyquinazoline,
compound 55: 4-(3'-chloro-4'-fluorophenylamino)-6-[2-(2,7-diazaspiro[4.4]-nonane-1-ketone-7-yl)-oxethyl]-7-methoxyquinazoline,
compound 57: 4-(3'-chloro-4'-fluorophenylamino)-6-[2-(2,6-diazaspiro[3.4]octane-7-ketone-2-yl)-oxethyl]-7-methoxyquinazoline,
compound 59: 4-(3'-chloro-4'-fluorophenylamino)-6-[2-(3-methyl-1-oxa-3,7-diazaspiro[4.4]nonane-2-ketone-7-yl)-oxethyl]-7-methoxyquinazoline,
compound 60: 4-(3'-chloro-4'-fluorophenylamino)-6-[2-(5-oxa-2,7-diazaspiro[3.4]octane-6-ketone-2-yl)-oxethyl]-7-methoxyquinazoline, compound 61: 4-(3'-chloro-4'-fluorophenylamino)-6-[2-(7-methyl-5-oxa-2,7-diazaspiro[3.4]octane-6-ketone-2-yl)-oxethyl]-7-methoxyquinazoline, compound 64: 4-(5'-chloro-2'-fluorophenylamino)-6-[3-(7-methyl-2,7-diazaspiro[4.4]nonane-2-yl)-propoxy]-7-methoxyquinazoline, compound 67: 4-(5'-chloro-2'-fluorophenylamino)-6-[3-(7-methyl-2,7-diazaspiro[4.4]-nonane-2-yl)-propoxy]-7-methoxyquinazoline, compound 68: 4-(3'-ethynylphenylamino)-6-[3-(7-methyl-2,7-diazaspiro[4.4]nonyl)-propoxy]-7-methoxyquinazoline, compound 70: 4-(3'-ethynylphenylamino)-6-[3-(2,7-diazaspiro[4.4]-nonane-1-ketone-7-yl)-propoxy]-7-methoxyquinazoline, compound 71: 4-(3'-ethynylphenylamino)-6-[3-(2-methyl-2,7-diazaspiro[4.4]-nonane-1-ketone-7-yl)-propoxy]-7-methoxyquinazoline, compound 76: 4-(3'-chloro-4'-fluorophenylamino)-6-[3-(7-methyl-2,7-diazaspiro[4.4]nonane-2-yl)-propoxy]-7-methoxyquinazoline, compound 77: 4-(3'-chloro-4'-fluorophenylamino)-6-[3-(7-tertbutyloxycarbonyl-2,7-diazaspiro[4.5]decane-2-yl)-propoxy]-7-methoxyquinazoline, compound 80: 4-(3'-chloro-4'-fluorophenylamino)-6-[3-(2,7-diazaspiro[4.4]-nonane-1-ketone-7-yl)-propoxy]-7-methoxyquinazoline, compound 81: 4-(3'-chloro-4'-fluorophenylamino)-6-[3-(2-methyl-2,7-diazaspiro[4.4]-nonane-1-ketone-7-yl)-propoxy]-7-methoxyquinazoline, compound 86: 4-(3'-chloro-4'-fluorophenylamino)-6-[3-(2,6-diazaspiro[3.4]octane-7-ketone-2-yl)-propoxy]-7-methoxyquinazoline, compound 89: 4-(3'-chloro-4'-fluorophenylamino)-6-[3-[3-methyl-1-oxa-3,7-diazaspiro[4.4]nonane-2-ketone-7-yl)-propoxy]-7-methoxyquinazoline, compound 90: 4-(3'-chloro-4'-fluorophenylamino)-6-[3-(5-oxa-2,7-diazaspiro[3.4]octane-6-ketone-2-yl)-propoxy]-7-methoxyquinazoline, compound 91: 4-(3'-chloro-4'-fluorophenylamino)-6-[3-(7-methyl-5-oxa-2,7-diazaspiro[3.4]octane-6-ketone-2-yl)-propoxy]-7-methoxyquinazoline, compound 92: 4-(3'-chloro-4'-fluorophenylamino)-6-[3-(7-acetyl-2,7-diazaspiro[4.4]-nonane-2-yl)-propoxy]-7-methoxyquinazoline, compound 96: 4-(3'-chloro-4'-fluorophenylamino)-6-[3-(3-methyl-1-oxa-3,7-diazaspiro[4.4]nonane-2-ketone-7-yl)-propoxy]-7-deuterated methoxyquinazoline, compound 97: 4-(3'-chloro-4'-fluorophenylamino)-6-[3-(5-oxa-2,7-diazaspiro[3.4]octane-6-ketone-2-yl)-propoxy]-7-deuterated methoxyquinazoline, compound 98: 4-(3'-chloro-4'-fluorophenylamino)-6-[3-(7-methyl-5-oxa-2,7-diazaspiro[3.4]octane-6-ketone-2-yl)-propoxy]-7-deuterated methoxyquinazoline, compound 101: 4-(3'-chloro-2'-fluorophenylamino)-6-[3-(3-methyl-1-oxa-3,7-diazaspiro[4.4]nonane-2-ketone-7-yl)-propoxy]-7-methoxyquinazoline, compound 102: 4-(3'-chloro-2'-fluorophenylamino)-6-[3-(5-oxa-2,7-diazaspiro[3.4]octane-6-ketone-2-yl)-propoxy]-7-methoxyquinazoline, compound 103: 4-(5'-chloro-2'-fluorophenylamino)-6-[3-(7-methyl-5-oxa-2,7-diazaspiro[3.4]octane-6-ketone-2-yl)-propoxy]-7-methoxyquinazoline, compound 106: 4-(3'-chloro-4'-fluorophenylamino)-6-[3-(6,6-dioxo-6-thia-2-azaspiro[3.4]octane-2-yl)propoxy]-7-methoxyquinazoline, compound 107: 4-(5'-chloro-2'-fluorophenylamino)-6-[3-(6,6-dioxo-6-thia-2-azaspiro[3.4]octane-2-yl)propoxy]-7-methoxyquinazoline, compound 108: 4-(3'-chloro-2'-fluorophenylamino)-6-[3-(6,6-dioxo-6-thia-2-azaspiro[3.4]octane-2-yl)propoxy]-7-methoxyquinazoline, and compound 109: 4-(3'-ethynylphenylamino)-6-[3-(6,6-dioxo-6-thia-2-azaspiro[3.4]octane-2-yl)propoxy]-7-methoxyquinazoline.

\* \* \* \* \*